(12) United States Patent
Bechtel et al.

(10) Patent No.: US 7,047,156 B1
(45) Date of Patent: May 16, 2006

(54) METHOD FOR ESTIMATING COMPLIANCE AT POINTS ALONG A BEAM FROM BENDING MEASUREMENTS

(75) Inventors: Friend K. Bechtel, Mead, WA (US); Chin S. Hsu, deceased, late of Pullman, WA (US); by Ning Wang, legal representative, Pullman, WA (US); Timothy C. Hanshaw, Pullman, WA (US)

(73) Assignee: Kierstat Systems LLC, Mead, WA (US)

( * ) Notice: Subject to any disclaimer, the term of this patent is extended or adjusted under 35 U.S.C. 154(b) by 153 days.

(21) Appl. No.: 10/318,711

(22) Filed: Dec. 14, 2002

(51) Int. Cl.
*G06F 17/18* (2006.01)

(52) U.S. Cl. .................. 702/179; 702/179; 702/181; 702/155; 702/33; 702/32; 238/169; 73/602; 73/781; 73/849; 73/852

(58) Field of Classification Search ............ 702/33, 702/32, 155, 179, 181; 238/169, 151; 73/849, 73/602, 1.07; 450/45
See application file for complete search history.

(56) References Cited

U.S. PATENT DOCUMENTS

| | | | |
|---|---|---|---|
| 5,503,024 A | | 4/1996 | Bechtel et al. |
| 6,026,689 A | * | 2/2000 | Snyder et al. ............... 73/602 |
| 6,101,450 A | * | 8/2000 | Dasgupta ..................... 702/42 |

OTHER PUBLICATIONS

Zook et al., 'Resonant Micro–Beam Strain Transducers', 1991, IEEE, pp. 529–532.*
Li et al., 'Adaptive Vibration Isolation for Axially Moving Beams', Dec. 2000, IEEE, pp. 419–428.*

Bechtel, F.k. "Beam Stiffness as a Function of Pointwise E with Application to Machine Stress Rating", Proceedings Int'l. Symposium on Forest Products Research CSIR, Pretoria SA., 1985 pp 2–4,13.

Bechter & Allen,"Intro. to the Metriguard Model 7200 LS Lumber Tester", MSR Lumber Producers Council Mtg., Vancouver, B.C. Canada, 1995. All, but particularly Fig. 13, p. 13.

Foscii, R.O., "A Procedure for the Determination of Localized Modulus of Elasticity", Holzals Roh–und Werkstoff 45(1987). All pages.

Pope & Matthews, "A Comparison of Deconvolution Techniques to Improve MOR Estimation from Stress Grading Machine Ouput", Wood Science & Tech. 29, 1995. All pages.

(Continued)

*Primary Examiner*—Marc S. Hoff
*Assistant Examiner*—Elias Desta

(57) ABSTRACT

The inherent smoothing in bending stiffness measurement of wood boards as occurs in the machine grading of lumber can mask the effect of knots and other local characteristics affecting structural value. Improved estimates of local (pointwise) stiffness will be useful in decisions about further processing and use of a tested board. Measured compliance is reciprocally related to measured stiffness and is the convolution of local compliance and a "span function". Span function is specific to the bending span configuration used and can change during measurement of a board. A general procedure for computing span function, which heretofore has been known only for simple bending spans, is disclosed. A Kalman filter uses this and other available information to optimally estimate local compliance from an observed relationship between local compliance and state variables of a state-space model. Method for linear algebraic determination of local compliance also depends on span functions and is disclosed.

20 Claims, 19 Drawing Sheets

OTHER PUBLICATIONS

Kalman, R.E. "A New Approach to Linear Filtering & Prediction Problems", Trans. ASME, Journal Basic Engineering, Series 82D, 1960. All pages.

Kailath, et al., 2000, *Linear Estimation*, Prentice–Hall Upper Saddle River NJ. pp. 18, 19, 766, 767.

Ogata, K., 1987, *Discrete Time Control Systems*, Prentice–Hall, Englewood Cliffs, NJ. pp. 484–487.

Papoulis, A., 1991, Probability, Random variables and stochastic Processes, McGraw–Hill, NY, NY. pp. 457–458.

Hayes, M.H.,1996, *Statistical Digital Signal Processing and Modeling*, Wiley & Sons, NY, NY. pp. 108–113.

Rao, C.R., 1965, *Linear Statistical Inference and its Applications*, Wiley & Sons, NY, NY, pp. 181,182.

Strang & Borre, 1997, *Linear Algebra, Geodesy, and GPS*, Wellesley–Cambridge Press, Wellesley MA. pp. 266–269.

\* cited by examiner

| k | Output Matrix | Compliance Measurement | Kalman Filter Input | Pointwise Compliance Estimate | Residual Error Variance |
|---|---|---|---|---|---|
| 12 | H1 | $C_m(12)$ | $c_m(12) = 0$ | | |
| 13 | H1 | $C_m(13)$ | $c_m(13) = C_m(13) - C_m(12)$ | | |
| 14 | H1 | $C_m(14)$ | $c_m(14) = C_m(14) - C_m(12)$ | | |
| 15 | H1 | $C_m(15)$ | $c_m(15) = C_m(15) - C_m(12)$ | | |
| 16 | H2 | $C_m(16)$ | $c_m(16) = C_m(16) - C_m(12)$ | | |
| 17 | H2 | $C_m(17)$ | $c_m(17) = C_m(17) - C_m(12)$ | | |
| 18 | H2 | $C_m(18)$ | $c_m(18) = C_m(18) - C_m(12)$ | | |
| 19 | H3 | $C_m(19)$ | $c_m(19) = C_m(19) - C_m(12)$ | $C^*(1) = s_1^*(19) + C_m(12)$ | $P_{1,1}(19)$ |
| 20 | H3 | $C_m(20)$ | $c_m(20) = C_m(20) - C_m(12)$ | $C^*(2) = s_1^*(20) + C_m(12)$ | $P_{1,1}(20)$ |
| ... | ... | ... | ... | ... | ... |
| k | H3 | $C_m(k)$ | $c_m(k) = C_m(k) - C_m(12)$ | $C^*(k-18) = s_1^*(k) + C_m(12)$ | $P_{1,1}(k)$ |
| ... | ... | ... | ... | ... | ... |
| $k_f-7$ | H3 | $C_m(k_f-7)$ | $c_m(k_f-7) = C_m(k_f-7) - C_m(12)$ | $C^*(k_f-25) = s_1^*(k_f-7) + C_m(12)$ | $P_{1,1}(k_f-7)$ |
| $k_f-6$ | H4 | $C_m(k_f-6)$ | $c_m(k_f-6) = C_m(k_f-6) - C_m(12)$ | $C^*(k_f-24) = s_1^*(k_f-6) + C_m(12)$ | $P_{1,1}(k_f-6)$ |
| $k_f-5$ | H4 | $C_m(k_f-5)$ | $c_m(k_f-5) = C_m(k_f-5) - C_m(12)$ | $C^*(k_f-23) = s_1^*(k_f-5) + C_m(12)$ | $P_{1,1}(k_f-5)$ |
| $k_f-4$ | H4 | $C_m(k_f-4)$ | $c_m(k_f-4) = C_m(k_f-4) - C_m(12)$ | $C^*(k_f-22) = s_1^*(k_f-4) + C_m(12)$ | $P_{1,1}(k_f-4)$ |
| $k_f-3$ | H5 | $C_m(k_f-3)$ | $c_m(k_f-3) = C_m(k_f-3) - C_m(12)$ | $C^*(k_f-21) = s_1^*(k_f-3) + C_m(12)$ | $P_{1,1}(k_f-3)$ |
| $k_f-2$ | H5 | $C_m(k_f-2)$ | $c_m(k_f-2) = C_m(k_f-2) - C_m(12)$ | $C^*(k_f-20) = s_1^*(k_f-2) + C_m(12)$ | $P_{1,1}(k_f-2)$ |
| $k_f-1$ | H5 | $C_m(k_f-1)$ | $c_m(k_f-1) = C_m(k_f-1) - C_m(12)$ | $C^*(k_f-19) = s_1^*(k_f-1) + C_m(12)$ | $P_{1,1}(k_f-1)$ |
| $k_f$ | H5 | $C_m(k_f)$ | $c_m(k_f) = C_m(k_f) - C_m(12)$ | $C^*(k_f-18) = s_1^*(k_f) + C_m(12)$ | $P_{1,1}(k_f)$ |
| | | | | $C^*(k_f-17) = s_2^*(k_f) + C_m(12)$ | $P_{2,2}(k_f)$ |
| | | | | ... | ... |
| | | | | $C^*(k_f+11) = s_{30}^*(k_f) + C_m(12)$ | $P_{30,30}(k_f)$ |

Fig. 4

METHOD FOR ESTIMATING COMPLIANCE AT POINTS ALONG A BEAM FROM BENDING MEASUREMENTS

FEDERALLY SPONSORED RESEARCH

In part, this material is based upon work supported by the U.S. Department of Agriculture under Grant No. 00-33610-8896. Any opinions, findings, and conclusions or recommendations expressed in this publication are those of the author and do not necessarily reflect the views of the U.S. Department of Agriculture.

FIELD OF INVENTION

This invention relates to new method for processing measurements of bending stiffness (or its reciprocal, compliance) in beams; specifically, the new method may be applied to estimate compliance and hence modulus of elasticity at points along a wood board.

REFERENCES CITED IN THE SPECIFICATION

The description of the specification draws freely from references listed here alphabetically by author. When referred to in the specification, a reference is identified by author and date, e.g. (Richburg et al. 1991).

Bechtel, F. K., 1985, "Beam stiffness as a function of pointwise E, with application to machine stress rating", Proc. International Symposium on Forest Products Research, CSIR, Pretoria, South Africa.

Bechtel, F. K. and J. R. Allen, 1995, Introduction to the Metriguard Model 7200 LS Lumber Tester, MSR Lumber Producers Council Meeting, Vancouver B. C. Canada.

Bechtel, F. K., R. K. Byers, J. D. Logan, J. R. Allen, M. G. Strevy, and D. A. Uskoski, 1996, U.S. Pat. No. 5,503,024, "Apparatus for Testing Lumber Stiffness".

Bechtel, F. K., 2001, "Kalman filter derivation per Kalman", available from author.

Bechtel, F. K., 2002, "Span function for multiply supported beams", available from author.

Dunne, M. J. and K. K. Lau, 2000, U.S. Pat. No. 6,055,867, "Panel Testing Apparatus and Method".

Foschi, R. O., 1987, "A procedure for the determination of localized modulus of elasticity", Holz als Roh-und Werkstoff 45:257–260.

Guillemin, E. A., 1949, Mathematics of Circuit Analysis, MIT Press, Cambridge Mass.

Hayes, M. H., 1996, Statistical Digital Signal Processing and Modeling, Wiley & Sons, New York N. Y.

Hernandez, R., D. A. Bender, B. A. Richburg, and K. S. Kline, 1992, Probabilistic modeling of glued-laminated timber beams", Wood and Fiber Science, 23(3):294–306.

Higdon, A., E. H. Ohlsen, and W. B. Stiles, 1960, Mechanics of Materials, Wiley & Sons, New York N. Y.

Kailath, T., A. H. Sayed and B. Hassibi, 2000, Linear Estimation Prentice-Hall Upper Saddle River N. J.

Kalman, R. E., 1960, "A new approach to linear filtering and prediction problems", Trans. ASME Journal Basic Engineering, Series 82D, pp. 3545.

Kline, D., F. E. Woeste and B. A. Bendtsen, 1986, "Stochastic model for modulus of elasticity of lumber", Wood & Fiber Science, 18(2):228–238.

Lam, F., R. O. Foschi, J. D. Barrett, and Q. Y. He, 1993, "Modified algorithm to determine localized modulus of elasticity of lumber", Wood Science and Technology, 27:81–94.

Lau, K. K. and J. T. Yelf, 1987, U.S. Pat. No. 4,708,020, "Temperature Compensated Continuous Panel Tester".

Ogata, K., 1987, Discrete Time Control Systems, Prentice-Hall, Englewood Cliffs N.J.

Oppenheim, A. V. and R. W. Schafer, 1989, Discrete Signal Processing, Prentice-Hall, Englewood Cliffs N.J.

Papoulis, A., 1991, Probability, Random Variables and Stochastic Processes, McGraw-Hill, N. Y. N.Y.

Pope, D. J. and F. W. Matthews, 1995, "A comparison of deconvolution techniques to improve MOR estimation from stress grading machine output", Wood Science and Technology, 29, pp. 431–439.

Rao, C. R., 1965, Linear Statistical Inference and its Applications Wiley & Sons, New York N.Y.

Richburg, B. A., R. Hernandez, B. J. Hill and D. A. Bender, 1991, "Machine stress grading for determining localized lumber properties", Paper No. 91-4542, International Winter Meeting of the ASAE. Chicago Ill.

Richburg, B. A. and D. A. Bender, 1992, "Localized tensile strength and modulus of elasticity of E-rated laminating grades of lumber", Wood and Fiber Science, 24(2):225–232.

Schwarz, R. J. and B. Friedland, 1965, Linear Systems, McGraw-Hill, New York N. Y.

Strang, G. and K. Borre, 1997, Linear Algebra, Geodesy, and GPS, Wellesley-Cambridge Press, Wellesley Mass.

Taylor, S. E. and. D. A. Bender, 1989, "A method for simulating multiple correlated lumber properties", Forest Products Journal, 39(7/8):71–74.

Taylor, S. E. and D. A. Bender, 1991, "Stochastic model for localized tensile strength and modulus of elasticity in lumber", Wood and Fiber Science, 23(4):501–519.

Taylor, S. E., D. A. Bender, D. E. Kline and K. S. Kline, 1992, "Comparing length effect models for lumber tensile strength", Forest Products Journal, 42(2):23–30.

BACKGROUND OF THE INVENTION

In one type of process for the production of stress rated lumber, the bending modulus of elasticity (MOE) of each wood board is measured. MOE is an intrinsic material property, which, together with board dimensions, determines bending stiffness. MOE and other characteristics of the board are used to categorize it into a grade. Off-line quality control tests help to assure that boards in the higher grades have the properties required in those grades. Examples in North America include MSR (Machine Stress Rated) and MEL (Machine Evaluated Lumber) lumber grades.

Measurements of bending MOE in a board require a bending span of some length over which to apply and/or measure bending forces and deflections. The resulting determination of bending MOE, denoted $E_m$, is a composite result, which represents the intrinsic MOE values at points along the board corresponding to the length segment of the board coinciding with the bending span. Because each measurement is a composite, the values $E_m$ so obtained are smoothed versions of the underlying pointwise MOE values. Measurement of MOE by bending is inherently a smoothing operation.

In wood boards, this smoothing is an issue because of widely varying structural characteristics within a board. Knots and grain angle deviations are among the characteristics affecting structural value. Structural failures of wood boards are often associated with local characteristics of the boards rather than with their average properties. Smoothing, as a result of bending measurements, can mask variations in local, i.e. pointwise, values that, if estimated more accurately, could identify structural problems. Enhanced estimation accuracy will be useful in the determination of further manufacturing, processing or use of the board, including as input to other processes for the same purposes.

A production-line machine used in North America and elsewhere for measuring MOE of wood boards is known as the HCLT (High Capacity Lumber Tester) and is manufactured by Metriguard Inc in Pullman Wash. The HCLT follows specification of U.S. Pat. No. 5,503,024 (Bechtel et al. 1996).

In the HCLT, a wood board to be tested enters and passes longitudinally through it, typically at speeds exceeding 6 m/s (1200 ft/min). Overlapping length segments for measurement points along the board are each presented sequentially to two bending sections and bent downward in a first bending section and then upward in a second bending section. Bending spans in each bending section are defined by rollers at support points that apply bending deflections and forces to the board. At the center of each bending section, the force at a roller support is measured by an electronic load cell. Measured forces from the two bending sections are averaged, a differential time delay being required to match measurements from the same length segment along the board. By averaging downward and upward forces, the measurements are compensated for lack of straightness in the board. Each MOE measurement is determined by scaling an average force measurement.

In the HCLT, detail of MOE along the board is lost due to the inherent smoothing previously mentioned.

The following is a description of related prior art that attempts to alleviate the smoothing effect of bending measurements and obtain greater detail.

Prior Art 1. Shorter Bending Spans

One obvious method for estimating MOE more locally than in the HCLT, and hence for reducing smoothing, is to reduce lengths of bending spans. The central part of a fill seven-support bending span in the HCLT covers a board segment length of 1219 mm (48 inch), although the total extent between first and last supports is 2032 mm (80 inch). For this discussion of the possibility of using shorter spans, weighting of effects from board segments outside the 1219 mm central part of the span may be considered negligible.

Other production-line machines have been used with bending spans having length 900 mm (35 in). However, these machines have only three support points as opposed to the seven supports of the HCLT. The multiple supports of the HCLT approximate fixed end conditions. Comparison has shown that a seven-support span of the HCLT provides a more localized result than shorter (900 mm) spans using center-loaded simple supports (Bechtel and Allen 1995).

It would be possible to redesign and reduce the bending span lengths used in any of the bending machines. However, precision of roller positioning, pitch buildup on rollers, bearing precision, compression of wood fibers at roller-to-wood contact points, machine rigidity, and wood surfacing tolerances all become more critical with shorter spans. Reduced accuracy of bending measurement is a consequence of reduced bending span lengths. Present designs have considered these tradeoffs, and present-day equipment for testing boards having dimension in the direction of bending in the usual range of about 35 to 45 mm (including 1.5 inch) are a reasonable compromise. Regardless of bending span length chosen, bending measurements are still inherently composites and hence smoothed versions of local values.

Prior Art 2. (Bechtel 1985)

This prior art research showed that the smoothing is described mathematically as applying to the reciprocal of MOE called compliance. It was shown that the measured compliance along a beam is the convolution integral of the unknown local compliance function and a weighting function h(x) hereinafter called "span function". Span function h(x) was derived for the special case of a three-support, center-loaded bending span having length L. The span function h(x) shows how much each local compliance value is weighted into the measured compliance. Thus, h(x) determines the weights in a weighted average of the local compliances in their contribution to the measurement. For the simple three-support case mentioned, the span function is given by:

$$h(x) = \begin{cases} \left(\frac{12}{L^3}\right)\left(\frac{L}{2} - |x|\right)^2, & |x| \le L/2 \\ 0, & \text{otherwise.} \end{cases}$$

From Prior Art 2, with some change in independent variable definition, measured compliance $C_m(w)$ may be written as the convolution integral (using * to indicate convolution):

$$C_m(w) = h(w) * C(w)$$
$$= \int_{-L/2}^{+L/2} h(w)C(w-x)dx$$

where w is a point of measurement on the beam, measured from the beam's leading end and identifying where the bending span is being applied.

Prior Art 2 suggests recovering the local compliance values C(w) by use of the well-known complex convolution theorem, which turns convolution into multiplication if the Fourier Transform is taken. Specifically:

$$\overline{C_m}(f) = \overline{h}(f)\overline{C}(f)$$

where the overbar indicates Fourier Transform, and f is a frequency variable. The idea is to divide and take the inverse Fourier Transform (ift) to obtain the local compliance estimates C*(w) as:

$$C^*(w) = ift(\overline{C}(f))$$
$$= ift\left(\frac{\overline{C_m}(f)}{\overline{h}(f)}\right)$$

where the superscript asterisk * indicates estimate. Carrying out the indicated operations on real data gives estimates that are dominated by high frequency noise. The reason for this may be seen if measurement noise v(w) at w is additive to the measurement of compliance according to the model;

$$C_m(w) = h(w) \cdot C(w) + v(w)$$

Then, the above result for C*(w) becomes:

$$C^*(w) = ift\left(\frac{\overline{C_m}(f)}{\overline{h}(f)}\right)$$
$$= ift\left(\frac{\overline{C}(f)\overline{h}(f) + \overline{v}(f)}{\overline{h}(f)}\right)$$
$$= C(w) + ift\left(\frac{\overline{v}(f)}{\overline{h}(f)}\right)$$

At high frequencies, the Fourier Transform $\overline{v}(f)$ of the noise is significant and the Fourier Transform $\overline{h}(f)$ of the span function is very small. The second term involving noise can be very large.

Prior Art 3. (Foschi 1987)

Using the deconvolution suggestion of Prior Art 2, Foschi reduced noise by truncating high frequency noise components. Using simulated data, Foschi concluded that noise problems could be alleviated and the deconvolution process made practical.

Prior Art 4. (Richburg et al. 1991)

Richburg, et al. reported that, while Foschi's method gave close approximations to simulated data, attempts to verify his method with experimental data were unsuccessful.

Prior Art 5. (Lam et al. 1993)

Lam et al. elaborated on noise reduction and refined Foschi's frequency truncation method.

Prior Art 6. (Pope and Matthews 1995)

Pope and Matthews further expanded on Foschi's frequency truncation approach. They correlated bending strength with estimates of local MOE nearest the failure and also with machine measured MOE nearest the failure. Pope and Matthews concluded that the estimated local MOE results from any of Foschi's, Lam et als.' or their own work gave no meaningful improvement in correlation over the direct machine measurement of MOE.

Prior Art 7. (Bechtel and Allen 1995)

A figure was presented illustrating span functions for both a seven-support bending span of an HCLT and for a three-support bending span. Derivation of the span function for the seven-support system was not disclosed, nor was it correct for the figure presented (a correct general approach for determining span functions is a part of the present specification for estimating local compliance). Because of the scale and resolution of the figure in this prior art disclosure, errors caused by the incorrect span function derivation are not easily apparent. The seven-support HCLT span function was compared with span functions for three-support, center-loaded bending spans. The conclusion that measurement resolution of an HCLT seven-support bending span is better than the resolution of shorter three-support, center-loaded bending spans was correct.

Further Discussion of Prior Art

The span function for a three-support, center-loaded bending span was mistakenly used to analyze the CLT (Bechtel 1985) which is an earlier machine similar to the HCLT. The difference in span functions for the CLT and the HCLT compared to the three-support span function is significant. Bechtel reported the error, apparently in time to prevent erroneous application to real data from the CLT. Others (Foschi 1987, Richburg et al. 1991, Lam et al. 1993, Pope and Matthews 1995) have processed signals using only span functions for three-support, center-loaded spans. The prior art includes no data analyzed with span functions for the more complicated seven-support bending spans. No optimal method exists in the prior art for estimating local compliance (or MOE). In one of the prior art papers, the span function for a three-support, center loaded bending span may have been used to weight local MOE values directly rather than their reciprocals. There is no theoretical support for this use of the span function.

All of the above referenced prior art that attempt local estimation by deconvolution reduce noise by truncation of information above a cutoff frequency. While that method is helpful, it is ad hoc and suboptimal.

Local compliance estimation by deconvolution in Prior Art 2, 3, 4, 5, and 6 requires use of Fourier Transforms. In practice, this leads to complications, particularly for points near the ends of a beam. Fourier methods cause artifacts at discontinuities, e.g. Gibb's Phenomenon (Guillemin 1949), that must be considered and compensated or otherwise accounted for.

Although a summary of prior art research (Pope and Matthews 1995) is pessimistic about usefulness of local MOE estimation, the above discussion identifies reasons why the prior art efforts were not particularly successful.

Preliminaries

The new method of this specification uses equations, called beam equations, developed from flexural loading theory found in elementary texts on mechanics of materials, e.g. (Higdon et al. 1960). As opposed to the usual analyses, MOE is not assumed constant along the beam. Local MOE, namely E, or E(w) to indicate its dependence on position, appears in the denominators of the beam equations along with cross-sectional area moment of inertia I as a product EI. In some cases I is also a function of position w along the beam, and then it is written I(w). Details for computation of I from cross-sectional geometry may be found in basic references. In the case where the beam has a rectangular cross-section, $I=\gamma_1\gamma_2^3/12$, where $\gamma_1$ and $\gamma_2$ respectively are orthogonal cross-sectional dimensions perpendicular to and in the plane of bending.

Because E appears with I as a product in the beam equations, this product may be treated as a single parameter that can vary with position along the beam. Thus, the new method may be applied to beams with variable E, I, or EI product along the length.

Conventional analyses are built around MOE. MOE is an intrinsic material property defined as the ratio of stress to strain at a point. The reciprocal ratio of strain to stress could equally well have been defined and used. In this specification, it is asserted that the span function weighting discussed above, should be applied to the reciprocal of E. In cases where just I varies with position, the weighting is applied to the reciprocal of I. In cases where E and I both vary and hence are considered together as a product, the weighting applies to the reciprocal of the EI product. Use of reciprocals of the normally considered quantities is a natural outcome of the development and occurs because E and I are in the denominators of the beam equations. Modulus of elasticity appears in the discussion only because it is so deeply embedded by convention in the minds and literature of those working in the field.

To ease the complexity of notation and maintain generality of the result, the notation C is used to indicate any of the reciprocals 1/E, 1/I, or 1(EI) depending on whether E, I, or EI are considered as varying with position w. The new method is equally applicable for any of these cases. Similarly, measured compliance $C_m$ can be any of $1/E_m$, $1/I_m$, or $1/(E_m I_m)$. In the case where one or the other of E or I is constant, that constant value can be removed from the integrals involved and combined with other constants. Unless otherwise indicated, in the development of the equations, where it is helpful to check dimensions, it is assumed that C=1/(EI), and $C_m=1(E_m I_m)$ Symbols $C_m$ and $E_m$ without subscript refer to local compliance and MOE values, and symbols $C_m$ and $E_m$ with subscript "m" refer to measured compliance and MOE values. When written as functions of an argument, as in C(w) or Cm(w), the argument is taken as the distance from the leading end of a beam, which, in this specification, is the right end with w measured leftward. All compliance and MOE measurements in this specification are assumed to be in bending. The use of the abbreviation MOE is reserved for modulus of elasticity in general.

For a bending span, measured compliance Cm(w) is a weighted composite of local compliance values C(u) for u in a neighborhood of w. The weighting with which each C(u) contributes to the measurement $C_m(w)$ is defined by a span function specific to the bending span. Knowledge of the span function is essential in the optimal estimation of local compliance values.

The phrase "bending span" refers to a beam support configuration, with supports at specified points in the beam's longitudinal direction. At the supports, forces and deflections to the beam are applied and or measured in a direction substantially perpendicular to the beam's length and substantially in the plane of bending. Moments and slopes are not specifically considered except at beam ends, because they can be applied and or measured by forces and deflections at closely spaced pairs of support points.

Applied to a beam at a measurement point w on the beam, bending span implies a derived functional relationship expressing the measured compliance $C_m(w)$ as a functional of local compliance along the beam. Corresponding with the bending span for each measurement point w is a length segment of the beam, usually the distance between first and last of the bending span support points, from which local compliance values affect $C_m(W)$. Thus, $C_m(W)$ is associated with a particular bending span, measurement point, length segment, and span function, as well as the local compliance values.

For different measurement points w along the beam, the bending span, and hence span function, can change. For example, in an HCLT bending section there are seven supports. When a measurement point w is near the center of a wood board, all supports are active; but, if w is 30 inch from an end of the board, only five supports are active. The bending spans for the two cases are different and different span functions are applicable. The new method uses corresponding sequences of measured compliance values $C_m$ and span functions to optimally estimate local compliance values C.

High-speed present day measuring equipment for testing wood boards uses force measurements to provide results in units of MOE. In that case, the taking of reciprocals will provide a sequence of compliance measurements $C_m$. Values of compliance obtained either by measuring them directly or by taking reciprocals of measured MOE are referred to as measured compliance values or just compliance measurements and designated with the symbol $C_m$ or $C_m(w)$ as a function of measurement position.

In the result, local MOE estimates $E^*(w)$ may be obtained from local compliance estimates $C^*(w)$ by taking reciprocals, e.g. $E^*(w)=1/C^*(w)$, and modified with a correction to be described. The superscript asterisk is used to indicate estimates.

In the case of estimated values, the reciprocal relationship between $E^*(w)$ and $C^*(w)$ must be considered with caution. Each estimated compliance value $C^*$ is taken as the mean value of its estimator C, and quality of the estimate may be taken as either the variance of the estimator or its coefficient of variation COV. Coefficient of variation of an estimator is defined as the ratio of standard deviation divided by the mean. Estimator E for local MOE is obtained from the reciprocal distribution of C, i.e. from the distribution of E=1/C. But, the mean of a reciprocal distribution is not equal to the reciprocal of the mean, although it may be close if COV is small. It can be shown from statistical methods (Papoulis 1991) that a first correction for the mean and COVE of estimator E may be given approximately in terms of the mean and $COV_C$ of estimator C according to:

$$E^* \cong \frac{1}{C^*}(1 + COV_C^2)$$

$$COV_E \cong COV_C\left(\frac{1}{1 + COV_C^2}\right)$$

If $COV_C$<<1, then $E^* \cong 1/C^*$, and $COV_E \cong COV_C$. Accuracy is improved if the correction factor $(1+COV_C^2)$ is used as shown. In this specification, optimal compliance estimates $C^*$ and $COV_C$ are the result. When E estimates $E^*$ and COVE are required, the above relationships with correction are used.

The preferred and alternative embodiments are examples where the method applies to apparatus used for bending measurements of wood boards. However, it can be applied equally well to bending measurements of any elongated beam. For example, it could be applied to bending measurements on panel products by apparatus (Lau and Yelf 1987, Dunne and Lau 2000) which bend panels. The method does not require a continuous movement or rolling of a beam relative to a bending span, although that is the means often employed. The method is applicable to any type of beam and not just those made of lignocellulosic material.

Local compliance at w is representative of the cross-section at w, and is a composite of intrinsic compliance values for all points within that cross-section. How each of the compliance values within the cross-section contributes to local compliance at w may be found elsewhere; e.g. (Bechtel 1985). No attempt is made in this specification to use bending compliance measurements to deduce the intrinsic compliance at points within a cross-section. Rather, they are used to estimate local compliance values C at points along the length of a beam.

Measurements are samples of a continuous function $C_m(w)$ at a sequence of measurement points, i.e. at discrete values of the argument w, separated by a sampling increment d. Typically, by nature of bending tests, the sequence of measurement points begins and ends at a distance greater than some multiple of d from beam ends.

Estimates of local compliance by the new method are identified with discrete cross sections along the beam length. However, each may be taken as representative of local compliance at points within half the sampling increment d of a cross section. Thus, the estimates represent the compliance for elements of a subdivision of the beam length.

In the above description and for the preferred embodiment description, the subdivision is regular-, that is, each sampling increment has length d. This restriction to a regular subdivision, as opposed to an irregular subdivision wherein sampling increments are not all the same length, simplifies data processing and is a convenient but not a necessary restriction of the method.

Objects and Advantages of the New Method

The new method is able to provide optimal estimates for general bending span configurations, not just for simple cases where span function is easily obtainable by prior art methods. As a necessary part of the method, a general procedure is disclosed for computing span functions.

The new method optimally estimates local compliance values C along a beam and provides a measure of estimation quality for each estimate.

The new method provides estimates of local compliance out to the ends of a measured beam, thereby addressing one of the objections of bending measurements. Estimation quality is reduced at points near the beam ends, as one would expect, because fewer compliance measurements are used in the estimation at those points. Also, the amount of the contribution to any measured compliance from a local compliance value near the ends of a tested beam is small. But, for the first time, a measure of estimation quality is provided and a priori information is used to help extend estimation to these previously unavailable segments of the beam.

The new method can accommodate changes in the bending span as a wood board moves through a machine such as the HCLT. When the leading end of the board enters a bending section of an HCLT, useful data are obtained before all seven supports are engaged. Data are obtained as the bending span number of supports is first 5, then 6, and then 7 corresponding to the leading end of the board engaging additional supports. Similarly, the number of supports changes from 7 to 6 to 5 as the trailing end progresses through the bending section and disengages from supports. The changing number of supports and hence bending span is addressed herein by using bending spans and hence span functions specific for each measurement point. There is no known approach to account for this non-stationarity of bending span with any of the Fourier methods.

The new method works in the same domain as the data and does not require transformations to the frequency domain and back. It thereby avoids these processing steps and the necessity of dealing with discontinuity effects at board ends.

The new method is recursive. Each estimate is used in obtaining the next. The optimal compliance estimate for a point of estimation along a board may be computed as soon as the compliance at that point no longer contributes to any remaining compliance measurements. In an HCLT, except for a small delay due to a decimation preprocessing step to be described, this is as soon as the element being estimated exits the last data producing bending span defined in the second bending section. This helps to make the process practical in real time on a production line. The prior art Fourier Transform methods require that the entire data stream be processed together.

The new method allows inclusion of available a priori information in practical models of the random process describing beam compliance measurements. Parameters describing an autoregressive random process for local compliance of the beam may be learned from autocorrelation values obtained from compliance measurements for sufficiently long lags. Bending span parameters (weighting coefficients) for inclusion in the moving average part of an autoregressive moving average (ARMA) model of beam compliance measurements are determined by the disclosed procedure for computing span function and computing weights from span function. Statistics of measurement noise may be included as part of the model, and other confounding noise sources may be modeled.

Inclusion of available a priori information is important in obtaining the best estimates possible. For example, vibration noise sometimes contributing to the output signal from the HCLT machine may be included in the model, and the estimated component of compliance measurement attributed to vibration noise may be excluded from local compliance estimates. Moreover, the estimated vibration noise component may be developed into a measure of machine performance and as an indicator for maintenance. The model framework allows other noise processes to be included as they become known with consequent improvement in compliance estimation quality.

The new method can use additional measurements that are affected by the local compliance values to improve quality of local compliance estimation. While the embodiments describe a scalar compliance measurement sequence, the new method allows vector measurements. Other scalar measurements, that are affected by local compliance, may be used as additional components of a measurement vector. For example, it may prove desirable to uncouple the prior art process of averaging measurements from a second section HCLT bending span with delayed measurements from a first section HCLT bending span. Then, the separate measurements from the two bending sections would be included in a more complex model having a two-dimensional vector measurement sequence.

Measurements that are affected by beam parameters other than local compliance may be included and these other parameters estimated by the same method framework. This can lead to a more comprehensive indicator of beam quality than provided by compliance measurements alone.

The new method provides a measure of estimation quality. Variances of the compliance estimators are part of the computed results. Either variance or COV may be used as a quality measure.

SUMMARY OF THE INVENTION

Overview

The new method uses a Kalman filter (Kalman 1960) to optimally estimate compliance at points along a beam, that is, for elements in a subdivision of the beam length, from bending measurements of the beam. The bending measurements are compliance measurements at a sequence of measurement points along the beam.

The new method is intimately associated with the bending span applicable for each measured compliance and the span function for it. The steps disclosed for computing span function are broadly applicable. Bending equations are written which involve locations of beam support points, bending deflections, and bending forces at the supports, and the local compliance function for the beam.

Weight coefficients are computed from the span function, and the new method uses them in an output equation of a state-space model of a dynamic system. State variable components of a state vector are modeled as unknown local compliance values for the part of the beam covered by the bending span. Further definition of the system model shows the state to evolve from input and from a previous state with a state matrix as successive compliance measurements are taken.

The state matrix passes the second state variable to the first, the third to the second and so on as the longitudinal position of the beam changes with respect to bending span position. In one form, the last state variable comes from an input white noise random process, also called "innovations process" (Kailath et al. 2000), and from previous state variables via coefficients in the last row of the state matrix. These coefficients come from a priori information developed from intuition, from other work, or from autocorrelation function estimates obtained by processing measured compliance values for a number of beams in a population of similar beams. Methods for obtaining autocorrelation estimates from measurements are known to those skilled in the art (Oppenheim and Schafer 1989).

The autocorrelation estimates can be used to compute coefficients in the state matrix based on known computational procedures (Papoulis 1991, Hayes 1996). Details are described herein.

The local compliance estimates obtained with a Kalman filter are optimal in the sense that the mean square estimation error is minimized. As part of the Kalman estimation process, the mean square error (variance) for each estimator is available. Derivation of the Kalman filter may be found in Kalman's original paper (Kalman 1960). An excellent reference (Kailath et al. 2000) puts the Kalman filter into context with other estimation procedures. Details of Kalman's derivation, are available from the inventor (Bechtel 2001).

Span Function and Output Weight Computation

An important part of the new method is the definition of weight coefficients used in the output equation of the system model. These coefficients come from a span function particular to each bending span. This specification discloses a procedure for determining span function for a general bending span. Descriptions of preferred and alternative embodiments illustrate generality of the procedure and provide details of span function computation for some bending spans commonly used in bending measurements of wood boards.

The approach for computing span function starts with beam equations developed from flexural loading considerations (Higdon et al. 1960), but without assuming that local compliance is constant. From the beam equations, a relationship is developed expressing measured compliance $C_m(w)$ at a measurement point w, as a functional of local compliance values along a beam. Then, a specific test function $C_t(u)$ is defined and used as the local compliance function. The test function $C_t(u)$ consists of a constant background compliance $C_o$ in addition to a compliance impulse (Dirac delta function) of weight "b" at position $\xi$. The distances u and $\xi$ are both measured from the leading end of the beam. $C_t(u)$ may be written:

$$C_t(u) = C_o + b\delta(u-\xi)$$

where $\delta$ is the Dirac delta function. With the test function as local compliance, the measured compliance functional is simplified to $C_m(b,x)$, which is a function of the impulse weight b and the distance $x=w-\xi$ from the measurement point location w to the impulse location $\xi$.

The span function h(x) at x is asserted to be the partial derivative of $C_m(b,x)$ with respect to b, evaluated at b=0, the derivative being assumed to exist.

$$h(x) = \left.\frac{\partial C_m(b,x)}{\partial b}\right|_{b=0}$$

The complete span function is obtained by carrying out the partial derivative computation for each x within the bending span. Thus, the computation is done for all impulse locations $\xi$ close enough to the measurement point w, to be within the bending span. The domain or extent of the bending span, may be defined as the neighborhood consisting of all x values for which the derivative defining h(x) is not zero; although the derivative may be zero at isolated points within the domain. In the development, it will be convenient in some cases to extend the domain of definition of the span function to include intervals over which the span function is zero, perhaps including the entire length of a beam.

Typically, the partial derivative is computed using the definition of derivative as a limit. Examples of the preferred and alternative embodiments show details.

If a bending span has span function h(x) defined over a domain between the first and last of n supports, the first at position $x_1$ and the last at position $x_n$, the convolution representation of Prior Art 2 may be used to write the measured beam compliance including measurement noise v(w) as:

$$C_m(w) = \int_{x_1}^{x_n} h(u)C(w-u)du + v(w), \text{ or}$$

$$C_m(k) = \sum_{j=p_1}^{p+p_1-1} b_{j-p_1+1}C(k-j) + v(k)$$

The notation $C_m(k)$, $C(k-j)$, and $v(k)$ indicate sampled values of their respective continuous functions for domain values at the integer multiples kd, (k-j)d, and kd respectively of the sampling increment d. The integral is a convolution integral, and it is replaced with a convolution sum, appropriate for use with sampled data. The sampling increment d replaces the differential element du, and d together with the number p of elements in the sum are chosen so that $pd=x_n-x_1$. Only minor difficulty is encountered in the preferred embodiment, where n=5, 6, or 7, and the extent of the bending span e.g. $x_7-x_1$ is not an integer multiple of the sampling increment d.

The indexing used in the convolution sum where the lower limit is $p_1$ allows flexibility in choice of bending span reference. The indexing on the weights $b_{j-p_1+1}$ runs from 1 to p for ease in coding. Usually, p>1 will be an odd integer and $p_1=-(p-1)/2$. This choice puts the span reference in the center of the bending span and aligns the measurement point with the part of the span where maximum contribution to measured compliance usually occurs, i.e. usually $b_{(p+1)/2}$ is the largest weight. For now, the weights $b_j$ may be considered as computed from the span function according to:

$$b_j = \int_{x_1+(j-1)d}^{x_1+jd} h(u)du \quad j=1,\ldots,p$$

The description of the preferred embodiment gives further details on the computation of weight coefficients from a span function. The sum of the weight coefficients agrees with the integral of h, and for proper calibration, the sum must be one. This can be seen from either the above convolution integral or convolution sum. If a constant local compliance $C_o$ is entered into either the convolution integral or the convolution sum, the measured compliance $C_m$ will be $C_o$ if the integral of h or the sum of the $b_j$ coefficients is one (neglecting measurement noise). The above relationships show the span function h(u) only as a function of the dummy variable u, and not of position w. Typically, h(u) is also a function of w, wherein the bending span and span function can change, depending on measurement point position w.

Dynamic System Model

A state-space representation of a dynamic system (Schwarz and Friedland 1965) for the beam compliance measurement process is introduced here. A vector equation (state equations):

$$s(k+1) = \phi(k)s(k) + U(k)$$

describes how the dynamic system evolves with increasing k.

The integer k identifies the measurement stage and also a measurement point on the beam. At the $k^{th}$ measurement point on a beam, the $k^{th}$ measurement stage or processing step occurs. However, measurement points do not extend out to beam ends. In bookkeeping used for the preferred embodiment, the first measurement of the beam is not identified by k=1; rather, as will be seen, the initial measurement point and hence measurement stage is identified as k=ki=12. This is to help identify the position of the measurement point relative to the leading end of the beam. The measurement point labeled k is a point at the center of the $k^{th}$ increment or element of length d from the leading end of the beam.

A (p, 1)-dimensional state vector s(k+1) for measurement stage k+1 is defined in terms of the (p, 1)-dimensional state vector s(k) and input vector U(k). The (p,p)-dimensional state matrix φ(k) describes how the state evolves from stage k to stage k+I in the absence of input.

As part of the state-space representation, an output equation gives the system output as a linear combination of the state variables, i.e. of the components of the state vector plus measurement noise:

$$y(k)=H(k)s(k)+v(k)$$

where H(k) is a (1,p)-dimensional output matrix. The output equation is similar to the previous convolution sum repeated here, but with $p_1=-(p-1)/2$:

$$C_m(k) = \sum_{j=(p-1)/2}^{(p-1)/2} b_{j+(p+1)/2} C(k-j) + v(k)$$

Local compliance values are identified with the state variables, and the measured compliance is identified with the output y(k) from the dynamic system. Thus, the dynamic system is used to model the beam local compliance and the compliance measurement. For example, the preferred embodiment uses state vector s(k), state matrix φ(k), input U(k) and output matrix H(k) given by:

$$s(k) = \begin{bmatrix} s_1(k) \\ s_2(k) \\ \vdots \\ s_{p-1}(k) \\ s_p(k) \end{bmatrix}, \phi = \begin{bmatrix} 0 & 1 & 0 & \cdots & 0 \\ 0 & 0 & 1 & \ddots & \vdots \\ \vdots & \vdots & \ddots & \ddots & 0 \\ 0 & 0 & \cdots & 0 & 1 \\ -a_p & -a_{p-1} & \cdots & -a_2 & -a_1 \end{bmatrix},$$

$$U(k) = \begin{bmatrix} 0 \\ 0 \\ \vdots \\ 0 \\ u(k) \end{bmatrix}$$

$$H(k) = [b_p \quad b_{p-1} \quad \cdots \quad b_2 \quad b_1].$$

In this case, the state matrix φ is independent of measurement stage k, although the Kalman filter does not require that. Because of the ones in the first upper diagonal of matrix φ, this state matrix translates state vector component values to their next lower indexed positions as k increases by one.

In the preferred embodiment, the output y(k) is one-dimensional, so the output matrix H(k) has only one row. Thus, at measurement stage k, the output y(k) is a scalar linear combination of the state variables plus measurement noise. If a second output, that is another measurement depending on the state, were available, a second row would be included in H(k). Then, the output y(k) would be a two-dimensional vector linear combination of the state variables plus a measurement noise vector.

Output matrix H(k) is written as a function of measurement stage k to indicate that it may change as a function of k, and it does change in the preferred embodiment because the bending span changes during the measurement of compliance for a beam.

For a system defined in this way, the state and output equations are in a form substantially the same as what has been labeled a "controllable canonical fomm" (Ogata 1987).

If the input u(k) is a white noise process, the output y(k) is an autoregressive moving average (ARMA) random process (Papoulis 1991; Hayes 1996).

The input white noise random process modified by its passage through the autoregressive part of the ARMA model, that is the state equations involving input noise, state variables and state matrix, is used to model local compliance. This makes local compliance an autoregressive random process. The (weighted) moving average part of the ARMA model shows the bending measurement as a convolution or moving average of local compliance values. A priori information about the beam local compliance random process is used to define the autoregressive parameters. A priori information about the bending span defines the moving average parameters. A Kalman filter is used to process the compliance measurements and obtain local compliance estimates by recognizing the equivalence in the model of local compliance with components of the state vectors as they evolve.

While there is great flexibility in modeling the local compliance function as an autoregressive random process as described, greater flexibility can be attained by introducing additional dimensionality to the model. For example, in a model having two parallel input branches, the first part involving correlations over relatively long distance is designed to model the characteristics of a wood board resulting from soil and climate conditions. A second part of the model is designed to represent knot structure with correlations over relatively short distances. Further generality can be introduced by modeling known noise disturbances so that part of the measurement may be assigned to the disturbances and not to the local compliance. In this specification, models including these deviations from the above state-space representation will also be referred to as being in the general category of ARMA models.

BRIEF DESCRIPTION OF THE DRAWINGS

FIG. 4 is a table showing bookkeeping details of the optimal estimation method for local compliance.

DETAILED DESCRIPTION OF THE PREFERRED EMBODIMENT

The preferred embodiment describes the new method as applied to the HCLT machine used for bending measurements of wood boards. After the preferred embodiment, alternative embodiments are described to illustrate the generality and some ramifications of the method. Finally, to illustrate some ramifications and applications of the new method, linear algebraic solution for local compliance is presented.

Figure 1:
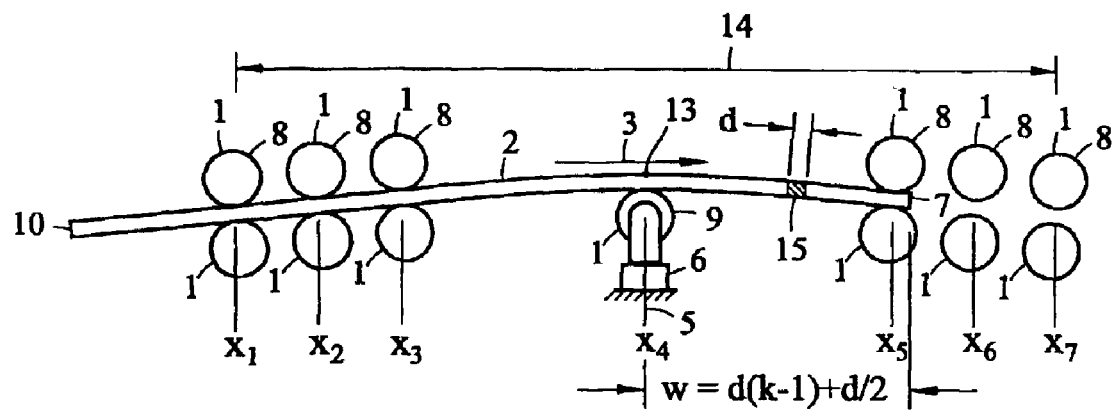
FIG. 1 (prior art) is a mechanical schematic representing a wood board moving relative to bending spans of an HCLT machine.

FIG. 1 illustrates the mechanical schematic of one of the two bending sections in an HCLT. The HCLT is a special case of the general framework of bending spans considered. The longitudinal direction is rightward and is substantially aligned with direction 3 of motion of wood board 2 as it progresses through the HCLT. Seven support points consist of rollers 1, which apply fixed vertical deflections $D_1, \ldots, D_7$, not labeled in FIG. 1, to wood board 2 at the seven support locations $x_1, \ldots, x_7$ respectively. These support locations are measured rightward from a selected longitudinal reference location 5. It is convenient to define reference 5 longitudinally at the center of the bending section, i.e. at position $x_4$ in FIG. 1.

Deflection of the wood board is substantially in the vertical plane and, as shown in FIG. 1, is greatly exaggerated. The vertical forces $F_1, \ldots, F_7$, not illustrated in FIG. 1, are forces applied to the board at the support points $x_1, \ldots, x_7$, and result from the applied deflections. Deflections and forces are defined with positive sense being upward. In the HCLT, only the force at the fourth support point $x_4$ is measured, and it is measured by means of load roller 9 and load cell 6. The deflection reference is arbitrary, and a convenient reference is the deflection at the first support; so that $D_1=0$. The upper six rollers labeled 8 are motor driven, and provide motive force to move board 2 longitudinally in direction 3. In FIG. 1, wood board 2 is shown at a position where it has just engaged the fifth of the set of seven supports for the bending section. Leading end 7 and trailing end 10 of the board are labeled in FIG. 1.

A measurement point 13 is defined on board 2 to give a reference for which a measured compliance $C_m$ may be assigned. The measurement point 13 is located on board 2 at a point aligned longitudinally with reference 5. As board 2 moves in direction 3 relative to reference 5, measurement point 13 moves along the board in a direction opposite direction 3, but all the while remaining aligned with bending span reference 5.

Beam Equations

Figure 2:
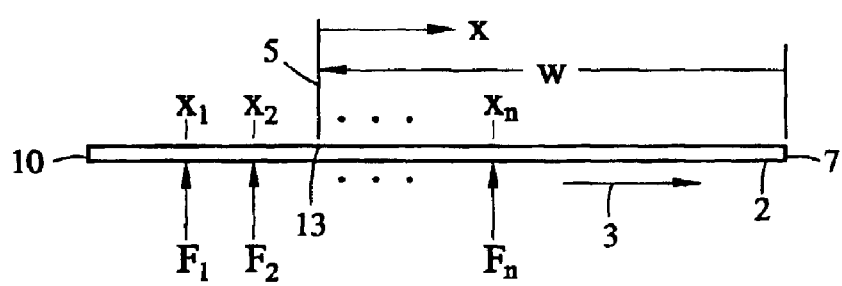
FIG. 2 illustrates the coordinate dimensioning system used in the longitudinal direction for the supports of a general bending span relative to a beam being tested by and moving with respect to the bending span.

Consider the general situation and refer to FIG. 2, where beam 2 is engaged by a bending span having n support points at locations $x_1, x_2, \ldots, X_n$. Each of these locations is defined relative to an arbitrarily selected longitudinal bending span reference location 5 of the bending span, the sense being positive to the right. Forces $F_1, F_2, \ldots, F_n$ applied at the support locations are illustrated in FIG. 2. The beam deflections (not shown) at these support points are in the vertical direction and denoted $D_1, D_2, \ldots, D_n$. The deflections can be referenced from any horizontal plane, but typically are referenced from a horizontal plane coinciding with the neutral surface of beam 2 at the first support at $x_1$ so that $D_1=0$. All forces and deflections follow the sense convention of being positive upward.

From equations for flexural loading of beams (Higdon et al. 1960) but with local compliance being variable and no distributed loads, it may be shown that n−1 beam deflections $D_2, \ldots, D_n$ at support locations $x_2, \ldots, x_n$ can be written:

$$D_j = D_1 + S_1(x_j - x_1) + M_- \int_{x_1}^{x_j} C(w-x)(x_j - x) dx +$$

$$V_- \int_{x_1}^{x_j} C(w-x)(x_j - x)(x - x_1) dx +$$

$$\sum_{i=1}^{j-1} F_i \int_{x_i}^{x_j} C(w-x)(x_j - x)(x - x_i) dx$$

$$= D_1 + S_1(x_j - x_1) + M_- J_{1j}(w) + \sum_{i=1}^{j-1} F_i I_{ij}(w)$$

for $j = 2, \ldots, n$.

In these equations, $C(w-x)=1/(E(w-x)(w-x))$ is the local compliance at point w−x on beam 2 measured leftward from its leading end 7. Referring to FIG. 2, the leading end 7 is located at distance w to the right of reference 5. Measurement point 13 on beam 2 is aligned with reference 5. The dummy variable of integration x is measured rightward from reference 5 to identify the point w−x on the beam. $S_1$ is the slope of the beam at the first support position $x_1$, and $M\_$ and $V\_$ are the moment and shear respectively in the beam just to the left of the first support at position $x_1$. The symbols $J_{tj}$, $I_{ij}$ and $I_{ij}$ are shorthand for the integrals indicated. Explicitly they are defined by:

$$J_{1j}(w) = \int_{x_1}^{x_j} C(w-x)(x_j-x)dx$$

$$I_{ij}(w) = \int_{x_i}^{x_j} C(w-x)(x_j-x)(x-x_i)dx; \; I_{1j}(w) = I_{ij}(w)|_{i=1}$$

These shorthand definitions show the dependence of $J_{ij}$ and $I_{ij}$ on w, their functional dependence on the local compliance function C being omitted from the notation. Clearly, $I_{ij}$ and $J_{ij}$ are functionals of the local compliance function C.

Further simplifying the notation by omitting w, adding two additional equations for translational and rotational equilibrium, and rearranging terms, gives the following n+1 beam equations:

$$I_{12}F_1+S_1(x_2-x_2)=D_2-D_1-I_{12}V_--J_{12}M_-$$

$$I_{13}F_1+I_{23}F_2+S_1(x_3-X_1)=D_3-D_1-I_{13}V_--J_{13}M_-$$

•

•

•

$$I_{1n}F_1+I_{2n}F_2+\ldots+I_{n-1,n}F_{n-1}S_1(x_n-x_1)=D_n-D_1-I_{1n}V_--J_{1n}M_-$$

$$F_1+F_2+\ldots+F_{n-1}+F_n=-(V_-+V_+)$$

$$(x_n-x_1)F_1+(x_n-X_2)F_2+\ldots+(x_n-x_{n-1})F_{n-1}=-(x_n-x_1)V_--(M_-+M_+)$$

$V_+$ and $M_+$ are shear and moment just to the right of the last support at $x_n$.

Explicitly, the steps for obtaining span function are:

Obtain an expression for measured compliance as a functional of the local compliance function;

Let the local compliance function be a test function having constant background compliance and a compliance impulse as previously described, and reduce the measured compliance functional to a measured compliance function of impulse weight and position.

Compute span function as the partial derivative of the measured compliance function with respect to impulse weight at impulse weight equal to zero. The expression for measured compliance may be obtained from the above n+1 equations. In matrix notation, they are: WA=B, with the definitions:

$$W = \begin{bmatrix} I_{12} & 0 & \ldots & 0 & 0 & x_2-x_1 \\ I_{13} & I_{23} & \ddots & 0 & 0 & x_3-x_1 \\ \vdots & \vdots & \ddots & \ddots & \vdots & \vdots \\ I_{1n} & I_{2,n} & \ldots & I_{n-1,n} & 0 & x_n-x_1 \\ 1 & 1 & \ldots & 1 & 1 & 0 \\ x_n-x_1 & x_n-x_2 & \ldots & x_n-x_{n-1} & 0 & 0 \end{bmatrix}, \; A = \begin{bmatrix} F_1 \\ F_2 \\ \vdots \\ F_{n-1} \\ F_n \\ S_1 \end{bmatrix}$$

$$B = \begin{bmatrix} D_2 \\ D_3 \\ \vdots \\ D_n \\ 0 \\ 0 \end{bmatrix} - \begin{bmatrix} 1 \\ 1 \\ \vdots \\ 1 \\ 0 \\ 0 \end{bmatrix} D_1 - \begin{bmatrix} I_{12} \\ I_{13} \\ \vdots \\ I_{1n} \\ 1 \\ (x_n-x_1) \end{bmatrix} V_- - \begin{bmatrix} J_{12} \\ J_{13} \\ \vdots \\ J_{1n} \\ 0 \\ 1 \end{bmatrix} M_- - \begin{bmatrix} 0 \\ 0 \\ \vdots \\ 0 \\ 1 \\ 0 \end{bmatrix} V_+ - \begin{bmatrix} 0 \\ 0 \\ \vdots \\ 0 \\ 0 \\ 1 \end{bmatrix} M_+$$

Vector B has been broken into several constituent vectors because for the preferred and alternative embodiments, all except the first are set to zero. Assuming W has an inverse, and retaining only the first of the constituents of B, the solution for A is:

$$A=W^{-1}B, \; B=[D_2 \; D_3 \; \ldots \; D_n \; 0 \; 0]^T$$

The superscript $^T$ indicates transpose. It has been explained that $D_1=0$ is an acceptable choice for an arbitrary deflection reference. Setting the boundary values of shear and moment to zero is reasonable or can be made reasonable by defining additional supports in the bending span to reduce effects caused by external forces. The equations can be used to determine what these effects are. This result will be used to develop the expression for measured compliance for the HCLT.

Span Functions for the Preferred Embodiment–HCLT

The five span functions considered correspond to five different bending spans that are sequentially applicable in the HCLT machine when it is restricted to testing wood boards longer than 80 inch.

FIG. 1 shows geometry of the second of two bending sections in the HCLT. This bending section has seven support points. Reference 5 for each of the five bending span configurations considered for this bending section is chosen to be aligned with the support at $x_4$. This support is in the center of the bending span when all seven support points are engaged. The seven supports are located at $x_1=-40$, $x_2=-32$, $x_3=-24$, $x_4=0$, $X_5=24$, $x_6=32$, and $x_7=40$ inches relative to reference 5.

FIG. 1 is considered to represent both bending sections of the HCLT because the force signal from the first section, properly delayed, is averaged with that from the second to give an average measurement. The average may be used to compute measured compliance $C_m$ that is compensated for bow in the board. When properly aligned, the geometries of the two bending sections are identical except that the second is an upside down version of the first.

In FIG. 1, board 2 is shown in the bending section and moving to the right with leading end 7 having just engaged the fifth support at $x_5$. This condition defines the first bending span for which useful measurement data are obtained. The bending span covers the domain between $x_1$ and $x_5$. The applicable span function is denoted $h_1$. As board 2 progresses to the right in FIG. 1, leading end 7 engages the additional support at $x_6$. The span function for this bending span having six support points is denoted $h_2$. Then, successively, seven, six and five supports are engaged with span functions $h_3$, $h_4$, and $b_5$ being applicable respectively as the board progresses through the bending section. Usually boards shorter than 80 inches are not processed by the HCLT. However, if it is desired to test shorter boards, additional span functions appropriate for the bending spans encountered may be defined, computed, and used in a similar way.

Output matrix H(k) is dependent on the measurement stage k. That is, H(k) depends on the measurement point location on the board because that determines the bending span being used. For the preferred embodiment, output matrix H(k) can take on one of five sets of values denoted H1, H2, H3, H4, or H5 corresponding respectively to the bending span and span functions $h_1$, $h_2$, $h_3$, $h_4$, and $h_5$.

Referring to FIG. 1 for the HCLT, force at the fourth support point at $X_4$, namely $F_4$, is measured through support roller 9 by load cell 6. Measured compliance $C_m(w)$ is given by:

$$C_m(w) = \frac{K_D}{F_4}$$

$C_m(w)$ is the expression for measured compliance from which span function will be computed. It is a functional of C, being dependent on the local compliance function C through the force $F_4$. $C_m(w)$ is inversely proportional to $F_4$ and is proportional to a calibration factor $K_D$ that depends on the bending span support point deflections, represented here by subscript D. The details showing the analytical development of this calibration factor are not trivial, but they are not necessary for the present discussion.

In operation, the deflections $D_j$ of the HCLT supports are fixed. Assuming rigidity at each of the support contacts with the wood board, calibration factor $K_D$ may be adjusted for each of the five bending span configurations so that a board having constant compliance $C_o$ will have measurement $C_m(w)=C_o$. This can serve as a defining relationship for $K_D$. That is:

$$K_D = C_o F_4$$

The design of the HCLT defines the support deflections $D_j$ so that $K_D$ does not depend on which of the five bending spans is applicable. However, this intended design condition is difficult to achieve in practice.

To obtain better accuracy of measurement, five calibration factors should be defined, K1, K2, K3, K4, and K5, which can be used in direct correspondence with the five bending spans. Then, calibration factor K1 and output matrix H1 would be used when the supports at $x_1, \ldots, x_5$ define the bending span. Calibration factor K2 and output matrix H2 would be used when the supports at $x_1, \ldots, x_6$ define the bending span, and so on. The fact that calibration factors unique to each bending span can be used to correct for machine misalignment has not been recognized by the manufacturer or users of the equipment. Present calibration method allows just one calibration factor K3, which is appropriate for spans defined with all seven supports and span function $h_3$ and depends on machine alignment for proper calibration when other spans are used. In practice, gross misalignment has been observed in equipment that is in service. Misalignment together with present practice using only one calibration factor causes preventable errors in measurements near the ends of a board.

Details showing how support deflections affect the calibration constant and how non-rigid support conditions may be accounted for in span function computation may be found in a document available from the inventor (Bechtel 2002). Other details of calibration, and their effects on the measurement are discussed at greater length in that same document, which is included as part of this specification by reference. The effects of support deflections on calibration factor and the effect of calibration with aluminum bars but testing with wood boards are also described therein. Span function computation examples are presented there for non-rigid support conditions.

Referring to FIG. 1, assume that wood board 2 has advanced so that its leading end 7 is just to the right of the seventh support at $x_7$ instead of just to the right of $x_5$ as shown. The span function $h_3$ for that case where all seven supports are engaged is computed first.

If local compliance of a beam is the constant value $C_o$, the matrix W is denoted $W_o$ and, after computation of the component integrals, is given by:

$$W_o = \begin{bmatrix} C_o(x_2-x_1)^3/6 & 0 & \ldots & 0 & 0 & x_2-x_1 \\ C_o(x_3-x_1)^3/6 & C_o(x_3-x_2)^3/6 & \ddots & \vdots & \vdots & x_3-x_1 \\ \vdots & \vdots & \ddots & 0 & 0 & \vdots \\ C_o(x_7-x_1)^3/6 & C_o(x_7-x_2)^3/6 & \ldots & C_o(x_7-x_6)^3/6 & 0 & x_7-x_1 \\ 1 & 1 & \ldots & 1 & 1 & 0 \\ x_7-x_1 & x_7-x_2 & \ldots & x_7-x_6 & 0 & 0 \end{bmatrix}$$

Using available information about the support locations and deflections, the following nominal values are applicable:

$$\begin{bmatrix} x_1 \\ x_2 \\ x_3 \\ x_4 \\ x_5 \\ x_6 \\ x_7 \end{bmatrix} = \begin{bmatrix} -40 \\ -32 \\ -24 \\ 0 \\ 24 \\ 32 \\ 40 \end{bmatrix}, B = \begin{bmatrix} D_2 \\ D_3 \\ D_4 \\ D_5 \\ D_6 \\ D_7 \\ 0 \\ 0 \end{bmatrix} = \begin{bmatrix} 0.15625 \\ 0.3125 \\ 0.625 \\ 0.3125 \\ 0.15625 \\ 0 \\ 0 \\ 0 \end{bmatrix}$$

where units are inches. Using $C_{mo}$ to denote the measurement when local compliance is the constant value $C_o$, it may be written:

$$C_{mo} = \frac{K3}{F_4} = \frac{K3}{\{A\}_4} = \frac{K3}{\{W_o^{-1}B\}_4} = C_o$$

The subscripted brace notation $\{\ \}_4$ indicates the fourth component of the enclosed vector. K3 is defined as the calibration factor $K3=K_D$ specifically to give a measured compliance of $C_{mo}=C_o$ when a beam of constant local compliance $C_o$ is measured. From the development of measured compliance as a convolution of the local compliance function with the span function, this is the some as requiring the integral of the span function $h_3(x)$ to be one. In the discrete sampled data case, it is equivalent to requiring the sum of the coefficients in the output matrix H3 to be one.

Now, let the beam local compliance be the test function $C_t(u)$, which has a compliance impulse with weight b at position $\xi$ superimposed on a constant background compliance $C_o$:

$$C(u)\ C_t(u)=C_o+b\delta(u-\xi)$$

The position $\xi$ is measured from the leading end of the beam. The integral $I_{ij}(w)$ from the general matrix W can be written:

$$I_{ij}(w) = \int_{x_i}^{x_j} C_t(w-t)(x_j-t)(t-x_i)dt$$

$$= \int_{x_i}^{x_j} (C_0 + b\delta(w-t-\xi))(x_j-t)(t-x_i)dt$$

-continued $$= \begin{cases} C_0 \frac{(x_j - x_i)^3}{6} + b(x_j - x)(x - x_i), & \text{if } x_i < x \leq x_j \\ C_0 \frac{(x_j - x_i)^3}{6}, & \text{otherwise} \end{cases} \quad 5$$

The variable $x = w - \xi$ identifies the position of the impulse relative to reference 5 of FIG. 1 or 2. Applying this computation to each $I_{ij}$ entry, matrix W can be broken into the sum of two matrices:

$$W = W_o + bW_d(x)$$

Matrix $W_d(x)$ is:

$$W_d(x) = \begin{bmatrix} d_{12}(x) & 0 & 0 & \cdots & 0 & 0 & 0 \\ d_{13}(x) & d_{23}(x) & 0 & \cdots & 0 & 0 & 0 \\ d_{14}(x) & d_{24}(x) & d_{34}(x) & \ddots & \vdots & 0 & 0 \\ \vdots & \vdots & \vdots & \ddots & 0 & \vdots & \vdots \\ d_{17}(x) & d_{27}(x) & d_{37}(x) & \cdots & d_{6,7}(x) & 0 & 0 \\ 0 & 0 & 0 & \cdots & 0 & 0 & 0 \\ 0 & 0 & 0 & \cdots & 0 & 0 & 0 \end{bmatrix}$$

and $d_{ij}(x)$ is defined by:

$$d_{ij}(x) = \begin{cases} (x_j - x)(x - x_i), & \text{if } x_i < x \leq x_j \\ 0, & \text{otherwise} \end{cases}$$

For example, if x happens to be located between the second and third supports:

$$W_d(x) = \begin{bmatrix} 0 & 0 & 0 & \cdots & 0 \\ (x_3 - x)(x - x_1) & (x_3 - x)(x - x_2) & 0 & \cdots & 0 \\ (x_4 - x)(x - x_1) & (x_4 - x)(x - x_2) & 0 & \cdots & 0 \\ \vdots & \vdots & \vdots & \ddots & \vdots \\ (x_7 - x)(x - x_1) & (x_7 - x)(x - x_2) & 0 & \cdots & 0 \\ 0 & 0 & 0 & \cdots & 0 \\ 0 & 0 & 0 & \cdots & 0 \end{bmatrix}, x_2 < x \leq x_3$$

The expression for measured compliance $C_m(w)$ reduces to $C_m(b,x)$ when the local compliance function is the test function as follows:

$$C_m(b, x) = \frac{K3}{F_4} = \frac{K3}{\{W^{-1}\underline{B}\}_4} = \frac{K3}{\{(W_o + bW_d(x))^{-1}\underline{B}\}_4}$$

$$= \frac{K3}{\{(I_8 + bW_o^{-1}W_d(x))^{-1}W_o^{-1}\underline{B}\}_4}$$

where $I_8$ is an 8-dimensional identity matrix. The span function $h_3(x)$ is obtained as a partial derivative of $C_m(b,x)$ at $b=0$ according to:

$$h_3(x) = \frac{\partial C_m(b, x)}{\partial b}\bigg|_{b=0} = \lim_{b \to 0}\left[\frac{C_m(b, x) - C_{mo}}{b}\right]$$

$$= \lim_{b \to 0}\frac{1}{b}\left[\frac{K3}{\{(I_8 + bW_o^{-1}W_d(x))^{-1}W_o^{-1}\underline{B}\}_4} - \frac{K3}{\{W_o^{-1}\underline{B}\}_4}\right]$$

$$= \lim_{b \to 0}\frac{1}{b}\left[\frac{K3}{\{(I_8 - bW_o^{-1}W_d(x))W_o^{-1}\underline{B}\}_4} - \frac{K3}{\{W_o^{-1}\underline{B}\}_4}\right]$$

-continued $$= \lim_{b \to 0}\frac{1}{b}\left[\frac{K3}{\{W_o^{-1}\underline{B}\}_4}\left(\frac{1}{(1 - b\{W_o^{-1}W_d(x)W_o^{-1}\underline{B}\}_4/\{W_o^{-1}\underline{B}\}_4)} - 1\right)\right]$$

$$= \lim_{b \to 0}\frac{1}{b}\left[C_o\left(1 + b\frac{\{W_o^{-1}W_d(x)W_o^{-1}\underline{B}\}_4}{\{W_o^{-1}\underline{B}\}_4} - 1\right)\right]$$

$$= C_o \frac{\{W_o^{-1}W_d(x)W_o^{-1}\underline{B}\}_4}{\{W_o^{-1}\underline{B}\}_4}, x_1 < x \leq x_7$$

To carry out the indicated computations, a value of $C_o$ is entered. But, it is possible to avoid entering a value for $C_o$. By multiplying the second to last of the system of beam equations by $C_o$ so that the 1's in the $W_o$ matrix become $C_o$, it can be shown that the constant compliance $C_o$ cancels in the span function computation. This involves partitioning the $W_o$ matrix into four component matrices, only one having $C_o$ as a factor. The partitioned inverse of $W_o$ will have a component matrix with $C_o$ appearing only as the multiplier $1/C_o$. This component matrix is the only one needed in the computation of span function because of the zeros in vector a and matrix $W_d(x)$ and the need for only the fourth component in the numerator and denominator of the above expression for $h_3(x)$. Because the inverse matrix $W_o^{-1}$ appears as a factor twice in the numerator of the expression for $h_3(x)$ and once in the denominator, all factors of $C_o$ cancel in the computation. These details can be used to write a form of the span function, which allows it to be computed without use of $C_o$.

However, the result as stated with $C_o$ is simple to write and to compute. Use of a value for $C_o$ in the computations is not seen as a detriment. The value chosen is not critical; it must only be in a reasonable dynamic range to not cause numerical error in computation. It is recommended to select a value within a factor of 100 or so of compliance values expected for the beams to be tested. For example, in a 2×4 wood board having cross-sectional dimensions of 1.5 inch by 3.5 inch, the product EI will be within an order of magnitude of $2 \times 10^6$ lb in$^2$. Hence, the choice $C_o = 0.5 \times 10^{-6}$ (lb in$^2$) is satisfactory.

Samples of the span function $h_3(x)$ can be computed according to the above formula by allowing x to take on values between $x_1$ and $x_7$. The incremental spacing between the x samples is a matter of choice. However, for local compliance estimation, the weight coefficients in the dynamic system output matrix are based on integrals of $h_3(x)$ over incremental domains having length equal to the sample spacing d for measured compliance. To accurately obtain these integrals numerically, setting the increment for computing span function equal to d/10 is adequate.

Dependence of output matrix H(k) on k for the preferred embodiment is dependence on the bending span. The output matrix remains constant over each measurement stage k having a specific bending span. To make this clear, the notation is changed from H(k) to H3 where the 3 indicates that this is the third in the sequence of five output matrices and is to be used for all measurement stages k for which the bending span is defined with all seven supports being active. The notation H3(O) indicates the $j^{th}$ component in the matrix H3. Thus, H3 is given by:

$$H3 = [H3(1) \quad H3(2) \quad \cdots \quad H3(p-1) \quad H3(p)]$$

$$= [b_p \quad b_{p-1} \quad \cdots \quad b_2 \quad b_1]$$

The indexing of the output matrix weights $b_p, \ldots, b_n$, in each output matrix H(k) of the system model, e.g. in H3, is reversed from the natural ordering. This is a consequence of the convolution of the span function with the local compliance function and the oppositely directed arguments of these two functions as expressed in the convolution integral.

Summarizing, the HCLT span function $h_3(x)$ is derived for the bending span where all seven supports are active, and the p weight coefficients developed from it are put into the single row output matrix H3.

Referring to FIG. 1, wood board 2 enters the bending section from the left, and measured compliance data are accepted after leading end 7 reaches the fifth support at $x_5$. This is the condition shown in FIG. 1. From there until leading end 7 reaches the sixth support at $x_6$, a span function with the five support points at positions $x_1$, $X_2$, $X_3$, $x_4$, and $x_5$ is applicable. This span function is denoted $h_1(x)$ and the weight coefficients developed from it become the entries of output matrix H1. In this case, n=5 and there are only n+1=6 equations in the system of equations instead of eight as used for the computation of $h_3(x)$. With the same incremental sample spacing as for the computation of output matrix H3, there will be fewer components of H1 than for H3. It is possible to have a variable length state vector. However, the bookkeeping is simpler if all five output matrices H1, H2, H3, H4, and H5 are the same size, and the length of the state vector (number of state variables) remains constant.

Consequently, the interval domain of definition $x_1$ to $X_5$ for the span function $h_1(x)$ is extended to the interval $x_1$ to $X_7$. The span function $H_1(x)$ is defined to be zero for $x_5 < x \leq x_7$, which represents that part of the bending section not covered by a board with local compliance contributing to compliance measurements. The output matrix H1 is defined to be the same size as H3, and the first few entries of H1, developed from samples of the span function for domain between $x_7$ and $x_5$, are zero. The backwards ordering of the matrix H1 entries from the span function causes the first entry to come from that part of the span function near $x_7$. The result is:

$$H1 = [H1(1) \quad H1(2) \quad \cdots \quad H1(p-1) \quad H1(p)]$$
$$= [b_p \quad b_{p-1} \quad \cdots \quad b_2 \quad b_1]$$

The $b_j$ coefficients are used in the output matrix H1 as they were in H3. The coefficients $b_j$ are used generically to take on values applicable to the bending span at the moment; whereas, H1, ..., H5 each represent a specific bending span.

Support location and deflection entries for computation of $h_1(x)$ are:

$$\begin{bmatrix} x_1 \\ x_2 \\ x_3 \\ x_4 \\ x_5 \end{bmatrix} = \begin{bmatrix} -40 \\ -32 \\ -24 \\ 0 \\ 24 \end{bmatrix}, B = \begin{bmatrix} D_2 \\ D_3 \\ D_4 \\ D_5 \\ 0 \\ 0 \end{bmatrix} = \begin{bmatrix} 0.15625 \\ 0.3125 \\ 0.625 \\ 0.3125 \\ 0 \\ 0 \end{bmatrix}$$

The span function $h_1$ is computed from:

$$h_1(x) = \begin{cases} C_o \dfrac{\{W_o^{-1} W_d(x) W_o^{-1} B\}_4}{\{W_o^{-1} B\}_4}, & x_1 < x \leq x_5 \\ 0, & x_5 < x \leq x_7 \end{cases}$$

where the $W_o$ and $W_d$ matrices have been reduced in dimensionality to 6×6 matrices by removing rows 5 and 6 and columns 5 and 6 from the previous definitions. In the last row of W., the support position designation $x_7$ is replaced with $X_5$.

Similarly, the span function $h_2(x)$ and output matrix H2 are computed for the six support bending span when in FIG. 1, leading end 7 of wood board 2 is between the sixth and seventh supports, i.e. between $x_6$ and $x_7$. Then, the $W_o$ and $W_d$ matrices are 7×7 dimensional. The span function $h_2(x)$ is:

$$h_2(x) = \begin{cases} C_o \dfrac{\{W_o^{-1} W_d(x) W_o^{-1} B\}_4}{\{W_o^{-1} B\}_4}, & x_1 < x \leq x_6 \\ 0, & x_6 < x \leq x_7 \end{cases}$$

After the leading end of the board passes the support at $x_7$ and while the support at $x_1$ remains engaged, the span function $h_3(x)$ and output matrix H3 previously described are applicable.

In FIG. 1, after trailing end 10 of board 2 uncovers the support at $x_1$ and while it is between $x_1$ and $x_2$, span function $h_4(x)$ and output matrix H4 are used. Rather than renumbering the supports, consider that the first support is no longer in the span, and start with the second support at $x_2$. For this bending span, $W_o$ and $W_d$ are 7×7 dimensional and are:

$$W_o =$$

$$\begin{bmatrix} C_o(x_3-x_2)^3/6 & 0 & \cdots & 0 & 0 & x_3-x_2 \\ C_o(x_4-x_2)^3/6 & C_o(x_4-x_3)^3/6 & \ddots & \vdots & \vdots & x_4-x_2 \\ \vdots & \vdots & \ddots & 0 & 0 & \vdots \\ C_o(x_7-x_2)^3/6 & C_o(x_7-x_3)^3/6 & \cdots & C_o(x_7-x_6)^3/6 & 0 & x_7-x_2 \\ 1 & 1 & \cdots & 1 & 1 & 0 \\ x_7-x_2 & x_7-x_3 & \cdots & x_7-x_6 & 0 & 0 \end{bmatrix}$$

$$W_d(x) = \begin{bmatrix} d_{23}(x) & 0 & 0 & 0 & 0 & 0 & 0 \\ d_{24}(x) & d_{34}(x) & 0 & 0 & 0 & 0 & 0 \\ d_{25}(x) & d_{35}(x) & d_{45}(x) & 0 & 0 & 0 & 0 \\ d_{26}(x) & d_{36}(x) & d_{46}(x) & d_{56}(x) & 0 & 0 & 0 \\ d_{27}(x) & d_{37}(x) & d_{47}(x) & d_{57}(x) & d_{67}(x) & 0 & 0 \\ 0 & 0 & 0 & 0 & 0 & 0 & 0 \\ 0 & 0 & 0 & 0 & 0 & 0 & 0 \end{bmatrix}$$

The support positions and support deflections are given by:

$$\begin{bmatrix} x_2 \\ x_3 \\ x_4 \\ x_5 \\ x_6 \\ x_7 \end{bmatrix} = \begin{bmatrix} -32 \\ -24 \\ 0 \\ 24 \\ 32 \\ 40 \end{bmatrix}, B = \begin{bmatrix} D_3 \\ D_4 \\ D_5 \\ D_6 \\ D_7 \\ 0 \\ 0 \end{bmatrix} = \begin{bmatrix} 0.15625 \\ 0.46875 \\ 0.15625 \\ 0 \\ -0.15625 \\ 0 \\ 0 \end{bmatrix}$$

The units are in inches. Deflections are referenced to $D_2$ because the support at $x_2$ is treated as the beginning of the bending span. The span function $h_4(x)$ is:

$$h_4(x) = \begin{cases} C_o \dfrac{\{W_o^{-1} W_d(x) W_o^{-1} B\}_3}{\{W_o^{-1} B\}_3}, & x_2 < x \leq x_7 \\ 0, & x_1 < x \leq x_2 \end{cases}$$

The third components of vectors enclosed by braces { } are selected because measured force $F_4$ is now the third vector component. Output matrix H4 has zeros in its high index positions corresponding to samples of $h_4(x)$ in the domain between $x_1$ and $x_2$.

In FIG. 1, after trailing end 10 of board 2 passes the support at $x_2$ and while it is between $x_2$ and $x_3$, span function $h_5$ and output matrix H5 are used. Span function $h_5(x)$ is:

$$h_5(x) = \begin{cases} C_o \dfrac{\{W_o^{-1} W_d(x) W_o^{-1} B\}_2}{\{W_o^{-1} B\}_2}, & x_3 < x \leq x_7 \\ 0, & x_1 < x \leq x_3 \end{cases}$$

The 6×6 dimensional matrices $W_o$ and $W_d$ are given by:

$$W_o = \begin{bmatrix} C_o(x_4-x_3)^3/6 & 0 & 0 & 0 & 0 & x_4-x_3 \\ C_o(x_5-x_3)^3/6 & C_o(x_5-x_4)^3/6 & 0 & 0 & 0 & x_5-x_3 \\ C_o(x_6-x_3)^3/6 & C_o(x_6-x_4)^3/6 & C_o(x_6-x_5)^3/6 & 0 & 0 & x_6-x_3 \\ C_o(x_7-x_3)^3/6 & C_o(x_7-x_4)^3/6 & C_o(x_7-x_5)^3/6 & C_o(x_7-x_6)^3/6 & 0 & x_7-x_3 \\ 1 & 1 & 1 & 1 & 1 & 0 \\ x_7-x_3 & x_7-x_4 & x_7-x_5 & x_7-x_6 & 0 & 0 \end{bmatrix}$$

$$W_d(x) = \begin{bmatrix} d_{34}(x) & 0 & 0 & 0 & 0 & 0 \\ d_{35}(x) & d_{45}(x) & 0 & 0 & 0 & 0 \\ d_{36}(x) & d_{46}(x) & d_{56}(x) & 0 & 0 & 0 \\ d_{37}(x) & d_{47}(x) & d_{57}(x) & d_{67}(x) & 0 & 0 \\ 0 & 0 & 0 & 0 & 0 & 0 \\ 0 & 0 & 0 & 0 & 0 & 0 \end{bmatrix}$$

Support positions and support deflections are:

$$\begin{bmatrix} x_3 \\ x_4 \\ x_5 \\ x_6 \\ x_7 \end{bmatrix} = \begin{bmatrix} -24 \\ 0 \\ 24 \\ 32 \\ 40 \end{bmatrix}, \quad B = \begin{bmatrix} D_4 \\ D_5 \\ D_6 \\ D_7 \\ 0 \\ 0 \end{bmatrix} = \begin{bmatrix} 0.3125 \\ 0 \\ -0.15625 \\ -0.3125 \\ 0 \\ 0 \end{bmatrix}$$

the numbers being in inches. Deflections are referenced to $D_3$. Output matrix H5 has zeros in its high index positions corresponding to $h_5(x)$ for x in the domain between $x_1$ and $x_3$.

Figure 3:
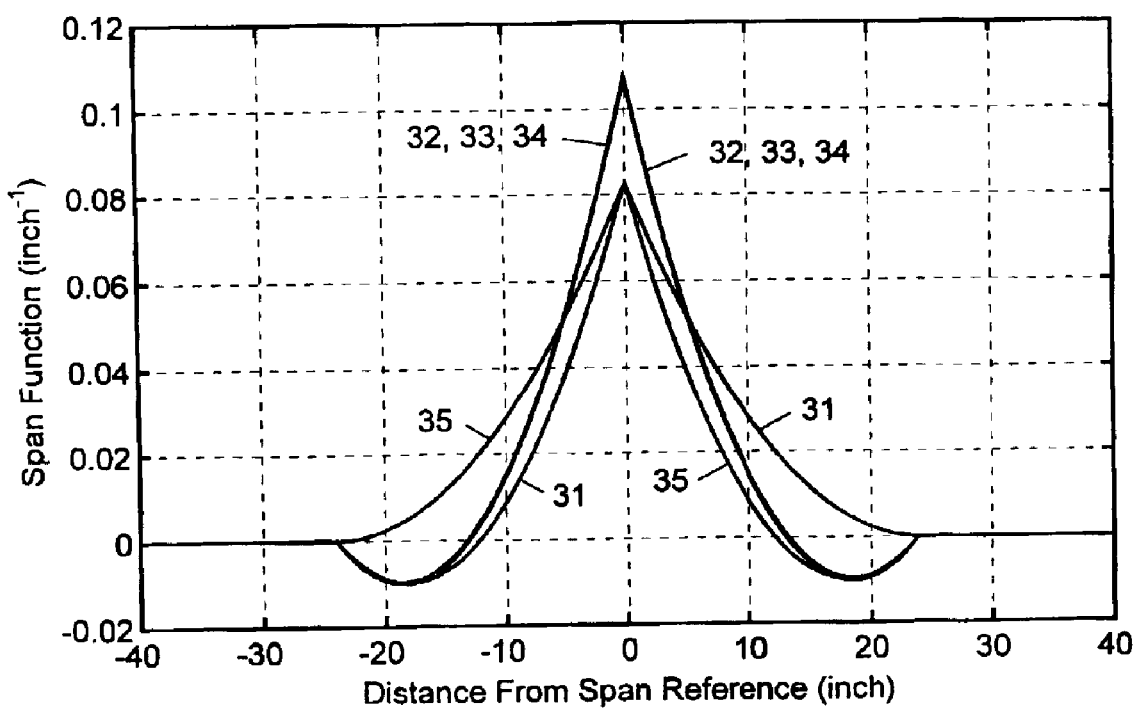
FIG. 3 graphs the five span functions applicable for a perfectly aligned HCLT with rigid supports when wood boards longer than 80 inches are tested in it; only three distinct span functions are apparent from the scale of the graph.

The five span functions $h_1(x), \ldots, h_5(x)$ for the HCLT are plotted in FIG. 3 and labeled 31, 32, 33, 34, and 35 respectively. They are idealized versions computed with assumption of rigid supports and perfectly aligned support positions and deflections. Details of computations where conditions are not ideal and where there are differences between wood board support rigidity and aluminum calibration bar support rigidity are contained in (Bechtel 2002). In FIG. 3, the functions $h_2$, $h_3$, and $h_4$ (32, 33, 34) are almost identical and do not show a difference on the scale of the plot because rigid supports and perfect alignment of the support deflections have been assumed. The curves $h_1$ and $h_5$ (31 and 35) show clearly the difference between span ends that are simply-supported and those that are multiply-supported. Differences in the functions $h_2$, $h_3$, and $h_4$ are more pronounced when supports are not perfectly rigid and when support deflections are not perfectly adjusted. For perfect conditions and perfect alignment, all five of these span functions are zero on the domain outside the interval ($x_3$, $x_5$)=(−24, 24) inch. This is by design of HCLT bending spans because perfect alignment of the seven HCLT support deflections and rigid support conditions cause a condition of zero moment outside that interval in a board having constant local compliance within the interval. Deflection misalignment or deviation from support point rigidity will cause the span functions to be different from zero for regions of the domain outside this central interval.

Measured Versus Computed Span Function

One can approximate the derivative and hence span function with sensitive compliance measurements of a beam with and without a compliance impulse. Rather than dividing by the impulse weight, which may be difficult to determine, the difference function is normalized by dividing by the sum of the differences (assuming sampled data).

To determine the span function by measurement, a constant compliance straight beam with impulse superimposed is moved through the bending span and compliance measured for a sequence of impulse positions relative to bending span reference 5 in FIG. 1. Then, compliance is measured for another straight beam having the same constant compliance, but no impulse, or for the same beam with a constant compliance length segment of it covering the bending span. The measured compliance without impulse is subtracted from the sequence of measurements with impulse. The difference sequence divided by the sum of the differences approximates the span function. In the HCLT, the span function $h_3$ may be approximated in this way. To apply the approach to the other four HCLT span functions identified, a means must be provided to disengage selected supports. Else, the bending span configuration changes as the beam moves through the machine and engages different sets of supports. Alternatively, a sequence of straight beams all with identical constant background compliance $C_o$ and impulse weight b, but with impulse at progressively increasing positions from one end, could be used.

A compliance impulse at a point along a beam may be simulated by machining the beam in a neighborhood of the point, e.g. by drilling or cutting. The machining must be sufficient to cause an impulse weight large enough so the measured effect overcomes measurement noise, but the machining cannot affect the contact characteristics of the beam with the bending span supports. The impulse weight cannot be too large if the measured result is to approximate well the derivative and hence the span function. The quality of approximation can be tested by changing the weight of the impulse, either by more or by less machining, and comparing results. Approximation is good if negligible change in result occurs for change in impulse weight below some threshold. The test of quality of approximation can also be tested analytically, but approximating the derivative as a normalized difference using various impulse weights without taking the limit of impulse weight going to zero. Because of measurement noise, it will be best to obtain span function by the computed approach. However, for situations where it is desirable to check the performance of an as-built (or, as aligned) bending span, the approach using measurements may be useful.

In principle, neither for the computed derivative nor for the approximated derivative from measurements is it necessary to use constant compliance in the test function as the background compliance. However, a constant compliance background is most practical. For the computed span function, use of a constant compliance background allows computations to be performed easily. For the case of measured compliance with an impulse on a background constant compliance beam, the beam and impulse may be moved through the span and compliance measurements made. If the background compliance were not constant, then some means must be provided to allow the impulse to move along the span, while the non-constant compliance background remains in place relative to the span.

Preprocessing of Measurement Data

In the HCLT, the sampling increment is 0.54664 inch. In this specification, the sampling increment is taken as d=2.1866 inch, representing a decimation of HCLT compliance measurement data by a factor of four. Study of the power spectrum of HCLT measurements indicates this decimation can be performed with negligible effect on data quality. Computations for the new method using non-optimized code and modest computer equipment have been proved possible at high production speeds with 2.1866-inch sample increments. Optimization of computer code and use of higher speed computing machinery may allow direct use of 0.54664-inch sample increments, although initial experience indicates this is unnecessary.

The available measurement data at 0.54664-inch sample increments is preprocessed by a filtering step to decimate by four and reduce aliasing from high frequency noise using well-known methods. For example, one of the decimate algorithms in code available from The Mathworks, Inc. in Natick Mass. can be used for this purpose.

Output Matrices

The output equation for the dynamic system model is:

$y(k)=H(k)s(k)+v(k)$

Entries in output row matrix H(k) are determined from the HCLT span function at measurement stage k. The state vector s(k) is placed in correspondence with local compliance values, and v(k) is measurement noise. The following description and the table of FIG. 4 will help make this correspondence clear for each measurement stage.

A wood board's local compliance is treated as samples of a continuous local compliance function with sample increments of d inch. The first sample is identified with the first d-inch increment at the board's leading end and may be considered to occur at a sample point d/2 inch from the leading end. In general, the $j^{th}$ sample is identified with the $j^{th}$ d-inch sample increment and may be considered to occur at a sample point d(j−1)+d/2 inch from the board's leading end. In FIG. 1, the $j^{th}$ sample increment could be, for example, the hatched increment labeled 15. The sample at a point is considered to represent the beam compliance over a d-inch long interval centered about the sample point.

Each measured compliance is identified with a measurement point on the board. As the board is moved longitudinally relative to span reference 5, measurement points are assumed to occur at the same d-inch sample increment spacing as for the local compliance samples. This assumption together with the regular subdivision of the board length for local compliance samples makes the bookkeeping simpler. However, measurement points are not defined near the board ends. This can be seen in FIG. 1, where leading end 7 of board 2 has just engaged the fifth support at $x_5$ and measurement point 13 is the closest one defined near leading end 7.

The initial measurement stage is labeled with k=ki, and for the HCLT, ki=12. Referring again to FIG. 1, the measurement stage can be identified with measurement point 13 on board 2 such that the measurement point is longitudinally aligned with bending span reference 5. The measurement point is at a distance w=d(k−1)+d/2 inch from leading end 7, or equivalently, leading end 7 has advanced by d(k−1)+d/2 inch past reference 5. When k=12 and d=2.1866 inch, w is 25.1459 inch. When reference 5 is chosen as being at support point $X_4$ as shown, then by definition $x_4=0$, and in the HCLT, $x_5=24$ inch. Measurement stage k=12 is the first measurement stage for which a sample increment is centered at reference 5 and board 2 engages the support at $x_5$. This is the first board position for which a measurement is taken. Numbers such as d=2.1866 and w=25.1459 are expressed in this description with 4-place precision to make sure it is understood where they come from. Such precision is typically unattainable in measurement equipment of this type.

In the convolution sum discussed earlier, a common mean value is subtracted from each side of the equation. Then the convolution sum $$C_m(k) = \sum_{j=-(p-1)/2}^{(p-1)/2} b_{j+(p+1)/2} C(k-j) + v(k) \text{ becomes}$$

$$c_m(k) = \sum_{j=-(p-1)/2}^{(p-1)/2} b_{j+(p+1)/2} c(k-j) + v(k)$$

where $c_m$ and c have zero mean.

For computational purposes it is convenient to identify samples of HCLT span functions, and hence output matrix entries in H(k) using the same sampling increment d=2.1866 inch as for local compliance definition and for compliance measurements. Putting a span function sample at reference 5, and samples at 2.1866 inch increments away from the reference requires a total of p=37 samples or sample increments to cover the extended domains for each of the five HCLT bending span functions. Rather than just sampling the continuous span functions, output matrix entries are identified as the integrals of the span functions over domains corresponding to their respective sample increments. Near the ends, that is for the $1^{st}$ and $37^{th}$ components of each of the output matrices, the entries are zero or nearly zero. The mid-point entry for each of these output matrices is maximum because the HCLT span functions are maximum at reference 5. Output matrices have dimensions (1,37) and the state vector has dimensions (37,1). Computations for output matrix coefficients in H1 are now described more fully. The fact that the supports are not spaced exactly at integer multiples of the sampling increment d can be handled simply because the span functions are zero for the short parts of sampling increments that overhang the bending spans.

Referring to FIG. 1, consider the first position for which leading end 7 of board 2 engages the support at $x_5$ with a sampling increment centered at reference 5. This occurs when leading end 7 is at 25.1459 inch relative to reference 5 or just past the support at $x_5$ by 1.1459 inch, and the $12^{th}$ sampling increment of the board is centered longitudinally at reference 5. But, the 19$^{th}$ sampling increment of the extended span function is at reference 5. From this condition, the weights H1(37)=$b_1$ through H1(1)=$b_{37}$ may be computed as:

$$HI(37) = b_1 = \int_{-40.4521}^{-40.4521+2.1866} h_1(x)dx = \int_{-40}^{-38.2655} h_1(x)dx,$$

because $h_1(x) = 0$ for $x < -40$ $$HI(36) = b_2 = \int_{-40.4521+2.1866}^{-40.4521+2(2.1866)} h_1(x)dx = \int_{-38.2655}^{-36.0789} h_1(x)dx$$

$$\vdots$$

$$HI(20) = b_{18} = \int_{-40.4521+17(2.1866)}^{-40.4521+18(2.1866)} h_1(x)dx = \int_{-3.2799}^{-1.0933} h_1(x)dx$$

$$HI(19) = b_{19} = \int_{-40.4521+18(2.1866)}^{-40.4521+19(2.1866)} h_1(x)dx = \int_{-1.0933}^{+1.0933} h_1(x)dx,$$

at bending span reference 5 in Fig. 1

$$\vdots$$

$$HI(8) = b_{30} = \int_{-40.4521+29(2.1866)}^{-40.4521+30(2.1866)} h_1(x)dx$$

$$= \int_{+22.9593}^{+25.1459} h_1(x)dx$$

$$= \int_{+22.9593}^{+24} h_1(x)dx,$$

because $h_1(x) = 0$ for $x > 24$ $$HI(7) = b_{31} = 0$$

$$\vdots$$

$$HI(1) = b_{37} = 0$$

Weight H1(8) corresponds to the span function weight for the increment of its domain between 22.9593 and 25.1459 inch, i.e. for the increment of the board most closely aligned with the support at $x_5$=24 inch. The span function $h_1(x)$ is zero for x>24 inch because, for this position of leading end 7, no support engages the board past x=24 inch (this is the part of the domain of $h_1$ that was extended with $_1(x)$=0). The output matrix H1 computed as above applies for measurement stages k=12, 13, 14, and 15, that is H(k)=H1 for these k values. They correspond respectively to leading end 7 of board 2 at positions d(k–1)+d/2=2.1866(k–0.5)=25.1459, 27.3325, 29.5191, and 31.7057 inch past reference 5 of the bending span.

For measurement stage k=16, leading end 7 has moved to 33.8923 inch past reference 5 and therefore the board engages the support at $x_6$=32 inch; hence output matrix H2 is applicable. Using $h_2$, and following a similar argument as for H1, components of H2 may be computed. H2 is applicable for measurement stages k=16, 17, and 18, for which leading end 7 is 33.8923, 36.0789, and 38.2655 inch respectively past reference 5. For k=19, leading end 7 is 40.4521 inch past reference 5. Because the board engages the support at $X_7$=40 inch, as well as the first six supports at $x_1, \ldots, X_6$, output matrix H3 is applicable. From $h_3$, the components of 133 are computed similarly to those for H1 and H2. H3 remains applicable for positions of board 2 until the first measurement stage for which trailing end 10 has cleared the first support at $x_1$=40 inch.

End 7 and end 10 positions may be tested either by keeping track of the HCLT photosensor outputs (prior art) and sample increment count or by other means. The transition from output matrix H3 to H4 occurs when end 10 clears the support at $x_1$=–40 inch. The table in FIG. 4 references the final measurement stage $k_f$. Stage $k_f$ is defined to be the last measurement stage k for which end 10 of board 2 still engages the third support at $X_3$=–24 inch. Stage $k_f$ is determined by testing the position of end 10 relative to $x_3$=–24 inch.

Output matrix H4 is applicable while end 10 is between the supports at $x_1$=–40 inch and $x_2$==–32 inch, thus engaging the supports $x_2, \ldots, x_7$. The components of H4 may be computed similarly to those for H1, H2, and H3 but using the span function $h_4$.

When end 10 clears the support at $x_2$, and while it still engages the supports at $x_3, \ldots, X_7$, output matrix $H_5$ is applicable. $H_5$ is computed similarly to the other output matrices, but using span function $h_5$.

For the preferred embodiment, the development has used p=37 with output matrices having dimensions (1, 37). However, when supports are rigid and alignment is perfect, computations show that the span functions are zero outside the reduced domain between –24 and +24 inch, the condition illustrated by span functions of FIG. 3. Consequently, the size of the problem can be reduced to p=23. The higher number p=37 allows for span functions extending over the domain between –40 and +40 inch and is thus able to deal with span functions for non-rigid and/or misaligned supports. However, there can be speed and noise advantages to reducing the size of the problem if possible to do so.

Relationship Between Local Compliance and State Variables

The first valid compliance measurement $C_m(k)$ is available when k=12, representing the first measurement point for which the first five supports are covered as in FIG. 1. The span function $h_1(x)$, and hence output matrix H(12)=H1, is applicable. Being the initial measurement, $C_m(12)$ is subtracted off all succeeding measurements before invoking the Kalman filter because $C_m(12)$ is the best estimate available of the local compliance mean value. The Kalman filter is derived under the assumption of zero mean random processes. At measurement stage k, the "demeaned" measured compliance value $c_m(k)$ is defined to be $c_m(k)=C_m(k)-C_m(12)$, and it may be put into correspondence with y(k) the output of the dynamic system model previously described. This correspondence is now more completely described.

For the initial measurement stage k=ki=12, the unknown demeaned local compliance c(1)=C(1)–$C_m$(12) at the leading end of the board is identified with $s_8$(12), the 8$^{th}$ component of the state vector. At stage k=13, c(1) is identified with $s_7$(13), the 7th component of the state vector, and so on until at stage k=19, c(1) is identified with $s_1$(19), the first component of the state vector. At stage k=19, the leading end of the board has just passed the last support at $X_7$, and c(1) contributes to no further measurements. The estimated value c*(1) for c(1) is taken as the Kalman estimate $s_1$*(19) of the first of the 37 components of the state vector at stage k=19. The local compliance C*(1) is obtained by adding the estimated mean value $C_m$(12) that had been subtracted earlier. Similarly, at stage 20, C*(2)=$s_1$*(20)+$C_m$(12), and generally at stage k, C*(k–18)=$s_1$*(k)$C_m$(12) until the final measurement stage $k_f$, defined as the last measurement stage k for which trailing end 10 of board 2 still engages the third support at $x_3$. This bookkeeping is listed in the table of FIG. 4.

At stage k=$k_f$, C*($k_f$–18)=$s_1$*($k_f$)+$C_m$(12) following the preceding discussion. However, when k=$k_f$, end 10 of board 2 is ready to clear the support at $X_3$, and no further compliance measurements are available. Remaining local compliance estimates are obtained from their identification with other state vector components estimated at measurement stage $k_f$ as indicated in the table of FIG. 4. Thus, $C^*(k_f-17)=s_2^*(k_f)+C_m(12)$, $C^*(k_r-16)=S_3^*(k_f)+C_m(12)$, and soon until $C^*(k_f+11)=S_{30}^*(k_f)+C_m(12)$, which is the local compliance estimate for the last sampling increment on board 2. Residual error variances for these estimators are available by recognizing that they are the diagonal elements of Kalman filter covariance matrices per the last column of the table in FIG. 4.

The block diagrams of FIGS. 5 through 9 will be helpful in further description and understanding of the state-space representation of the dynamic system model and the correspondence between local compliance, state vector components, and measured compliance.

Dynamic System Model—Output Equation as a Moving Average

Figure 5:
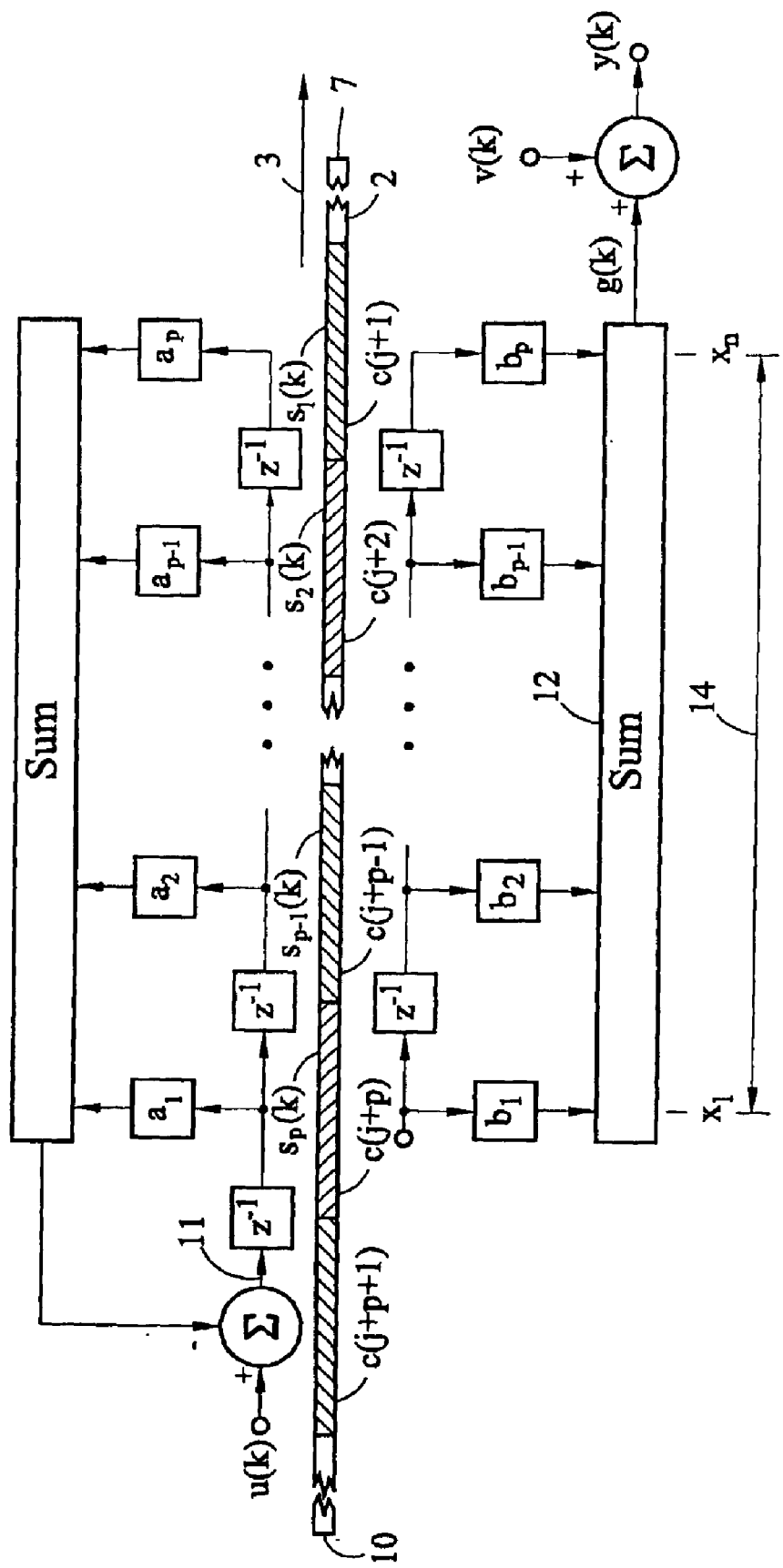
FIG. 5 illustrates a two-part block diagram adjacent a moving beam and is useful in describing the development of the state-space representation of the dynamic system model for compliance measurement.

The block diagram model of FIG. 5 illustrates the system at measurement stage k. Referring to the lower part of FIG. 5, the output y(k), is modeled as a weighted moving average g(k) of the p demeaned local compliance values $c(j+1), \ldots, c(j+p)$ plus measurement noise v(k). For the decimated sampling increment model of the HCLT, the sampling increment is d=2.1866 inch, and p=37. In FIG. 5, board 2 is shown subdivided lengthwise into oppositely hatched elements having length d. These d-inch elements along the board, shown exaggerated in length, are each represented with a single local compliance sample value. In FIG. 5, a contiguous sequence consisting of p of these local values is $c(j+p), \ldots, c(j+1)$, and is shown weighted with coefficients $b_1, \ldots, b_p$, corresponding to a discrete approximation of the bending span weighting applied to that part of beam 2 labeled 14 between the end supports at $x_1$ and $x_n$. For the HCLT, n=7 when all supports are engaged, because the last support is at $x_7$. Assuming operation by an HCLT on wood boards longer than $x_7-X_1=80$ inch, the set of weight coefficients $b_p, \ldots, b_1$ changes and takes on successively the component values from output matrices H1, ..., H5 as a board moves through the machine and engages different subsets of the 7 supports, so that in FIG. 5, n takes on the successive values 5, 6, 7, 6, 5.

Samples of the demeaned local compliance function multiplied by the weight coefficients $b_p, \ldots, b_1$, are summed at 12 to give g(k) and then summed with output noise v(k) to yield y(k), which models at stage k, the demeaned measured compliance $c_m(k)$.

Each block of FIG. 5 labeled $z^{-1}$ represents a delay of one sample increment d=2.1866 inch, which is consistent with board 2 moving in direction 3 by a distance d between samples. As the measurement stage k advances to k+1, the board moves by distance d in direction 3. Each hatched element with its associated compliance value moves to the right by one element length (i.e. the sampling increment d) thereby taking over the position of its predecessor. For example, in FIG. 5, the element labeled c(j+2) moves into position shown for the element labeled c(j+1). At measurement stage k, an equivalence is made between demeaned local compliance c(j+2) and the state variable $s_2(k)$ and between c(j+1) and $s_1(k)$. At the next measurement stage k+1, after the board has moved by one sampling increment d, the equivalence is between c(j+3) and $s_2(k+1)$ and between c(j+2) and $s_1(k+1)$. Thus, $s_1(k+1)=c(j+2)=s_2(k)$, $s_2(k+1)=S_3(k)$ and so on until the last state variable per the state equations specified earlier. The last state variable $s_p(k+1)$, at 11 in FIG. 5, is defined autoregressively in terms of all the state variables at the previous measurement stage and the input u(k). At stage k, the demeaned local compliance c(j+1), as shown in FIG. 5, cannot contribute to any more measurements y(k). After adding back in the mean, the optimal estimate $s_1^*(k)$ of the first state variable $s_1(k)$, through its equivalence with c(j+1), becomes the optimal local compliance estimate for position j+1 along the board. Thus, $C^*(j+1)=C_m(12)+s_1^*(k)$; similarly, $C^*(j+2)=C_m(12)+s_1^*(k+1)$, and so on as described previously. It may be verified for the HCLT of this discussion, that the indices j and k are related by j=k-(p+1)/2=k-19.

Thus, the lower part of the block diagram in FIG. 5 models a demeaned compliance measurement $C_o(k)$ as a weighted moving average of demeaned local compliance values plus measurement noise. The weight coefficients are identified as $b_p, \ldots, b_1$ with subscripts organized in inverse order from the indexing order of the demeaned local compliance values.

While the method as described uses p=37, there are advantages in reducing the size of the problem if leading components of the output matrices, corresponding to coefficients $b_p$, $b_{p-1}$, etc. are zero or nearly zero. This is equivalent to truncating the right part of FIG. 5 and shifting definition of state vector components to the left. In that case, one can extract optimal estimates from earlier stages of the Kalman recursion. If there is little contribution to the output once the leading end of a board passes the fifth support at $x_5$, the optimal estimate can be taken then, rather than waiting until the leading end reaches the last support. This can be tested simply by thresholding the magnitudes of the weighting coefficients $b_p$, $b_{p-1}$ . . . .

Dynamic System Model Local Compliance as Autoregressive Random Process

In the upper part of FIG. 5, each component of the state vector is multiplied by one of the autoregressive coefficients $a_1 \ldots, a_p$, and summed with a minus sign with the input u(k), which is modeled as white noise. The sum at 11 is an autoregressive random process (Papoulis 1991; Hayes 1996). Because demeaned local compliance values are in correspondence with state vector components, demeaned local compliance is modeled as an autoregressive random process.

Combination to Show That Measured Compliance is an ARMA Process

Figure 6:
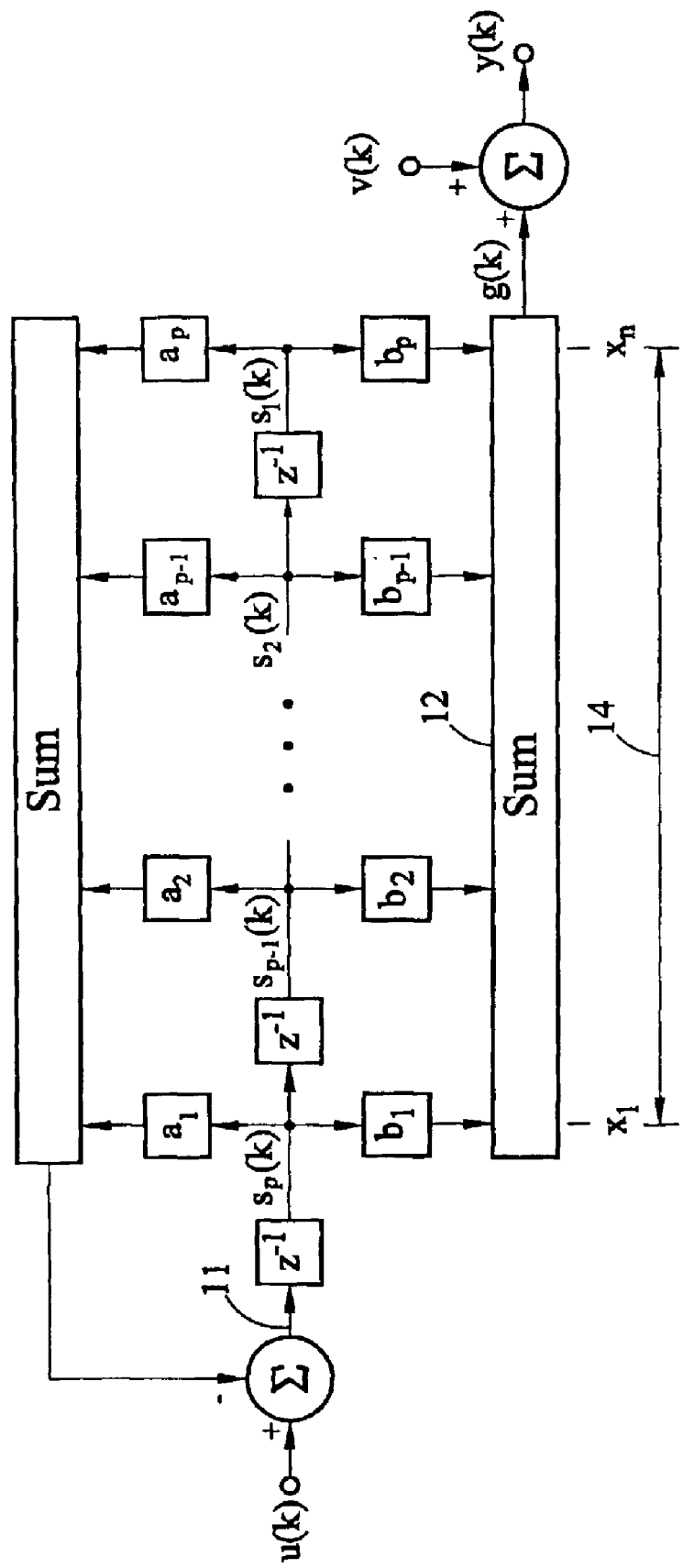
FIG. 6 merges the block diagrams of FIG. 5 into one block diagram showing an autoregressive moving average (ARMA) model for the compliance measurement.

By combining the upper and lower parts of FIG. 5, and eliminating a duplicate set of delay elements, the block diagram of FIG. 6 is obtained. The resulting output g(k) is an autoregressive moving average (ARMA) random process. After adding measurement noise v(k), the result y(k) is representative of HCLT compliance measurements that have had their mean removed. For this model, it is possible to obtain estimates of the autoregressive coefficients $a_1, \ldots, a_p$ from compliance measurements by known methods, reviewed briefly here. The moving average coefficients $b_1, \ldots, b_p$ are determined from analysis of the bending span and computation of span functions and output matrix components as previously described.

Obtaining Autoregressive Coefficients

The autoregressive coefficients may be guessed or evaluated using whatever information is available. However, the following discusses a procedure using measured compliance data. The pulse transfer function (Ogata, 1987) for the system of FIG. 6 relating the z transform $\upsilon(z)$ of the input u to the z transform G(z) of the output g before measurement noise is:

$$\frac{G(z)}{\upsilon(z)} = \frac{b_1 z^{-1} + b_2 z^{-2} + \ldots + b_p z^{-p}}{1 + a_1 z^{-1} + a_2 z^{-1} + \ldots + a_p z^{-p}}$$

The corresponding difference equation is:

$g(k)+a_1 g(k-1)+a_2 g(k-2)+ \ldots +a_p g(k-p)=b_1 u(k-1)+b_2 u(k-2)+ \ldots +b_p u(k-p)$ Following (Papoulis 1991), multiply by g(k−m) and take expected value to obtain: $r_{gg}(m)+a_1 r_{gg}(m-1)+a_2 r_{gg}(m-2)+ \ldots +a_p r_{gg}(m-p) = b_1 r_{ug}(m-1)+b_2 r_{ug}(m-2)+ \ldots +b_p r_{ug}(m-p)$ where $r_{gg}$ is the autocorrelation of g at lag m, and $r_{ug}(m)$ is the cross correlation of u with g at lag m. Because u(k) is white noise, $r_{ug}(m-p)=0$ for m−p>−1. Letting m=p, p+1, ..., p+q−1 gives the q equations:

$$r_{gg}(p)+a_1 r_{gg}(p-1)+a_2 r_{gg}(p-2)+ \ldots +a_p r_{gg}(0)=0$$

$$r_{gg}(p+1)+a_1 r_{gg}(p)+a_2 r_{gg}(p-1)+ \ldots +a_p r_{gg}(1)=0$$

$$r_{gg}(p+2)+a_1 r_{gg}(p+1)+a_2 r_{gg}(p)+ \ldots +a_p r_{gg}(2)=0$$

$$r_{gg}(p+q-1)+a_1 r_{gg}(p+q-2)+a_2 r_{gg}(p+q-3)+ \ldots a_p r_{gg}(q-1)=0$$

From FIG. 6:

$$y(k)=g(k)+v(k)$$

Because v is a white noise process and statistically independent of g, multiplication by y(k−m) and taking expected value, E[ ], gives:

$$E[y(k)y(k-m)] = E[g(k)g(k-m)] + E[v(k)v(k-m)]$$

$$r_{yy}(m) = r_{gg}(m) + r_{vv}(m)$$

$$= \begin{cases} r_{gg}(0) + r_{vv}(0) = r_{gg}(0) + \operatorname{var}(v), & m=0 \\ r_{gg}(m), & m \neq 0 \end{cases}$$

Consequently, the equations involving autocorrelations of g can be replaced with autocorrelations of y, which can be estimated from measured compliance data. The autocorrelation component $r_{gg}(0)=r_{yy}(0)-\operatorname{var}(v)$ requires an estimate of measurement noise variance var(v). Because g is a moving average, $r_{gg}$ cannot change rapidly with argument, hence $r_{gg}(0)$ may be approximated with $r_{gg}(1)$, and:

$$\operatorname{var}(v)=r_{yy}(0)-r_{gg}(0) \approx r_{yy}(0)-r_{gg}(1)=r_{yy}(0)-r_{yy}(1)$$

This approximation of the output noise variance can be used elsewhere in the procedure, but it may be avoided for the present purpose by increasing the argument of every term in the equations by one. Equivalently, one can drop the first equation and add another at the end, giving:

$$r_{yy}(p+1)+a_1 r_{yy}(p)+a_2 r_{yy}(p-1)+ \ldots +a_p r_{yy}(1)=0$$

$$r_{yy}(p+2)+a_1 r_{yy}(p+1)+a_2 r_{yy}(p)+ \ldots +a_p r_{yy}(2)=0$$

$$r_{yy}(p+3)+a_1 r_{yy}(p+2)+a_2 r_{yy}(p+1)+ \ldots +a_p r_{yy}(3)=0$$

$$\vdots$$

$$r_{yy}(p+q)+a_1 r_{yy}(p+q-1)+a_2 r_{yy}(p+q-2)+ \ldots +a_p r_{yy}(q)=0$$

In matrix form:

$$\begin{bmatrix} r_{yy}(p) & r_{yy}(p-1) & r_{yy}(p-2) & \ldots & r_{yy}(1) \\ r_{yy}(p+1) & r_{yy}(p) & r_{yy}(p-1) & \ldots & r_{yy}(2) \\ r_{yy}(p+2) & r_{yy}(p+1) & r_{yy}(p) & \ldots & r_{yy}(3) \\ \vdots & \vdots & \vdots & \ddots & \vdots \\ r_{yy}(p+q-1) & r_{yy}(p+q-2) & r_{yy}(p+q-3) & \ldots & r_{yy}(q) \end{bmatrix} \begin{bmatrix} a_1 \\ a_2 \\ a_3 \\ \vdots \\ a_p \end{bmatrix} =$$

$$- \begin{bmatrix} r_{yy}(p+1) \\ r_{yy}(p+2) \\ r_{yy}(p+3) \\ \vdots \\ r_{yy}(p+q) \end{bmatrix}$$

In shorthand $$Ra=b$$

where the obvious definitions of the (q,p)-dimensional matrix R, the (p,1)-dimensional vectors and the (q,1)-dimensional vector b are made. The number of equations q may be more than, equal to, or less than the number p of autoregressive coefficients.

In matrix R and in vector b the autocorrelation function ry for arguments 1, ... p+q may be estimated from compliance measurements $C_m(k)$. There are numerous references discussing autocorrelation estimation methods, one of them being (Oppenheim and Schaefer 1989). An important detail for accurate estimation of autocorrelation is to first subtract the data mean from the data. Obtaining autocorrelation estimates from "demeaned" data is equivalent to obtaining autocovariance estimates. In one software package MATLAB available from the MathWorks in Natick Mass., the "detrend" command can remove slope, as well as mean, from the data. For purposes of obtaining autoregressive coefficients, the recommendation of this specification is to remove both mean and slope. Data with mean and slope removed are "detrended".

Obtaining autocorrelation from measured compliance values and then the autoregressive coefficients are intended to be preliminary steps. These steps may be performed using data gathered over a period of time from a prescribed common population. For example, the data could be HCLT compliance measurements of wood boards coming from a particular species mix or from trees grown in a particular locale. The following set of steps can be used to estimate autocorrelation values from compliance measurements of wood boards:

Measure compliance $C_m(k)$ for all possible arguments k on a board 2, that is, for all possible measurement points (k−½)d inch from the leading end 7 of a board (see FIG. 1). For this board, obtain and define the detrended data as $c_{md}(k)$. If, as is likely for presently operating HCLT's, the calibration is not correct for all five bending span configurations, an additional restriction should be imposed. Only data from measurement points between 40.4521 inch, that is, 18.5 sample increments, from either end of the board should be used. This restricts the output matrix to be $H_3$, and only the calibration factor $K_3$ is applicable.

For lag m=0 and greater, form all possible products $\xi(m)=c_{md}(k) \, c_{md}(k-m)$ of the detrended data for all values of k and k−m for which measured compliance is available on the board.

Repeat the previous steps for each of the boards from the common population that will contribute to the result.

Average all available products ξ(m) at each lag argument m to obtain estimates of the autocorrelation as:

$$r_{yy}(m) = \frac{\sum_{i=1}^{N(m)} \xi(m)}{N(m)},$$

where N(m) is the total number of products ξ(m) available at lag m.

The number N(m) available for large lag m will be smaller than for small lags. Consequently, the quality of autocorrelation estimation at the larger lags is reduced. If as above, the output matrix is restricted to H3, then to obtain data for lag p+q, the board must be 2p+q sample increments long to get just one lag p+q sample product datum per board. For example, if q=p, the board length must be 3p sample increments or 242.7126 inch for just one product datum per board. Alternatives are to ensure that calibration is correct for each of the five bending span configurations (not part of present HCLT calibration procedure) and use data closer to the board ends, use a reduced number q of equations, or test longer boards. Hence:

To obtain best results, compliance measurements $C_m(k)$ should be taken for the longest representative boards available. Some curve fitting to smooth the ry function may be desirable.

The variance of measurement noise may be approximated as $\text{var}(v) = r_{yy}(0) - r_{yy}(1)$.

Solving the Equations: Ra=b

The equations Ra=b with (q,p)-dimensional matrix R may have a unique solution for the autoregressive coefficients a, no solution, or many solutions. Instead of solving directly, this equation is first premultiplied by RT, the transpose of R, to obtain the "normal equations":

$$R^T R a = R^T b$$

The normal equations always have a solution, but there may be many solutions, depending on the rank r of R. It may be shown (Rao 1965) that any solution of the normal equations is a least squares solution of Ra=b. That is, $(Ra-b)^T(Ra-b)$ is minimized, regardless of the relative sizes of dimensions q and p, regardless of whether or not an exact solution to Ra=b exists, and regardless of whether or not R has full rank. From use of a generalized inverse (Rao 1965), singular value decomposition (Strang and Borre 1997), and Lagrange multipliers, the particular least squares solution given by:

$$a = V_r \Sigma_r^{-1} U_r^T b$$

can be shown to have the smallest norm $(a^T a)^{1/2}$ of any of the least squares solutions. In this result, r is the rank of R, and the matrices $V_r$, $U_r$, and $\Sigma_r$ are obtained from just the strictly positive eigenvalues and corresponding eigenvectors of $R^T R$ according to:

$$R^T R v_i = \lambda_i v_i, \quad \lambda_1 \geq \ldots \geq \lambda_r \geq \lambda_{r+1} = \ldots = \lambda_p = 0$$

$$V_r = [v_1 \ldots v_r], \quad v_i^T v_j = \begin{cases} 0, & i \neq j \\ 1, & i = j \end{cases}$$

$$U_r = [\mu_1 \ldots \mu_r], \quad \mu_i = \frac{R v_i}{\sqrt{\lambda_i}}, \quad i = 1, \ldots, r$$

$$\Sigma_r = \begin{bmatrix} \sqrt{\lambda_1} & 0 & \ldots & 0 \\ 0 & \sqrt{\lambda_2} & \ddots & \vdots \\ \vdots & \ddots & \ddots & 0 \\ 0 & \ldots & 0 & \sqrt{\lambda_r} \end{bmatrix}$$

The eigenvalues are real and non-negative because $R^T R$ is symmetric. The number r of nonzero eigenvalues is equal to the rank of R. If an eigenvalue is very close to zero when compared to the other nonzero eigenvalues, then usually it should be assumed zero, and the rank r adjusted accordingly. The (p,r)-dimensional matrix V, and (q,r)-dimensional matrix $U_r$ are each defined as r columns of eigenvectors corresponding to the r positive eigenvalues, the eigenvalues being common to both $R^T R$ and $RR^T$. The vectors $v_i$ are orthonormal eigenvectors of $R^T R$. It follows that the vectors $\mu_i$ are orthonormal eigenvectors of $RR^T$.

Thus, the coefficients $a_1, \ldots, a_p$ for the autoregressive part of the block diagram in FIG. 6 and for the state matrix defining the dynamic system may be obtained as part of the a priori information for the population of wood boards being considered. While the above gives the minimum norm solution for the autoregressive coefficients, other least squares solutions may exist and can be used. For example, a solution having the least number of nonzero coefficients can be sought.

In practice, a reduced set of autoregressive coefficients may be obtained and used. For example, the block diagram of FIG. 7 retains only $a_1$. In that case the state matrix for the model is:

$$\phi = \begin{bmatrix} 0 & 1 & 0 & \ldots & 0 \\ 0 & 0 & 1 & \ddots & \vdots \\ \vdots & \vdots & \ddots & \ddots & 0 \\ 0 & 0 & \ldots & 0 & 1 \\ 0 & 0 & \ldots & 0 & -a_1 \end{bmatrix}$$

By the steps presented, the coefficients of an ARMA model for measured compliance are obtained. The autoregressive coefficients may be guessed, using available information, or they may be obtained from other preliminary efforts as described. The moving average coefficients are obtained from span functions by analysis of the bending spans involved. The model can be presented in the form of a difference equation, a block diagram such as in FIG. 6 or FIG. 7, or as a state-space representation of a dynamic system.

Figure 7:
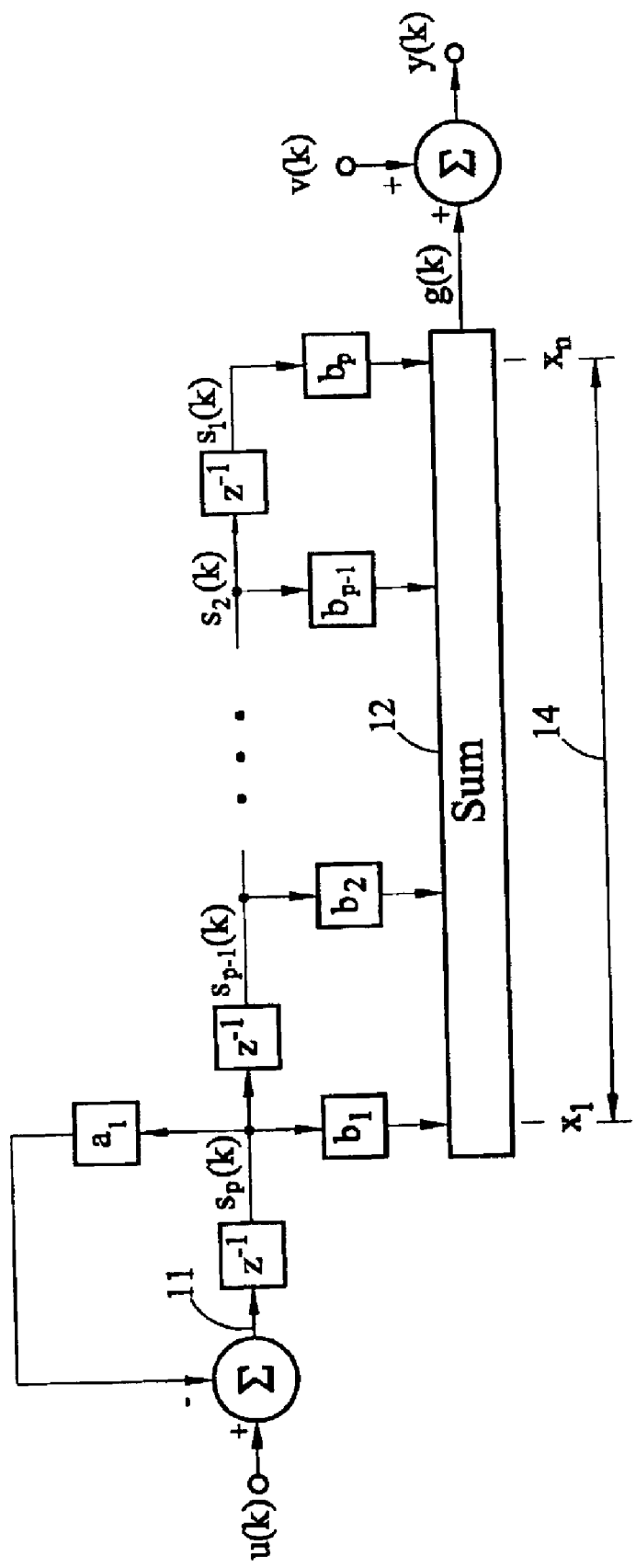
FIG. 7 is a reduced ARMA model with only one autoregressive coefficient.

The models of FIG. 5 and then of FIGS. 6 and 7 have been developed with output y(k) having zero mean so that the zero mean assumption for input to the Kalman filter is satisfied. The demeaned values c(j) of local compliance have been defined and put into correspondence with state variables of the model. In the model, the local compliance values c(j) and the output y(k) have zero mean. This is not consistent with actual beam local compliance values, and certainly not for wood boards. However, it is an assumption required in the derivation of the Kalman filter. To use the Kalman filter for optimal estimation, the measured compliance values are demeaned and the model showing local compliance function as an autoregressive process assumes zero mean. Because the output noise is assumed to be additive and zero mean, the output y(k) of the model also has zero mean. Thus, the output of the model has been placed into correspondence with the demeaned compliance data. The Kalman filter, discussed next, operates with a state-space representation of the dynamic system model to obtain estimates of the demeaned local compliance values making use of their correspondence with state variables of the model.

Overview of the Kalman Filter

The Kalman filter output, at any measurement stage, is the optimal estimate of the state vector in a dynamic system model. In his 1960 paper, Kalman discusses the sense in which the estimate is optimal. The Kalman filter estimator is the minimum variance unbiased linear estimator given the data. The variance of the residual error for every component of the state vector is minimized.

The demeaned local compliance estimates are identified with components of the state vector for the defined dynamic system. When the last measurement is obtained that has in it a contribution from a local compliance, an estimate of that compliance is taken as the Kalman estimate for its associated state vector component.

Kalman Filter Initialization

To apply the Kalman filter, some a priori information in addition to the model coefficients in the state matrix and the output matrix must be provided. Accuracy of the results will depend on accuracy of the a priori information. Variances var(u) and var(v) for the input and measurement white noise random processes, u(k) and v(k) must be specified along with the initial covariance P*(i) of the state vector residual error. The preferred embodiment description will proceed with the simplified model illustrated by the block diagram of FIG. 7. The autoregressive coefficient $a_1$ is required. With this model, $-a_1 = \rho$ is the correlation coefficient between local compliance values for adjacent sample increments along wood boards. The variance var(u) of the input and the correlation $\rho$ represent information about the statistics of lumber properties. From compliance measurements, $\rho$ and var(v) may be obtained by the steps discussed earlier. While not necessary, both u(k) and v(k) are assumed in the preferred embodiment to be stationary random processes, so that their variances do not vary with k. The Kalman filter will accommodate nonstationary u(k), V(k), state matrix $\phi(k)$, and output matrix H(k) so that the method allows them to be functions of k. If it is known that these quantities vary with time, then that information can be included easily in the model. In the preferred embodiment, H(k) is taken as nonstationary because it is known that the span function and hence output matrix changes as different bending spans are encountered.

An initial estimate of mean compliance value must be available to get the Kalman process started. This is subtracted from each measured compliance datum as it arrives, making the measured compliance data zero mean, one of the assumptions in the derivation of the Kalman filter. At the end of the estimation process, the subtracted value is added back in to get the result. The initial measured compliance value is used as the mean. Early experiments estimated mean value from known information of the board population, but it was discovered that the first compliance measurement for a board gave better results. Further, it is reasonable that the first measured value would be the best estimate of mean for an individual board. Consequently, the first measured compliance value $C_m$ for each wood board is treated as the mean, and subtracted from each subsequent compliance measurement for the board to obtain the demeaned data sequence for entry to the Kalman filter.

Thus, the demeaned measurement data sequence $c_m(k)$ is modeled by y(k), the output of the model in FIG. 7.

$$y(k) = c_m(k) = C_m(k) - C_m(12)$$

where $C_m(k)$ is the measured compliance sequence, and k=12 is identified as the first measurement stage k for which a measurement is available using an HCLT. After obtaining the Kalman estimates, the first measured value $C_m(12)$ is added to obtain estimated local compliance.

More generally than in FIG. 7, the ARMA model of FIG. 6 with a more complete set of autoregressive coefficients could be used. The difference insofar as the Kalman filter is concerned is in the state matrix $\phi$ where the last row entries would consist of the coefficients $[-a_p, \ldots, -a_1]$ instead of $[0, \ldots, 0, -a_1]$ as used with the Model of FIG. 7. The autoregressive coefficients can be obtained from data as previously described.

The optimal estimator for the state vector at stage k is denoted s*(k). Initially this is taken as the mean value of the state vector at stage k=ki=12, which is the zero vector. That is s*(12) 0.

The covariance matrix Q(k) for the dynamic system input vector U(k) is $$Q(k) = E[U(k)U^T(k)] = \begin{bmatrix} 0 & 0 & \ldots & 0 & 0 \\ 0 & 0 & \ldots & 0 & 0 \\ \vdots & \vdots & \ddots & \vdots & \vdots \\ 0 & 0 & \ldots & 0 & 0 \\ 0 & 0 & \ldots & 0 & \text{var}(u(k)) \end{bmatrix}$$

The only nonzero entry of this (p,p)dimensional matrix is the last diagonal element which contains the variance var(u(k)) of the input random process u(k).

The initial optimal estimate of the state vector is s*=0, hence the initial covariance matrix P*(ki) of the state vector residual error s(ki)-s*(ki)=s(ki) is:

$$P^*(ki) = E[s(ki)s^T(ki)]$$
$$= E[(\phi s(ki-1) + U(ki-1))(s^T(ki-1)\phi^T + U^T(ki-1))]$$
$$= \phi E[s(ki-1)s^T(ki-1)]\phi^T + E[U(ki-1)U^T(ki-1)]$$
$$= \phi P^*(ki-1)\phi^T + Q(ki-1)$$

where for the HCLT with sample increment d=2.1866 inch, ki=12. The cross terms between s(ki-1) and U(ki-1) in the above are zero because u(k) is a white noise process and hence uncorrelated with s(k) which has embedded in it only inputs u(k-1) and earlier. With stationary processes and no prior information before measurement stage ki, there is no reason to suggest initially that optimal estimation of state vector s* should be different from zero. The above computation assumes mean zero at both stages ki and ki-1. There is no reason to suggest that P* is different at stage ki than at stage ki-1, and thus:

$$P^* = \phi P^* \phi^T + Q$$

This equation has been called a discrete Lyapunov equation (Kailath 2000). Here, the definitions of $\phi$, Q, and the initial matrix P* are referred to as "consistent" if they satisfy the discrete Lyapunov equation. It is easily verified that P* is consistent if it is given by:

$$P^* = \sigma^2 T$$

where the (p,p)-dimensional Toeplitz matrix T and the common variance $\sigma^2$ for the state vector components are defined as:

$$T = \begin{bmatrix} 1 & \rho & \rho^2 & \cdots & \rho^{p-1} \\ \rho & 1 & \rho & \cdots & \vdots \\ \rho^2 & \rho & 1 & \ddots & \vdots \\ \vdots & \vdots & \ddots & \ddots & \rho \\ \rho^{p-1} & \cdots & \cdots & \rho & 1 \end{bmatrix}, \quad \sigma^2 = \frac{1}{1-\rho^2} \text{var}(u)$$

This choice of P* is a consistent choice of initial covariance matrix for the state vector s. From a priori considerations, e.g. known variability of lumber compliance giving $\sigma^2$, and preliminary determination of $\rho$ from prior measurements, these relationships can be used to specify $\text{var}(u)=\sigma^2(1-p^2)$ and hence Q. The measurement noise variance $\text{var}(v)$ is known from observations or from $\text{var}(v)=r_{yy}(0)-r_{yy}(1)$.

The Kalman Filter Recursion

The Kalman filter is recursive and for the HCLT has the steps:

1. Initialize:
   Set k=ki=12;p=37.
   Define initial state estimate as the zero vector, s*(k)=0
   Set initial covariance matrix P*(k), e.g. according to:

$$P^*(k) = \sigma^2 T = \frac{\text{var}(u)}{1-\rho^2} T$$

Identify H(k)=H1, and compute the initial Kalman gain K(k):

$$K(k)=P^*(k)[H^T(k)H^T(k)P^*(k)H^T(k)+\text{var}(v)]^{-1}$$

Compute the matrix factor F(k):

$$F(k)=I_p-K(k)H(k)$$

where $I_p$ is a p-dimensional identity matrix.

2. Set k=k+1, and perform Kalman iteration:
   a Compute covariance matrix P*(k) at measurement stage k:

$$P^*(k)=\phi F(k-1)P^*(k-1)\phi^T+Q$$

Compute Kalman gain K(k) at stage k, using current P*(k) and H(k):

$$K(k)=P^*(k)H^T(k)[H(k)P^*(k)H^T(k)+\text{var}(v)]^{-1}$$

Compute matrix factor F(k) at stage k:

$$F(k)=I_p-K(k)H(k)$$

Compute optimal state vector estimate s*(k) at stage k:

$$s^*(k)=F(k)\phi s^*(k-1)+K(k)y(k)$$

where $y(k)=c_m(k)=c_m(k)-C_m(12)$.

Compute covariance matrix P(k) at stage k for the optimal estimator:

$$P(k)=F(k)P^*(k)$$

3. If k<$k_f$, go to Step 2, and repeat.

Notes:

i.) There is a subtle distinction between the covariance P*(k), which is used in the above recursion procedure, and P(k). P(k) is the covariance of the residual error between the state vector s(k) and the optimal estimator s*(k) for it at the $k^{th}$ stage. The optimal estimator uses all the data up through the measurement y(k). The notation s*(k|k) would be more consistent with Kalman's paper, (Kalman 1960). P*(k) is the covariance of the residual error between the state vector s(k) and another optimal estimator s*(k|k-1) for it at the $k^{th}$ stage, but this second estimator uses measurements only up through y(k-1) and does not include y(k). The estimate is predicted by the dynamic system but not corrected by information in the measurement y(k). Details are explained more fully elsewhere (Bechtel 2001). In the steps of the above recursion, s*(k) refers to s*(k|k) and therefore uses the measurement y(k). P*(k) is used in the recursion. P(k) is computed to obtain the residual error variance of the estimators used for beam compliances.

ii.) For the HCLT preferred embodiment with sampling increment d=2.1866 inch, the first measurement is taken when k=12. The output matrix (row vector) H(k) is indexed by k. For k=12 to 15, H(k)=H1; for k=16 to 18, H(k)=H2; for k=19 to $k_f$-7, H(k)=H3; for k=$k_f$-6 to $k_f$-4, H(k)=H4; and for k=$k_f$-3 to $k_f$, H(k)=H5. These details are in the table of FIG. 4.

iii.) For the HCLT preferred embodiment, the local compliance estimates and their residual error variances are obtained from the Kalman recursion according to the table in FIG. 4.

iv.) FIG. 4 shows the local compliance estimates with the first compliance measurement $C_m$ (12) added back in as explained above. If the local E (or I or EI depending on definition of C) is desired, the reciprocal is taken. For example $E^*(j) \cong 1/C^*(j)$ and coefficient of variation $COV_E(j) \cong COV_C(j)$ or using the next better approximations: $E^*(j) \cong (1+COV_C^2(j))(C^*(j))$ and $COV_E(j) \cong COV_C(j)/(1+COV_C^2(j))$.

v.) Estimates including error variance are available from the leading end of the beam while the beam is being processed. It is not necessary to wait until the entire measurement sequence from the beam is obtained to output results from the leading end. In the table of FIG. 4 for the HCLT, the estimate for C(j) is available at stage k=j+18, or sooner near the trailing end of the beam. A small additional delay is caused by the data preprocessing, which decimates the data at 0.54664 inch sampling increments. The variance of each of the compliance estimates is obtained from diagonal values of the covariance matrices P(k). For those compliance estimates identified as first components of optimal state vector estimates, the leading diagonal element of P(k) is the error variance. For each compliance estimate identified as a component of an optimal state vector estimate other than the first, then the component index determines the position on the diagonal of P(k) where the variance is found. The last column of the table in FIG. 4 contains this detail.

vi.) The data are used to improve estimation of the state vector. They are not used to update the Kalman gain K(k), matrix factor F(k), or covariance matrix P*(k). While it is not necessary to do so, the computations involved for these matrices may be performed ahead of time and the results for each measurement stage k stored. The computer code is not required to perform these operations as part of the data processing for each board tested. This is particularly useful if the input and measurement noise processes are stationary. However, in the HCLT the output matrix changes with k and hence is not stationary. The length of a board affects the number of measurement stages k for which output matrix H3 is applicable, and hence the number of iterations involving H3.

If the matrices K(k), F(k) and P*(k) converge quickly to steady values during the interval for which H3 is active, then efficient code with minimal storage requirements can be written by assigning the same K, F, and P* matrices for all k greater than some threshold so long as H3 is active. In that case, there will be only one matrix sequence and hence reduced storage requirement for K, F, and P* when, following H3, the output matrices H4 and H5 are active.

Figure 12:
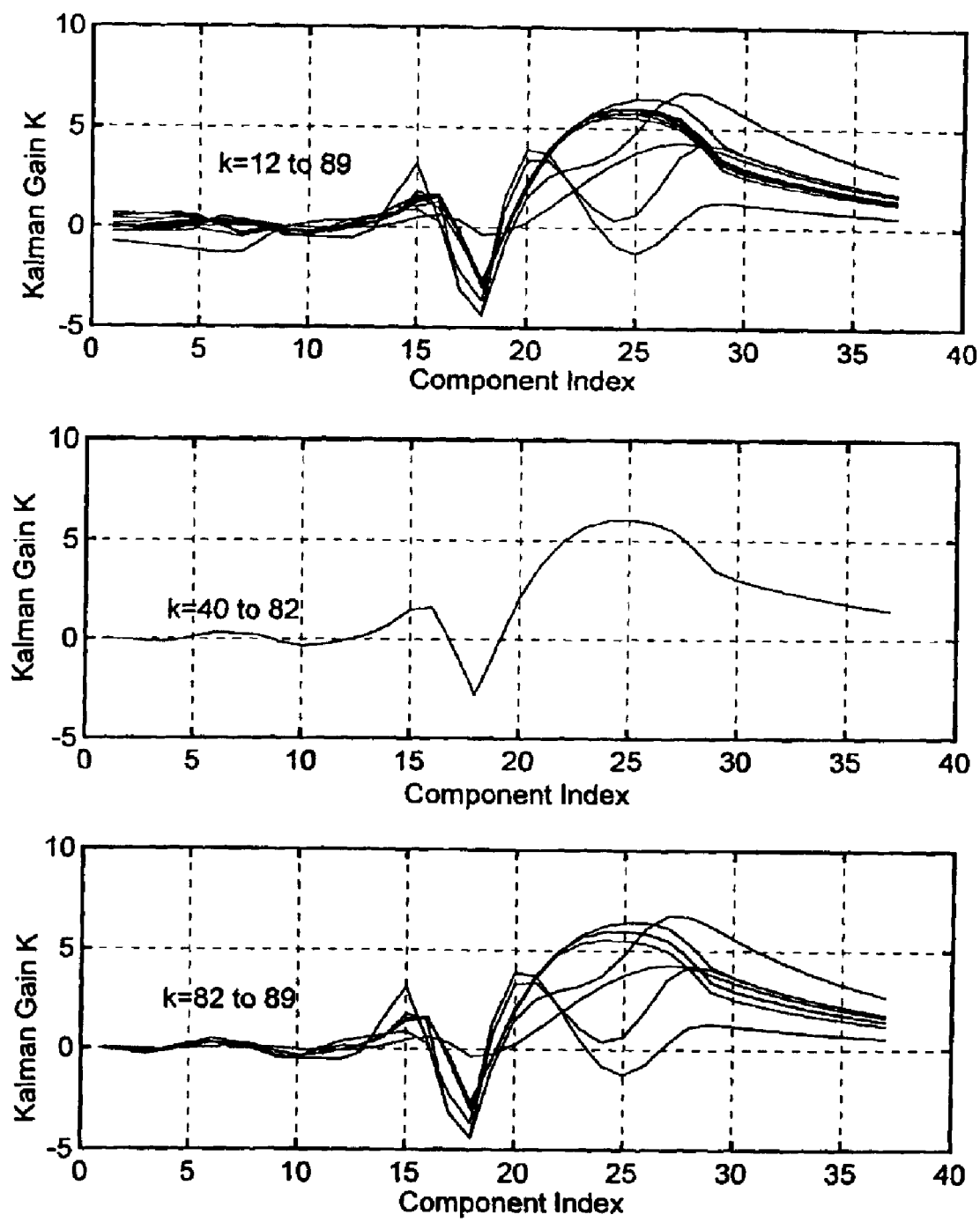
FIG. 12 illustrates the convergence properties of the Kalman gain vector during processing of a beam.

For example, in the experiments to be described, where simulated boards were 100 sample increments, i.e. 218.66 inch, long, the upper part of FIG. 12 illustrates the entire family of Kalman gain vectors for measurement stages k=12 to 89. Each curve in this family represents the components of one Kalman gain vector K(k) for a particular measurement stage k, each vector K(k) being p=37 components long. The center part of FIG. 12, represents the family of Kalman gain vectors for measurement stages 40 to 82. Output matrix remains H3 for k=19 through k=82. Clearly, the Kalman gain vector has settled substantially to a fixed vector by measurement stage k=40 and remains there through k=82. After k=82, the output matrix becomes H4 and then H5. The lower part of FIG. 12 shows the family of Kalman gain vectors K for k=82 to 89, 82 being included to show how it fits with the others. The stationarity and convergence of K is lost after k=82. Nevertheless, the sequence of values for each of the eight stages in the sequence from k=82 to k=89 may be stored ahead of time and used when required. These same values are applicable for the last eight steps of any board in a common population having length more than about 40 sample increments long.

Starting Values Used with Experiments

The values, var(u), var(v) and p must be selected before beginning. Results of the Kalman filter operation are optimal, but they are optimal within the assumptions used. Parameter estimates as close to the truth as possible should be used and modified if better information becomes available. Procedures for obtaining these values from measurements have been described. Other means as now described were used to select values for experiments reported here.

First, consider the value for the variance var(v) of measurement noise. In the case of lumber passing through the HCLT, history of this type of machine measurement is used to state that the standard deviation of the measurement noise is on the order of 0.7 percent of the measurement. For the compliance units used, which are reciprocals of E, 0.7 percent of the measurement is on the order of 0.0035 $(10^6$ psi$)_{-1}$. This assumes compliance is defined by 1/E rather than 1/(E1). The variability is reduced further because adjacent samples of more densely sampled data are filtered during decimation to obtain samples at the 2.1866 inch sample spacing. A reasonable value for measurement noise variance is:

$$var(v) = 0.00001 \ (10^6 \ \text{psi})_{-2}$$

The earlier discussion involving estimation of autoregressive coefficients describes another approach for estimating var(v).

The literature shows that the coefficient of variation (COV) of MOE, and thus similarly for compliance, is in the approximate range of 0.3 to 0.4 for beams that are wood boards. If it is 0.4, and if average compliance is about 0.5 $(10^6 \ \text{psi})^{-1}$, then the standard deviation is about 0.2 $(10^6 \ \text{psi})^{-1}$ and the variance 0.04 $(10^6 \ \text{psi})^{-2}$. Thus, a reasonable a priori number for the variance of local compliance is:

$$\sigma^2 = 0.04 (10^6 \ \text{psi})^{-2}$$

A consistent choice for var(u) is:

$$var(u) = \sigma^2(1-\rho^2)$$
$$= 0.04(1-\rho^2)(10^6 \ \text{psi})^{-2}$$

From this, a specification of the correlation coefficient σ will define input noise variance var(u).

The correlation coefficient, giving the correlation between compliance values from adjacent sample increments is not known, although steps for computing it from measured compliance data have been presented in this specification. There is a body of literature addressing the experimental correlation and models of correlation in lumber for flatwise bending E at different sample increments. These increments have generally been multiples of 24 or 30 inch (Kline et al. 1986, Richburg and Bender 1992, Taylor and Bender 1989 and 1991, Hernandez et al. 1992, Taylor et al. 1992). While extrapolating these longer lag correlation results for E to the present short lag of 2.1866 inch and using the result for compliance causes a bit of unease, such an extrapolation provides a starting point.

The correlation has been reported variously, but is in the neighborhood of 0.93 for a 24-inch lag. A lag of 24 inch for the referenced work corresponds to a lag multiple of 24/2.1866 for the 2.1866 inch sample spacing used here for the HCLT. An extrapolated result for the correlation coefficient with lag of 2.1866 inch is:

$$\rho = 0.93^{2.1866/24}$$
$$= 0.993$$

It is suspected that local wood board properties will alter the correlation statistics when lag distances get small enough to be on the order of knot size as they are in this case. Consequently, the actual correlation is likely much less than 0.993. The experiments tried a number of different correlation values, but if p=0.97 is used, var(u) may be specified as:

$$\sigma = 0.97 \Rightarrow var(u) = 0.04 \ (1-0.97^2) = 0.002364(10^6 \ \text{psi})^{-2}$$

As compliance measurement data are obtained, information about the correlation coefficient σ may be improved by the computational process identified.

Additional Flexibility in the Model for Local Compliance

The models suggested in FIGS. 6 and 7 allow great flexibility in modeling local compliance as an autoregressive random process. The autoregressive coefficients as in the figures can be computed from the data by the methods identified in this specification and modified as additional data are obtained.

Figure 8:
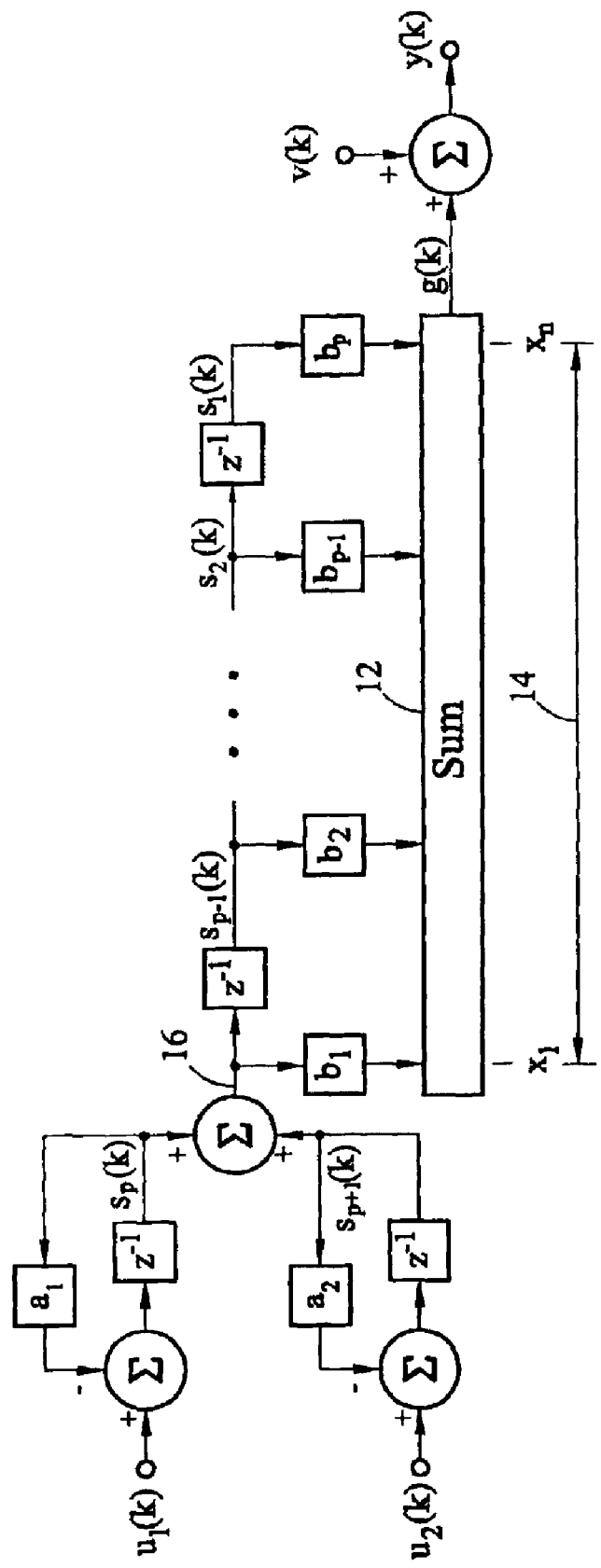
FIG. 8 is an ARMA model with two input branches, statistically independent input noise processes and two autoregressive coefficients, one for each input branch.

The model can be allowed additional flexibility by the arrangement of the block diagram in FIG. 8 which illustrates two statistically independent random noise input processes $u_1(k)$ and $u_2(k)$ that may be used with two autoregressive coefficients $a$, and $a_2$. The last two state variables in a (p+1,1) dimensional state vector combine to form a local compliance value at 16, which is passed along as before via the state matrix to the other state variables. One of the moving average coefficients $b_1$, i.e. output matrix weights, appears twice. In this case, a (p+1,p+1)-dimensional state matrix, (p+1,1) dimensional input vector, (p+1,p+1)-dimensional covariance matrix for the input vector, (1,p+1) dimensional output matrix, and (p+1,1)-dimensional state vector are defined by:

$$\phi = \begin{bmatrix} 0 & 1 & 0 & \cdots & 0 & 0 \\ 0 & 0 & 1 & \ddots & \vdots & \vdots \\ \vdots & \vdots & \ddots & \ddots & 0 & 0 \\ 0 & 0 & \cdots & 0 & 1 & 1 \\ 0 & 0 & \cdots & 0 & -a_1 & 0 \\ 0 & 0 & \cdots & 0 & 0 & -a_2 \end{bmatrix}, \quad U(k) = \begin{bmatrix} 0 \\ \vdots \\ 0 \\ u_1(k) \\ u_2(k) \end{bmatrix},$$

$$Q = \begin{bmatrix} 0 & \cdots & 0 & 0 & 0 \\ \vdots & \ddots & \vdots & \vdots & \vdots \\ 0 & \cdots & 0 & 0 & 0 \\ 0 & \cdots & 0 & \text{var}(u_1) & 0 \\ 0 & \cdots & 0 & 0 & \text{var}(u_2) \end{bmatrix}$$

$$H(k) = [b_p \ \ldots \ b_2 \ b_1 \ b_1],$$

$$s(k) = [s_1(k) \ldots s_p(k) \ s_{p+1}(k)]^T$$

The sum of the $b_j$ coefficients is one, but the coefficient $b_1$ is included only once in this sum. Variances $\text{var}(u_1)$ and $\text{var}(u_2)$ are the variances of the two input noise processes. Define:

$$\rho_1 = -a_1 \quad \sigma_1^2 = \frac{\text{var}(u_1)}{1 - \rho_1^2} = \alpha^2 \sigma^2$$

$$\rho_2 = -a_2 \quad \sigma_2^2 = \frac{\text{var}(u_2)}{1 - \rho_2^2} = (1 - \alpha^2)\sigma^2$$

where $0 \leq \alpha^2 \leq 1$. The parameter $\alpha^2$ apportions the observed variance $\sigma^2$ of local compliance to the two statistically independent input branches of FIG. 8. A consistent initial covariance matrix for the state vector residual error is:

$$P^* = \sigma_1^2 V_1 + \sigma_2^2 V_2$$

The matrices $V_1$ and $V_2$ are given by:

$$V_1 = \begin{bmatrix} 1 & \rho_1 & \rho_1^2 & \cdots & \rho_1^{p-2} & \rho_1^{p-1} & 0 \\ \rho_1 & 1 & \rho_1 & \cdots & \rho_1^{p-3} & \rho_1^{p-2} & 0 \\ \rho_1^2 & \rho_1 & 1 & \ddots & \vdots & \rho_1^{p-3} & 0 \\ \vdots & \vdots & \ddots & \ddots & \ddots & \vdots & \vdots \\ \rho_1^{p-2} & \rho_1^{p-3} & \cdots & \ddots & 1 & \rho_1 & 0 \\ \rho_1^{p-1} & \rho_1^{p-2} & \rho_1^{p-3} & \cdots & \rho_1 & 1 & 0 \\ 0 & 0 & 0 & \cdots & 0 & 0 & 0 \end{bmatrix},$$

$$V_2 = \begin{bmatrix} 1 & \rho_2 & \rho_2^2 & \cdots & \rho_2^{p-2} & 0 & \rho_2^{p-1} \\ \rho_2 & 1 & \rho_2 & \cdots & \rho_2^{p-3} & 0 & \rho_2^{p-2} \\ \rho_2^2 & \rho_2 & 1 & \ddots & \vdots & 0 & \rho_2^{p-3} \\ \vdots & \vdots & \ddots & \ddots & \ddots & \rho_2 & \vdots & \vdots \\ \rho_2^{p-2} & \rho_2^{p-3} & \cdots & \rho_2 & 1 & 0 & \rho_2 \\ 0 & 0 & 0 & \cdots & 0 & 0 & 0 \\ \rho_2^{p-1} & \rho_2^{p-2} & \rho_2^{p-3} & \cdots & \rho_2 & 0 & 1 \end{bmatrix}$$

It may be verified with some arithmetic that the discrete Lyapunov equation is satisfied by $P^*$. As previously, the initial measurement stage for the HCLT when the sample increment is 2.1866 inch is taken as k=12.

The two input ARMA model of FIG. 8 is somewhat similar to the one input ARMA model of is FIG. 6 if all autoregressive coefficients except $a_1$ and $a_2$ are set to zero. Two non-oscillatory decay rates for local compliance correlation of modeled beams may be set with either model. However, the model of FIG. 8 is preferred to control how much of each decay rate is present. This can be useful, for example in wood boards, where a knot component of local compliance may have autocorrelation that reduces rapidly with distance (rapid decay), versus a clear-wood component having autocorrelation that reduces more slowly (slow decay). Rapid decay is obtained by setting coefficient $\rho_1$ small, and slow decay is obtained by setting coefficient $\rho_2$ large, where $0 < \rho_1 < \rho_2 < 1$. By modeling these two components of the compliance process as stemming from two statistically independent random noise processes $u_1$ and $u_2$, better control of the relative amounts of the components is possible. The parameter $\alpha^2$ is used to control the relative amounts of contribution from each of the two random noise processes.

While the coefficients $\rho_1$ and $\rho_2$ may be obtained by guessing them using the above discussion as a guide, autocorrelation of compliance measurements may be used. As in previous discussion, it is recommended that the compliance data be detrended prior to estimating autocorrelation values. The applicable difference equation for the model of FIG. 8 using $\rho_1 = -a_1$ and $\rho_2 = -a_2$ is:

$$y(k) = (\rho_1 + \rho_2)y(k-1) - \rho_1 \rho_2 y(k-2) +$$

$$b_1(u_1(k-1) + u_2(k-1)) + \sum_{j=2}^{p} (b_j - \rho_2 b_{j-1}) u_1(k-j) +$$

$$(b_j - \rho_1 b_{j-1}) u_2(k-j) + v(k)$$

Using similar arguments as previously, for m>p−1:

$$r_{yy}(m) = (\rho_1 + \rho_2) r_{yy}(m-1) - (\rho_1 \rho_2) r_{yy}(m-2)$$

Letting successively m=p, p+1, . . . p+q−1, the following system of equations is obtained:

$$\begin{bmatrix} r_{yy}(p) \\ r_{yy}(p+1) \\ \vdots \\ r_{yy}(p+q-1) \end{bmatrix} = \begin{bmatrix} r_{yy}(p-1) & -r_{yy}(p-2) \\ r_{yy}(p) & -r_{yy}(p-1) \\ \vdots & \vdots \\ r_{yy}(p+q-2) & -r_{yy}(p+q-3) \end{bmatrix} \begin{bmatrix} \rho_1 + \rho_2 \\ \rho_1 \rho_2 \end{bmatrix}$$

This system may be solved for $\rho_1 + \rho_2$ and $\rho_1 \rho_2$ by methods described earlier, and then $\rho_1$ and $\sigma_2$ may be obtained.

Modeling Known Error Sources in the Measurement

In the HCLT, a known machine vibration can occur as a result of a wood board entering a bending span. Referring to FIG. 1, upper and lower rollers 1 pinch board 2 between them at six of the seven support points (all except the support at $x_4$). This allows motive force to be applied to the board in direction 3 by upper driven rollers 8. As a board enters between upper and lower rollers 1 at each of these six support points, the rollers are forced apart slightly. Vibration, which the inventor believes is excited by machine masses acting against compliance at support point contacts to the board, appears as a component of the measured compliance signal. The vibration can be modeled with an underdamped second order system modifying a time varying (nonstationary) white random noise source that is statistically independent of the other noise sources in the model.

Figure 9:
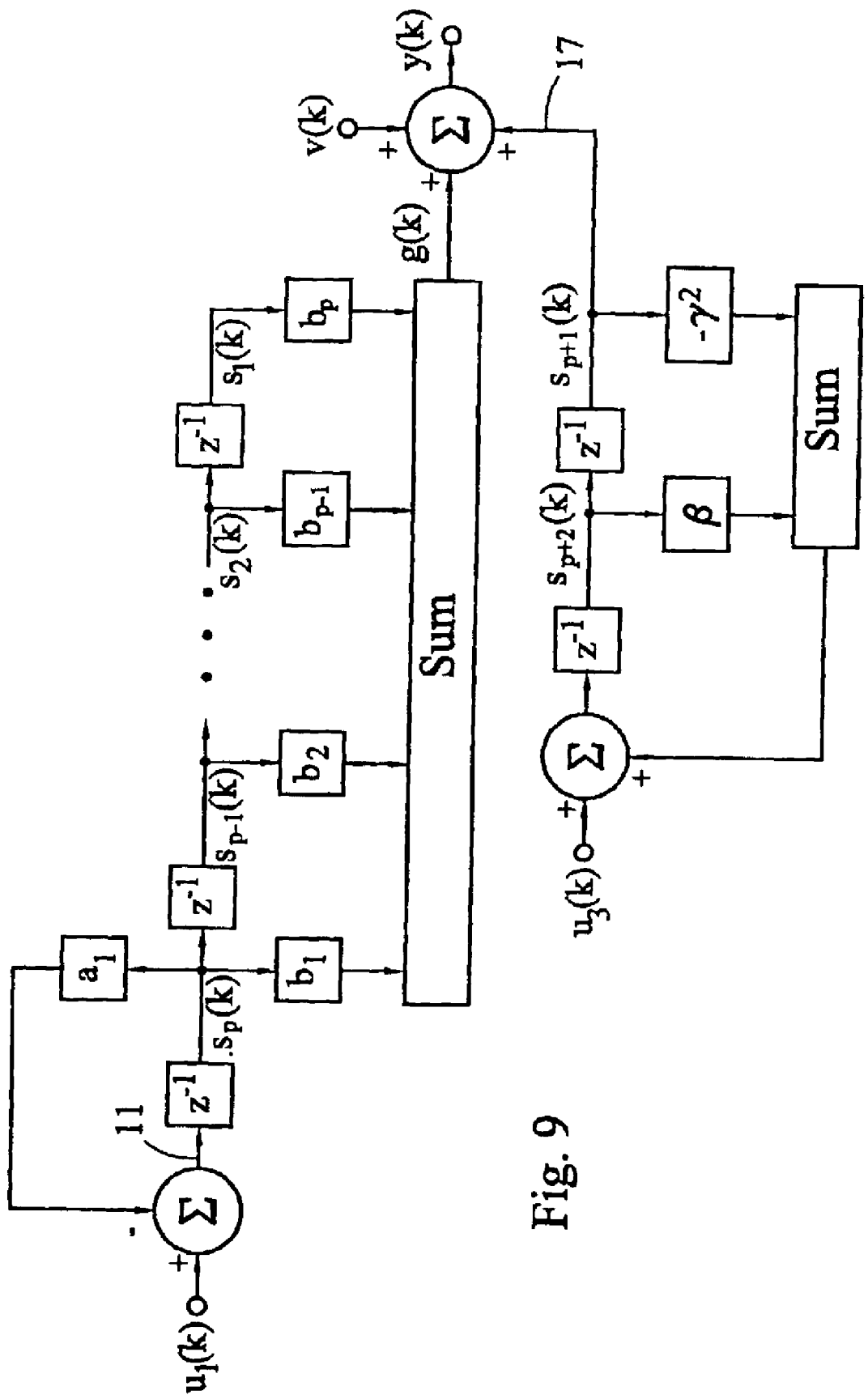
FIG. 9 is an ARMA model of the compliance measurement of FIG. 7 illustrating also the inclusion of modeling detail for one type of noise disturbance.

The two coefficients defining this second order system depend on the frequency observed and its damping. FIG. 9 illustrates a model similar to the one in FIG. 7, but with a second order system added. Standard sampled data methods (Oppenheim & Schafer, 1989) can be used to model this second order system with the coefficients $\beta$ and $-\gamma^2$.

For example, suppose that the observed vibration frequency when excited is 0.1 cycle/(inch travel of the board), or (0.1)(2.1866)=0.21866 cycle/sample or X=1.3739 radian/sample. Suppose that the vibration appears damped so that each successive peak has amplitude 0.9 times the previous peak. Then damping is 0.9/cycle or $\gamma$=0.9$^{0.21866}$=0.97723/sample. The coefficients $\beta$ and $-35^2$ are defined to show specifically how to express the frequency and damping in the model.

$$-\gamma^2=0.97723^2=-0.9550$$

$$\beta=2\gamma\cos(\omega)=(2\times 0.97723)\cos(1.3739)\ 0.3824$$

The state variable components $s_{p+1}(k)$ and $s_{p+2}(k)$ are appended to the state vector and contribute to the measurement through $s_{p+1}(k)$ at 17 as shown by the block diagram of FIG. 9. The state matrix, input vector, covariance matrix of the input vector, output matrix, and state vector are:

$$\phi = \begin{bmatrix} 0 & 1 & 0 & \ldots & 0 & 0 & 0 \\ 0 & 0 & 1 & \ddots & \vdots & \vdots & \vdots \\ \vdots & \vdots & \ddots & \ddots & 0 & 0 & 0 \\ 0 & 0 & \ldots & 0 & 1 & 0 & 0 \\ 0 & 0 & \ldots & 0 & -a_1 & 0 & 0 \\ 0 & 0 & & 0 & 0 & 0 & 1 \\ 0 & 0 & & 0 & 0 & -\gamma^2 & \beta \end{bmatrix}, \quad U(k) = \begin{bmatrix} 0 \\ \vdots \\ 0 \\ 0 \\ u_1(k) \\ 0 \\ u_3(k) \end{bmatrix},$$

$$Q(k) = \begin{bmatrix} 0 & \ldots & 0 & 0 & 0 & 0 & 0 \\ \vdots & \ddots & \vdots & \vdots & \vdots & & \vdots \\ 0 & \ldots & 0 & 0 & 0 & 0 & 0 \\ 0 & \ldots & 0 & 0 & \text{var}(u_1) & 0 & 0 \\ 0 & \ldots & 0 & 0 & 0 & 0 & 0 \\ 0 & \ldots & 0 & 0 & 0 & 0 & \text{var}(u_3(k)) \end{bmatrix}$$

$$H(k) = [b_p \ \ldots \ b_2 \ b_1 \ 1 \ 0],$$

$$s(k) = [s_1(k) \ \ldots \ s_p(k) \ s_{p+1}(k) \ s_{p+2}(k)]^T$$

A consistent initial covariance matrix for the state vector residual error is defined in partitioned form as:

$$P^* = \begin{bmatrix} \sigma_1^2 T & 0 \\ 0 & \sigma_3^2 T_3 \end{bmatrix}$$

The Toeplitz matrix T is defined as before, and:

$$\sigma_1^2 = \frac{\text{var}(u_1)}{(1-\rho^2)}, \quad \sigma_3^2(k) = \frac{(1+\gamma^2)\text{var}(u_3(k))}{(1-\gamma^2)[(1+\gamma^2)^2-\beta^2]}$$

$$T_3 = \begin{bmatrix} 1 & \frac{\beta}{(1+\gamma^2)} \\ \frac{\beta}{(1+\gamma^2)} & 1 \end{bmatrix}$$

It may be verified that P* satisfies the discrete Lyapunov equation.

Variances of the white noise inputs $u_1$ and $U_3$ are var($u_1$) and var($u_3(k)$) respectively. Because of the way that the vibration noise is excited, var($u_3(k)$) is nonstationary. For that reason the "k" has been retained in the notation; thereby allowing var($u_3(k)$) to be a function of board position. Then, in FIG. 1, as board 2 enters the space between an upper and lower pair of support rollers 1, var($u_3(k)$) can be increased for a short time representing a period of noise excitation.

The Kalman recursion can be applied as before, but with this model, some of the signal will be assigned to the vibration noise instead of to the compliance part of the state vector. The vibration component can be estimated as part of the method by observing the second to last component $s_{p+1}$ of the state vector. Estimation of sips can be useful in determining machine performance and need for maintenance.

The models of FIGS. 6, 7, 8, and 9 suggest some of the possibilities for the new method; although these models do not exhaust the possibilities.

Test Results

Tests using the new method were performed for both simulated and real data. The reduced model of FIG. 7 was used. To check its robustness against the quality of a priori information of the autoregressive coefficient $a_1=-\rho$, two different values were used. The first value $\rho_b$ was used to generate local compliance values for simulated boards according to the autoregressive model of the upper left part of FIG. 7. The second value $\rho_a$ was used with Kalman filter processing. It can be argued that the same value should be used in both places, but it can also be argued that the underlying value may not be known accurately. One can think of Pb as defining the board and $\rho_a$ as defining the analysis. Ideally, the board value $\rho_b$ would be known and the analysis would make use of that known value. Experimentation has shown that the method is robust over a range of analysis values $\rho_a$, and that there may be some benefit in allowing $\rho_a$ to be smaller than it is believed to be.

Using 0.5 (106 psi)$^{-1}$ for mean compliance value and 0.4 for coefficient of variation of compliance value, the variance for local compliance values is 0.04 (10$^6$ psi)$^{-2}$. Then, the variance of the white noise random process u(k) in FIG. 7 is given by var(u)=$\sigma^2$(1=$\sigma_b^2$). The zero mean white noise process u(k) variates were generated from a lognormal pseudorandom number generator adjusted to have zero mean and variance var(u)=$\sigma^2$(1−$\rho_b^2$)=0.04 (1=$\rho_b^2$) (10$^6$ psi)$^{-2}$. The lognormal distribution was used because it provides a lower limit of generated variates. Then, when the mean is added to provide simulated local compliance values C, the reciprocal E=1/C values are neither extraordinarily large nor negative. By this method, simulated local compliance functions were generated. However, in an effort to better simulate knots, compliance pulses were added at defined points. Three compliance pulses having amplitude equal to twice the mean compliance value were added to the generated local compliance function sample values at 53.6, 108.2, and 119.2 inch from the leading end of the simulated board. Also, a compliance pulse with twice the mean compliance amplitude was added to adjacent generated samples of the local compliance function at 162.9 and 165.1 inch, giving a pulse two samples wide.

Figure 10:
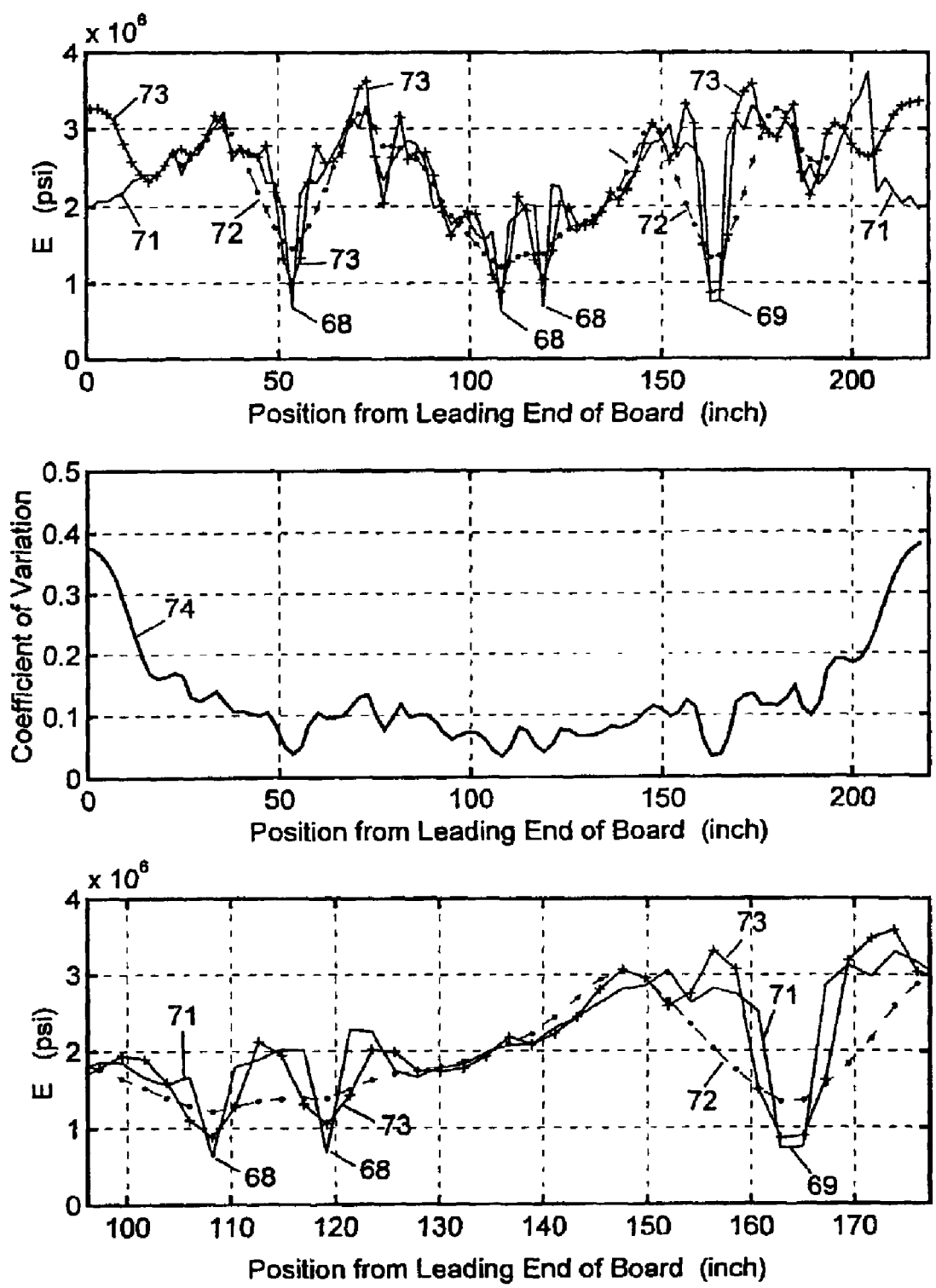
FIG. 10 is a graph showing results of optimal estimation of local compliance; graphed results show the reciprocal modulus of elasticity values, for a simulated wood board including compliance pulses to simulate knots.

E, which is the reciprocal of C for one sample outcome function generated in this way with $\rho_b$=0.97 is shown by the solid line and labeled 71 in the upper part of FIG. 10. The reciprocal is presented because that is more familiar to those working in the field. The relative minima in E corresponding to the pulses in compliance are labeled 68 for the single sample pulses and 69 for the two sample wide pulse. An expanded version of the plot for part of the domain is illustrated in the lower part of FIG. 10 to show more detail. To simulate bending measurement by an HCLT, the simulated local compliance function C was convolved with weights from a succession of output matrices H1, H2, H3, H4, and H5 as previously described. Then, the measured compliance function $C_m$ was obtained by adding pseudo-random white noise from a Gaussian distribution having zero mean and variance given by var(v)=0.00001($10^6$ psi)$^{-2}$ to simulate HCLT measurement noise. $E_m$, which is the reciprocal of $C_m$, is shown as the dashed line with dots and labeled 72 in FIG. 10. The curve 72 is observed to be a smoothed version of 71 and misses much of the detail of 71 as is expected with a bending measurement.

The coefficient $\rho_a$=0.9 was entered in the definition of input noise covariance matrix Q and state matrix $\phi$ for the dynamic system model for use with the Kalman filter. Thus, for the Kalman filter, the input noise covariance matrix Q was defined with $\rho_a$=0.9 in var(u)=$\sigma^2(1-\rho_a^2)$=0.0076 ($10^6$ psi)$^{-2}$ instead of $\rho_b$=0.97. Measurement noise variance used by the Kalman filter was defined to be var(v)=0.00001($10^6$ psi)$^{-2}$. The Kalman filter steps were applied to simulated measured compliance $C_m$ as taught in this specification. The resulting estimated local compliance function C* and coefficient of variation $COV_C$ were thereby obtained. The corresponding estimated E*, and $COV_E$ were obtained from:

$$E^*=(1+COV_C^2)/C^* \text{ and } COV_E=COV_C/(1+COV_C^2)$$

The function E is shown by the solid line with pluses and labeled 73 in FIG. 10. The coefficient of variation COVE is plotted and labeled 74 in the center part of FIG. 10.

The results of this process were studied for many other combinations of $\rho_a$ and $\rho_b$. As expected, reduced values of $\rho_b$ result in more rapid changes of the simulated local compliance function because adjacent values are not correlated as well. It was observed that values of $\rho_a$ close to one, e.g. p, =0.999, cause the estimated compliance function C* to closely track the measured compliance function Cm, and hence cause E* to closely track $E_m$. It is the goal of the present specification for E* to closely track E. As $\rho_a$ is reduced, E* was observed to follow the relative minima (dips) in the local function E more accurately. Note, e.g. in FIG. 10 where $\rho_a$ =0.9, that E*, curve 73, follows the dips in local E, curve 71, considerably better than does measured $E_m$, curve 72. It was observed that E* can have some extraneous excursions upward if $\rho_a$ is reduced too much. However, it was also observed that E* followed the dips in E caused by the four compliance pulses even better when $\rho_a$ is smaller than 0.9.

It was unexpected that the new method using the reduced ARMA model of FIG. 7 was able to perform as well as it did when knots were simulated with compliance pulses. The capability of this simple model is enhanced in the tracking of dips in E when $\rho_a$ is small. It is clear by comparing the estimated local function 73 with the actual local function 71 in the upper plot of FIG. 10, that estimation quality decreases near the board ends. This is also evident from the center plot of FIG. 10, which shows that the estimator coefficient of variation 74 increases near the board ends.

More experiments and adjustments are possible with simulated data. For example either the two input model of FIG. 8 or the ARMA model of FIG. 6 with more autoregressive coefficients may better model and track the effects of knots than the reduced ARMA model of FIG. 7.

To test the method with real data, measured compliance data from a 2×6 wood board were gathered from an HCLT, and the new method using the reduced ARMA model of FIG. 7 was applied. The local compliance variance was modeled by $\sigma^2$=0.04 ($10^6$ psi)$^{-2}$. The autoregressive coefficient $\rho_a$=0.9 was assumed in defining the variance var(u)=$\sigma^2$ $(1\rho_a^2)$=0.0076($10^6$ psi)$^{-2}$ in the matrix Q. The coefficient $\rho_a$=0.9 was used also in the state matrix $\phi$. Measurement noise variance was taken as var(v)=0.00001($10^6$ psi)$^{-2}$.

Figure 11:
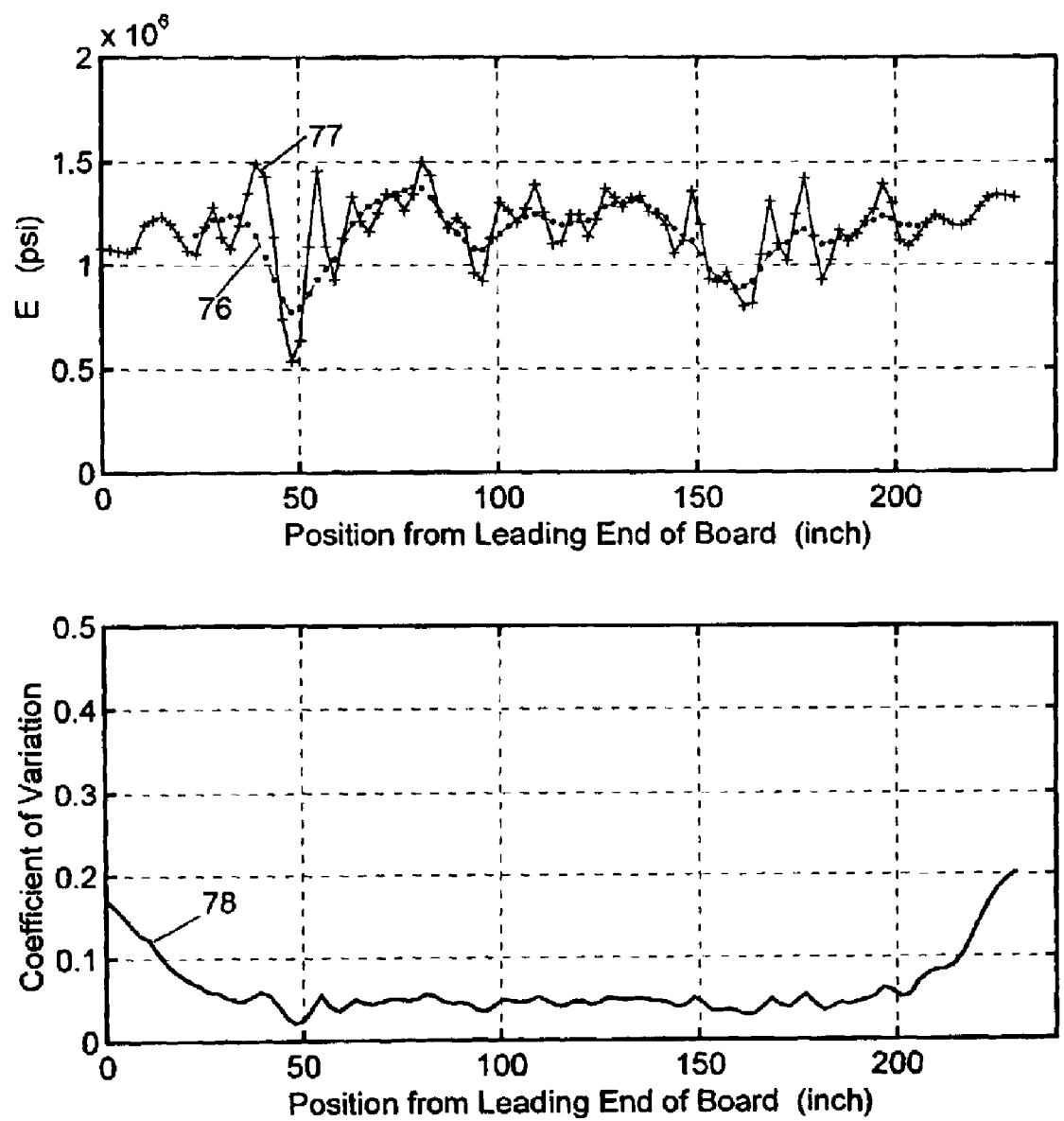
FIG. 11 is a graph showing results of optimal estimation of local compliance, graphed results show reciprocals, obtained from HCLT bending compliance measurements of a 2×6 wood board.

The upper part of FIG. 11 shows measured $E_m$ from the HCLT as the curve marked with dots and labeled 76. The estimated local function E* was obtained as above and is shown with the curve marked with pluses and labeled 77. The underlying local function E is unknown, and so comparison between it and the estimated function E* is not possible. Coefficient of variation of E* is shown by the curve marked 78 in the lower part of FIG. 11.

Beam Categorization System Using the New Method

The preferred embodiment description shows how measurements can be processed using span functions to yield estimates of local properties along a beam. Kalman filtering allows processing of vector measurements. Each vector component is a sequence of measurements, and each measured component helps in the estimation of local compliance. This format is useful as well in estimation of other beam properties of importance in grading beams. The Kalman filter provides efficient and concise means of organizing and processing data to make best use of statistical information about the data and a priori information.

Additional Kalman filters are defined that work in parallel to process separate additional component measured data sequences, each with its own state-space representation. Alternatively, one grand Kalman filter is defined to operate on a vector measurement sequence. In either case, one Kalman filter will suffice. Uncoupled sets of state variables operate independently and in parallel within the filter. Coupling among some of the state variables representing different measurement sequences is readily handled with a larger state matrix that defines the coupling. In the state-space dynamic system model, the state variables are appended, thereby extending the length of the state vector. Uncoupled systems are handled in parallel by matrix partitioning and coupled systems require larger matrices.

Figure 19:
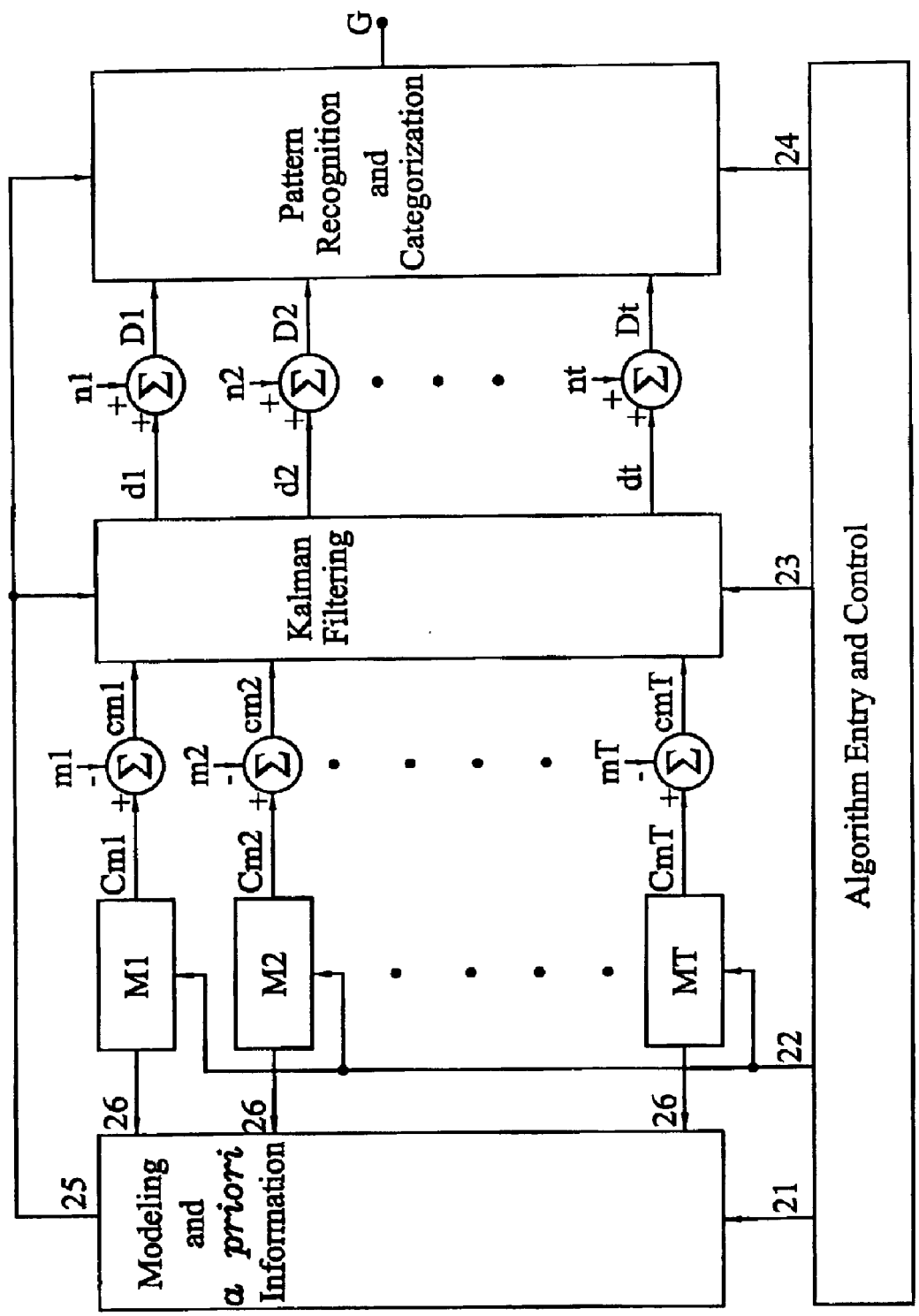
FIG. 19 is a block diagram illustrating a system for beam categorization using a plurality of measurements.

FIG. 19 illustrates a general system block diagram where the multiple measurement sequences Cm1, Cm2, . . . , CmT are used. In keeping with application of Kalman filtering, estimates of means m1, m2, . . . , mT are subtracted from the data before processing by the filter. The blocks labeled M1, M2, . . . , MT represent measuring apparatus controlled by a common Algorithm Entry and Control unit through the line labeled 22. The block labeled Modeling and a priori Information accepts information from the measurement apparatus through lines 26 and from the Algorithm Entry and Control unit through line labeled 21. The purpose of the Modeling block is to provide information to the Kalman filter and to the Pattern Recognition and Categorization block through line 25. This information includes span functions, output matrix coefficients, state matrix components and initialization information some used by the Kalman filter and some by the Pattern Recognition and Categorization block. Processing algorithms and control are provided to these latter units through lines labeled 23 and 24.

Outputs d1, d2, . . . , dt from the Kalman filter are sequences of estimated local values as in local compliance estimation, and in some cases are single parameter estimates for the beam, e.g. its average density. The number of Kalman filter outputs t in FIG. 19 typically will not correspond with the number of inputs T, as some of the inputs are processed by the Kalman filter to give one output. For example, if the HCLT signals from its two bending sections are treated as the separate Kalman input measurement sequences cm1 and cm2, there is good reason to define the model using a common state vector and provide a single sequence of estimated local compliance estimates. In that case d1 is a sequence of estimated local compliance values, the estimated means m1 and m2 are the first measured compliance values from the first and second bending sections, respectively, and n1 is the average of m1 and m2.

Other measurement sequences can include grain angle and other dielectric property measurements, x or gamma ray transmission measurements, and optical property measurements. State-space modeling and use of Kalman filtering for these measurements similar to the effort for compliance will improve estimation resolution and accuracy as it does for local compliance. For measurements not amenable to a reasonable model as is available for compliance, the Kalman filter can simply pass through the measurements, and the measurement sequences treated as direct input to the Pattern Recognition and Categorization unit. The Pattern Recognition and Categorization block processes its inputs including outputs from the Kalman filter and modeling and a priori information to define manufacturing, processing, or use of a beam for increased value. The output of this step can be a grade category labeled as G in FIG. 19.

It is clear that the preferred embodiment is a subset of FIG. 19. The measurement apparatus measures compliance along wood boards with an HCLT represented by the block labeled M1, and the measurement sequence is $C_m$ labeled Cm1 in FIG. 19. The subtracted mean estimate is $C_m(12)$, the initial beam compliance measurement labeled m1 in FIG. 19. The Kalman filter uses the state-space model provided by the Modeling and apriori Information block and includes all the matrices and initialization required to apply the Kalman filter. The Kalman output is the demeaned estimated local compliance sequence c* labeled d1 in FIG. 19. To this is added $C_m(12)$ labeled a1 to obtain the local compliance sequence C* labeled D1. The estimated local compliance sequence is used as input to the Pattern Recognition and Categorization block which determines the grade for the board.

Present art is a special case where no Kalman filtering is applied, and the measurement sequence $E_m$ is passed straight through to the Pattern Recognition and Categorization block, which uses the average and lowest values of the measured MOE sequence $E_m$ and bases the grade on those two numbers using thresholds and other information available from the Modeling a priori Information block A first approach for categorization with FIG. 19 improves on the present art by basing the grade on the average and the highest of the local compliance measurements C*.

Alternative Embodiments

Span functions are used in the determination of output matrices for the model of the estimation method. The following alternative embodiment examples illustrate generality of span function computation taught in this specification. This generality allows application of the new method to a broad class of problems involving bending measurements of beams.

For the preferred and alternative embodiments, measured compliance is a composite measurement, local compliance values comprise the unknown components, and a span function weights them into the measurement. The Kalman recursion has the same framework and steps when used with the alternative embodiments as for the preferred embodiment, and is not discussed further. Details of span function computation are provided because of differences from the preferred embodiment that may not be obvious.

Fit Alternative Embodiment—Three Supports

Consider a simple three-support example wherein a load is placed midway between two end supports, and deflection is measured at the midway point. Referring to FIG. 2, this would be the case for n=3, where $x_1=-L/2$, $x_2=0$, and $x_3=L/2$; $L=X_3-X_1$ being the length of the bending span. The reference 5 is at x=0, the location of the support at $x_2$. For this commonly used special case, the span function h(x) has been obtained by a previously disclosed method (Bechtel, 1985). The computation for this simple case according to the general procedure taught herein lends credence to the correctness of the general procedure, as well as serving as an example.

Typically, in machines represented by this example (and in others), to reduce errors from alignment discrepancies and non-linearity at small loads and deflections, an initial load or an initial deflection is applied. This does not affect the procedure if the deflection and force zero references arm taken as the initial values.

Following procedures of this specification, the matrices $W_o$ and $W_d(x)$ are:

$$W_o = \begin{bmatrix} \frac{C_o L^3}{48} & 0 & 0 & \frac{L}{2} \\ \frac{C_o L^3}{6} & \frac{C_o L^3}{48} & 0 & L \\ 1 & 1 & 1 & 0 \\ L & \frac{L}{2} & 0 & 0 \end{bmatrix}, \quad W_d(x) = \begin{bmatrix} d_{12}(x) & 0 & 0 & 0 \\ d_{13}(x) & d_{23}(x) & 0 & 0 \\ 0 & 0 & 0 & 0 \\ 0 & 0 & 0 & 0 \end{bmatrix}$$

It us recalled that WA=B where $W=W_o+bW_d(x)$ defines a matrix equation from which the span function is derived.

The inverse of $W_o$ is:

$$W_o^{-1} = \frac{48}{C_o L^3} \begin{bmatrix} -\frac{1}{2} & \frac{1}{4} & 0 & -\frac{C_o L^2}{96} \\ 1 & -\frac{1}{2} & 0 & \frac{3C_o L^2}{48} \\ -\frac{1}{2} & \frac{1}{4} & \frac{C_o L^3}{48} & -\frac{5C_o L^2}{96} \\ \frac{3C_o L^2}{48} & -\frac{C_o L^2}{96} & 0 & \frac{C_o^2 L^4}{48^2} \end{bmatrix}$$

As before, the span function is computed as a partial derivative of the measured compliance for a beam with local compliance being a test function having constant background compliance plus a compliance impulse at position x relative to the span reference. The derivative is taken with respect to the impulse weight b and is evaluated at b=0 for each impulse location that can affect the measurement.

$$h(x) = \left. \frac{\partial C_m(b, x)}{\partial b} \right|_{b=0}$$

$$= C_o \frac{\{W_o^{-1} W_d(x) W_o^{-1} B\}_2}{\{W_o^{-1} B\}_2}, \quad x_1 < x \leq x_3$$

In this case, it is easy to show that the forces are related by $F_1=F_3=-F_2/2$. The $W_d(x)$ matrix has only zeros in its last column, and only the second component of force is used; hence computation of $W_o^{-1}B$ may be avoided by replacing it with $A=[F_1, F_2, F_3, S_1]^T$ without needing to compute $S_1$. The second components of the vectors in braces are used because loads are applied and deflections are measured at the second support. The span function is:

$$h(x) = C_o \frac{\{W_o^{-1} W_d(x) \Delta\}_2}{\{\Delta\}_2}, \quad x_1 < x \le x_3$$

Only the second component of the numerator vector enclosed in braces { } is required; hence, only the second row of $W_o^{-1} W_d(x)$ need be computed. The result is:

$$h(x) = \begin{cases} C_o\left(\frac{48}{C_o L^3}\right)\left[(-x)(x+L/2) - \frac{1}{2}(L/2-x)(x+L/2)\right]\left(\frac{F_1}{F_2}\right), & -L/2 < x \le 0 \\ C_o\left(\frac{48}{C_o L^3}\right)\left(-\frac{1}{2}\right)\left[(L/2-x)(x+L/2)\left(\frac{F_1}{F_2}\right) + (L/2-x)(x)\left(\frac{F_2}{F_2}\right)\right], & 0 < x \le L/2 \end{cases}$$

$$= \begin{cases} \left(\frac{12}{L^3}\right)(L/2 - |x|)^2, & -L/2 < x \le L/2 \\ 0, & \text{otherwise} \end{cases}$$

Figure 13:
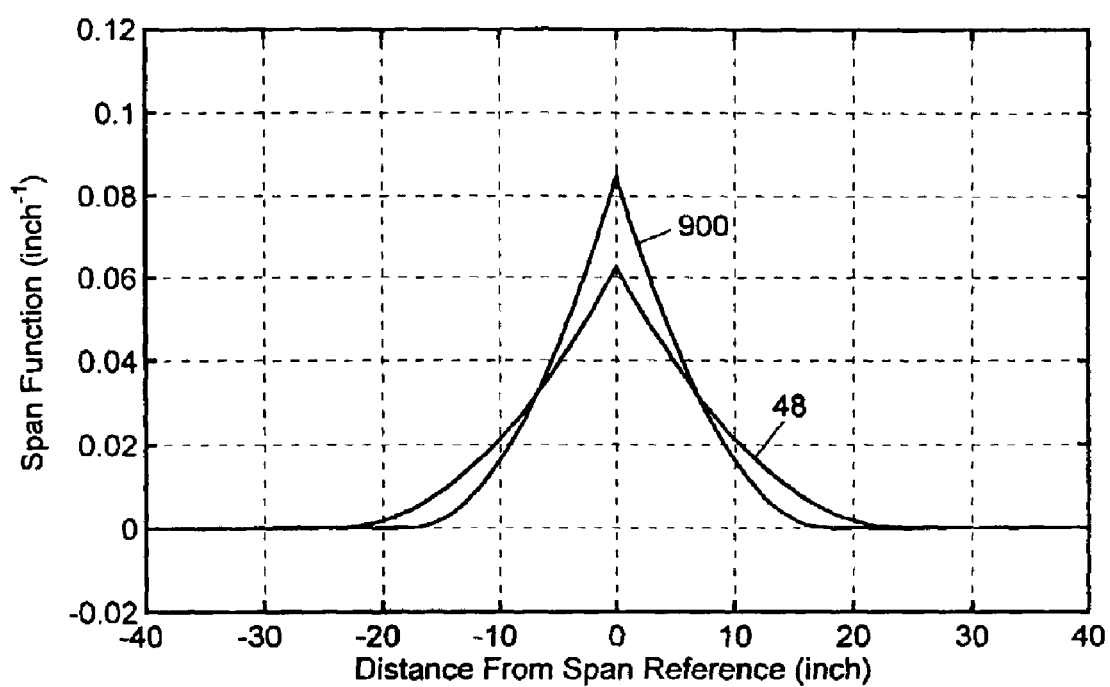
FIG. 13 (prior art) shows, for two different bending span lengths, span functions for three-support, center-loaded bending spans.

This agrees with the prior art and is plotted in FIG. 13 for L=48 inch, labeled 48 and for L=900 mm, labeled 900. FIG. 13 is plotted on the same scale as FIG. 3 so comparisons can be made.

Second Alternative Embodiment—Four Supports (Equally Loaded at Third Points)

Figure 14:
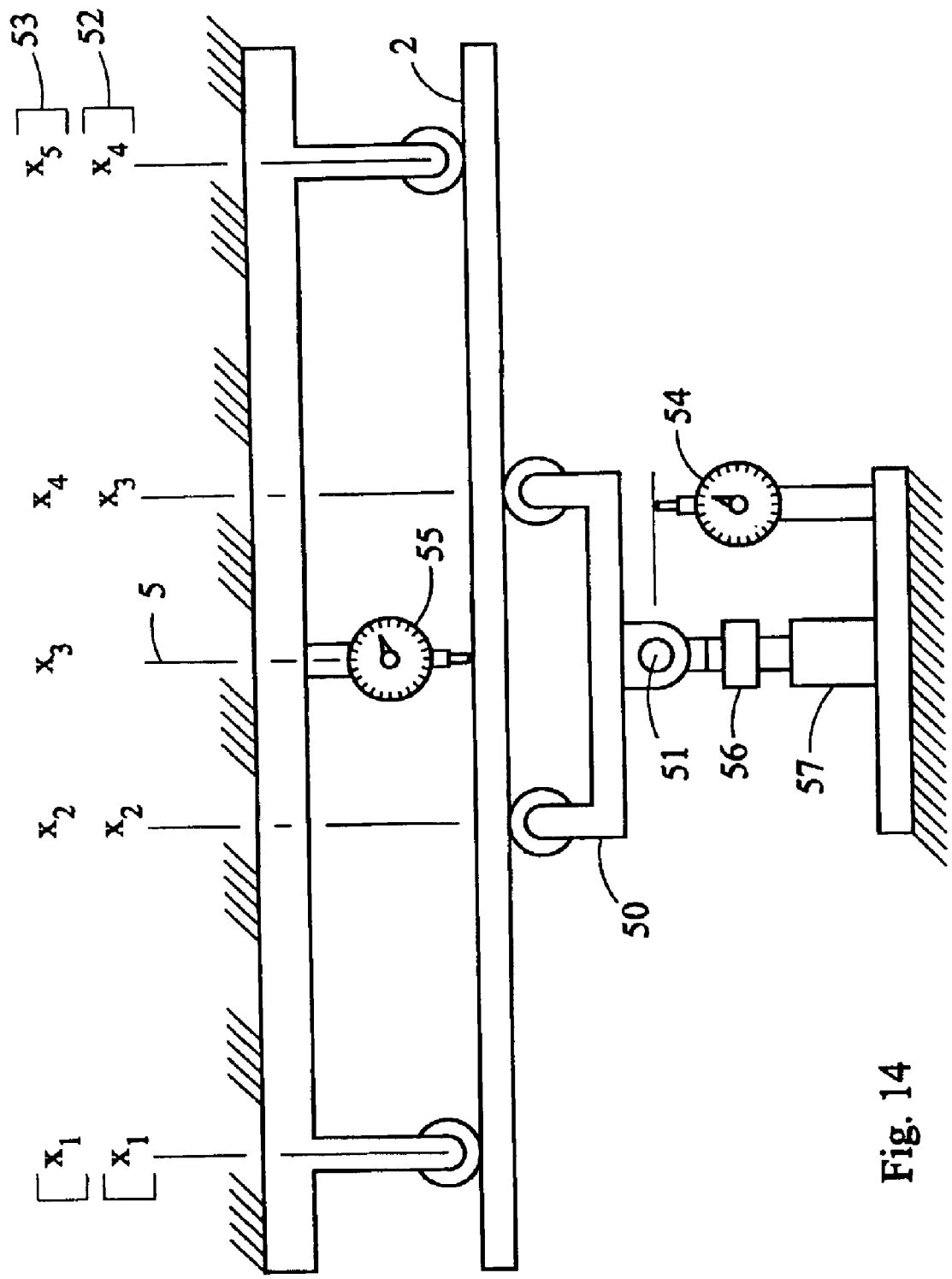
FIG. 14 is a mechanical schematic illustrating two versions of machinery often used for quality control of stress rated lumber.

As another practical example, and to demonstrate another detail, consider a four-support bending span where loads are applied at the "third points" as shown schematically in FIG. 14. This configuration is often used for off-line quality control testing of lumber. A feature of this apparatus is its load-spreading beam 50, which, through fulcrum 51, causes the loads applied by beam 50 to beam 2 to be equal at two support points. As with the first alternative embodiment, deflections and forces are referenced from preload values. The bending span reference 5 is midway in the bending span. In this example, there is no support located at the reference position 5. In FIG. 2, illustrating the general situation, the number of supports is n=4 for this example, and the support locations relative to the reference 5 are $x_1 = -L/2$, $x_2 = -L/6$, $x_3 = L/6$, and $x_4 = L/2$. L is the length of the span so that $L = x_4 - x_1$. This set of support conditions is indicated by 52 in FIG. 14.

Two versions of this machine have been used in the quality control of MSR lumber produced in North America, and their span functions are different. Both versions are represented by FIG. 14. In the first version of the machine, deflection is measured by sensing means 54 at fulcrum 51 of the load-spreading beam 50. Neglecting the possibility of flexure in the load-spreading beam 50, the deflection at fulcrum 51 is equivalent to the average of beam 2 deflections at the second and third support points $x_2$ and $x_3$ as identified by support location set 52. In the second version of the machine, deflection of beam 2 is measured by sensing means 55 at the center of the bending span, i.e. at reference 5 where no support exists. Analysis for the second version of the machine defines a support at center span having zero force; the support location set for the second version is identified by 53 in FIG. 14. In this second version, equal loads are applied by beam 50 to beam 2 at third point support locations $x_2$ and $x_4$ identified in support location set 53.

For the bending span configuration of the first version of this machine, where the average of deflections at $x_2$ and $x_3$ in support set 52 is measured or controlled, computations are straightforward and proceed similarly to previous examples. The span function is computed from:

$$h(x) = C_o \frac{\{W_o^{-1} W_d(x) \Delta\}_{2+3}}{\{\Delta\}_{2+3}}$$

$$= C_o \frac{\{W_o^{-1} W_d(x) \Delta\}_{2+3}}{\{\Delta\}_{2+3}}, \quad x_1 < x \le x_4$$

The brace notation in the formula is defined so that in each of the numerator and denominator, it represents the sum of the second and third components of the vector enclosed by the braces. This sum is what the apparatus sees at the fulcrum 51 in its measurement of force, e.g. by load cell 56. Force can be applied by hydraulic ram 57. Thus, the denominator is $\{\Delta\}_{2+3} = F_2 + F_3$. The span function numerator is computed for each point x of interest, noting that the components of A satisfy $-F_1 = F_2 = F_3 = -F_4$. The last component of A, namely the slope $S_1$, doesn't matter in the computation of h(x) because the entire last column of $W_d(x)$ is zero. Only the second and third components of the braced numerator vector need be computed and then added together at each x for which the span function h(x) is computed. The span function computed from the above operations is given here and illustrated in FIG. 15 as curve 40.

$$h(x) = \begin{cases} \frac{9}{5L}, & |x| \le L/6 \\ \frac{81}{5L^3}\left(\frac{L}{2} - |x|\right)^2, & L/6 < |x| \le L/2 \\ 0, & \text{otherwise.} \end{cases}$$

The second version of the machine adds a complication, but is useful in demonstrating the versatility of the method. To account for deflection measurement or control at the center of the bending test span, the machine is considered as having another support at that point, but with zero force. The resulting bending span then has five support points, as represented in FIG. 14 by the upper set of support locations labeled 53. The equations WA=B, when expanded become:

$$\begin{bmatrix} I_{12} & 0 & 0 & 0 & 0 & x_2 - x_1 \\ I_{13} & I_{23} & 0 & 0 & 0 & x_3 - x_1 \\ I_{14} & I_{24} & I_{34} & 0 & 0 & x_4 - x_1 \\ I_{15} & I_{25} & I_{35} & I_{45} & 0 & x_5 - x_1 \\ 1 & 1 & 1 & 1 & 1 & 0 \\ x_5 - x_1 & x_5 - x_2 & x_5 - x_3 & x_5 - x_4 & 0 & 0 \end{bmatrix} \begin{bmatrix} F_1 \\ F_2 \\ F_3 \\ F_4 \\ F_5 \\ S_1 \end{bmatrix} = \begin{bmatrix} D_2 \\ D_3 \\ D_4 \\ 0 \\ 0 \\ 0 \end{bmatrix}$$

where the end support deflections $D_1$ and $D_2$ and end shear forces and moments are assumed to be zero. These equations are still quite general for five supports. They are specialized for this case by requiring that the forces $F_2$ and $F_4$ applied by the load bean be each equal to half their sum defined as F, and by setting the force $F_3$ to zero:

$$F_2=F/2, F_4=F/2, F_3=0 \qquad 5$$

Because the deflections $D_2$ and $D_4$ are neither measured nor controlled, they along with $D_3$ are repositioned on the left side of the equations. The measured force F is moved to the right side. In two steps, this reorganization yields:

$$\begin{bmatrix} I_{12} \\ I_{13} \\ I_{14} \\ I_{15} \\ 1 \\ x_5-x_1 \end{bmatrix} F_1 + \begin{bmatrix} 0 \\ I_{23} \\ I_{24} \\ I_{25} \\ 1 \\ x_5-x_2 \end{bmatrix}(F/2) + \begin{bmatrix} 0 \\ 0 \\ 0 \\ I_{45} \\ 1 \\ x_5-x_4 \end{bmatrix}(F/2) + \begin{bmatrix} 0 \\ 0 \\ 0 \\ 0 \\ 1 \\ 0 \end{bmatrix} F_5 + \begin{bmatrix} x_2-x_1 \\ x_3-x_1 \\ x_4-x_1 \\ x_5-x_1 \\ 0 \\ 0 \end{bmatrix} S_1 +$$

$$\begin{bmatrix} -1 \\ 0 \\ 0 \\ 0 \\ 0 \\ 0 \end{bmatrix} D_2 + \begin{bmatrix} 0 \\ -1 \\ 0 \\ 0 \\ 0 \\ 0 \end{bmatrix} D_3 + \begin{bmatrix} 0 \\ 0 \\ -1 \\ 0 \\ 0 \\ 0 \end{bmatrix} D_4 = \begin{bmatrix} 0 \\ 0 \\ 0 \\ 0 \\ 0 \\ 0 \end{bmatrix}$$

$$\begin{bmatrix} -1 \\ 0 \\ 0 \\ 0 \\ 0 \\ 0 \end{bmatrix} D_2 + \begin{bmatrix} 0 \\ -1 \\ 0 \\ 0 \\ 0 \\ 0 \end{bmatrix} D_3 + \begin{bmatrix} 0 \\ 0 \\ -1 \\ 0 \\ 0 \\ 0 \end{bmatrix} D_4 + \begin{bmatrix} I_{12} \\ I_{13} \\ I_{14} \\ I_{15} \\ 1 \\ x_5-x_1 \end{bmatrix} F_1 +$$

$$\begin{bmatrix} 0 \\ 0 \\ 0 \\ 0 \\ 1 \\ 0 \end{bmatrix} F_5 + \begin{bmatrix} x_2-x_1 \\ x_3-x_1 \\ x_4-x_1 \\ x_5-x_1 \\ 0 \\ 0 \end{bmatrix} S_1 = \begin{bmatrix} 0 \\ -I_{23}/2 \\ -I_{24}/2 \\ -(I_{25}+I_{45})/2 \\ -1 \\ -x_5+(x_2+x_4)/2 \end{bmatrix} F$$

which can be written:

$$\begin{bmatrix} -1 & 0 & 0 & I_{12} & 0 & x_2-x_1 \\ 0 & -1 & 0 & I_{13} & 0 & x_3-x_1 \\ 0 & 0 & -1 & I_{14} & 0 & x_4-x_1 \\ 0 & 0 & 0 & I_{15} & 0 & x_5-x_1 \\ 0 & 0 & 0 & 1 & 1 & 0 \\ 0 & 0 & 0 & x_5-x_1 & 0 & 0 \end{bmatrix} \begin{bmatrix} D_2 \\ D_3 \\ D_4 \\ F_1 \\ F_5 \\ S_1 \end{bmatrix} = \begin{bmatrix} 0 \\ -I_{23}/2 \\ -I_{24}/2 \\ -(I_{25}+I_{45})/2 \\ -1 \\ -x_5+(x_2+x_4)/2 \end{bmatrix} F$$

where now:

$$W = \begin{bmatrix} -1 & 0 & 0 & I_{12} & 0 & x_2-x_1 \\ 0 & -1 & 0 & I_{13} & 0 & x_3-x_1 \\ 0 & 0 & -1 & I_{14} & 0 & x_4-x_1 \\ 0 & 0 & 0 & I_{15} & 0 & x_5-x_1 \\ 0 & 0 & 0 & 1 & 1 & 0 \\ 0 & 0 & 0 & x_5-x_1 & 0 & 0 \end{bmatrix}, A = \begin{bmatrix} D_2 \\ D_3 \\ D_4 \\ F_1 \\ F_5 \\ S_1 \end{bmatrix},$$

$$B = \begin{bmatrix} 0 \\ -I_{23}/2 \\ -I_{24}/2 \\ -(I_{25}+I_{45})/2 \\ -1 \\ -x_5+(x_2+x_4)/2 \end{bmatrix}$$

and F is the scalar force $F=F_2+F_4$, which is measured at 56. The calibration factor K is obtained from:

$$C_o = K\frac{D_3}{F}$$

for the case where the beam has constant value $C_o$, and where $D_3=\{A\}_2$, which is the deflection of the beam at span center as measured by sensor 55. To compute h(x), the local beam compliance is defined as the test function consisting of a constant $C_o$ plus an impulse of weight b. Before taking the derivative to obtain the span function, the matrix W and vector B are each decomposed into the sum of two parts, the first part from the constant $C_o$ and the second from the impulse:

$$W = W_o + bW_d(x)$$

$$B = B_o + bB_d(x)$$

where:

$$W_o = \begin{bmatrix} -1 & 0 & 0 & C_o(x_2-x_1)^3/6 & 0 & x_2-x_1 \\ 0 & -1 & 0 & C_o(x_3-x_1)^3/6 & 0 & x_3-x_1 \\ 0 & 0 & -1 & C_o(x_4-x_1)^3/6 & 0 & x_4-x_1 \\ 0 & 0 & 0 & C_o(x_5-x_1)^3/6 & 0 & x_5-x_1 \\ 0 & 0 & 0 & 1 & 1 & 0 \\ 0 & 0 & 0 & x_5-x_1 & 0 & 0 \end{bmatrix},$$

$$B_o = \begin{bmatrix} 0 \\ -C_o(x_3-x_2)^3/12 \\ -C_o(x_4-x_2)^3/12 \\ -C_o((x_5-x_2)^3+(x_5-x_4)^3)/12 \\ -1 \\ -x_5+(x_2+x_4)/2 \end{bmatrix}$$

$$W_d(x) = \begin{bmatrix} 0 & 0 & 0 & d_{12}(x) & 0 & 0 \\ 0 & 0 & 0 & d_{13}(x) & 0 & 0 \\ 0 & 0 & 0 & d_{14}(x) & 0 & 0 \\ 0 & 0 & 0 & d_{15}(x) & 0 & 0 \\ 0 & 0 & 0 & 0 & 0 & 0 \\ 0 & 0 & 0 & 0 & 0 & 0 \end{bmatrix},$$

$$B_d(x) = \begin{bmatrix} 0 \\ -d_{23}(x)/2 \\ -d_{24}(x)/2 \\ -(d_{25}(x)+d_{45}(x))/2 \\ 0 \\ 0 \end{bmatrix}$$

and, as previously:

$$d_{ij}(x) = \begin{cases} (x_j - x)(x - x_i), & x_i < x \leq x_j \\ 0, & \text{otherwise} \end{cases}$$

The span function is:

$$h(x) = \frac{\partial C_m(b,x)}{\partial b}\bigg|_{b=0} = \lim_{b \to 0} \frac{C_m(b,x) - C_o}{b}$$

$$= \lim_{b \to 0} \frac{1}{b}\left[\frac{K\{W^{-1}B\}_2 F}{F} - \frac{K\{W_o^{-1}B_o\}_2 F}{F}\right]$$

$$= \lim_{b \to 0} \frac{K}{b}[\{W^{-1}B\}_2 - \{W_o^{-1}B_o\}_2]$$

$$= \lim_{b \to 0} \frac{K}{b}[\{(W_o + bW_d)^{-1}(B_o + bB_d(x))\}_2 - \{W_o^{-1}B_o\}_2]$$

$$= \lim_{b \to 0} \frac{K}{b}[\{(1 + bW_o^{-1}W_d)^{-1}(W_o^{-1}B_o + bW_o^{-1}B_d(x))\}_2 - \{W_o^{-1}B_o\}_2]$$

$$= \lim_{b \to 0} \frac{K}{b}[\{(1 - bW_o^{-1}W_d)(W_o^{-1}B_o + bW_o^{-1}B_d(x))\}_2 - \{W_o^{-1}B_o\}_2]$$

$$= \lim_{b \to 0} \frac{K}{b}[\{-bW_o^{-1}W_d W_o^{-1}B_o + bW_o^{-1}B_d(x) - b^2 W_o^{-1}W_d W_o^{-1}B_d(x)\}_2]$$

$$= K[\{-W_o^{-1}W_d W_o^{-1}B_o + W_o^{-1}B_d(x)\}_2]$$

$$= C_o \frac{\{-W_o^{-1}W_d W_o^{-1}B_o + W_o^{-1}B_d(x)\}_2}{\{W_o^{-1}B_o\}_2}, \quad x_1 < x \leq x_5$$

With $L = X_5 - x_1$, the inverse of $W_o$ is:

$$W_o^{-1} = \begin{bmatrix} -1 & 0 & 0 & (x_2-x_1)/L & 0 & C_o(x_2-x_1)[(x_2-x_1)^2 - L^2]/(6L) \\ 0 & -1 & 0 & (x_3-x_1)/L & 0 & C_o(x_3-x_1)[(x_3-x_1)^2 - L^2]/(6L) \\ 0 & 0 & -1 & (x_4-x_1)/L & 0 & C_o(x_4-x_1)[(x_4-x_1)^2 - L^2]/(6L) \\ 0 & 0 & 0 & 0 & 0 & 1/L \\ 0 & 0 & 0 & 0 & 1 & -1/L \\ 0 & 0 & 0 & 1/L & 0 & -C_o L/6 \end{bmatrix}$$

It is reasonable to obtain $h(x)$ in closed form. In the numerator of the expression for $h(x)$, only the second row of $W_o^{-1}W_d(x)$ is evaluated because only the second component of the braced vector is used:

$$W_o^{-1}W_d(x) = \begin{bmatrix} \cdots & \cdots & \cdots & \cdots & \cdots & \cdots \\ 0 & 0 & 0 & -d_{13}(x) + d_{15}(x)(x_3-x_1)/L & 0 & 0 \\ \cdots & \cdots & \cdots & \cdots & \cdots & \cdots \\ \cdots & \cdots & \cdots & \cdots & \cdots & \cdots \\ \cdots & \cdots & \cdots & \cdots & \cdots & \cdots \\ \cdots & \cdots & \cdots & \cdots & \cdots & \cdots \end{bmatrix}$$

Similarly, the components of the products $W_o^{-1}B_o$ and $W_o^{-1}B_d(x)$ used in computing $h(x)$ are:

$$W_o^{-1}B_o =$$

$$\begin{bmatrix} \cdots \\ C_o(x_3 - x_2)^3/12 + C_o(x_3 - x_1)((x_2 + x_4 - 2x_5)[(x_3-x_1)^2 - L^2] - \\ (x_5 - x_2)^3 - (x_5 - x_4)^3)/(12L) \\ \cdots \\ ((x_2 + x_4)/2 - x_5)/L \\ \cdots \\ \cdots \end{bmatrix}$$

$$W_o^{-1}B_d(x) = \begin{bmatrix} \cdots \\ d_{23}(x)/2 - (x_3 - x_1)(d_{25}(x) + d_{45}(x))/(2L) \\ \cdots \\ \cdots \\ \cdots \\ \cdots \end{bmatrix}$$

Then:

$$h(x) = C_o \frac{\{-W_o^{-1}W_d(x)W_o^{-1}B_o + W_o^{-1}B_d(x)\}_2}{\{W_o^{-1}B_o\}_2}$$

$$= 6 \frac{(d_{13}(x) - d_{15}(x)(x_3 - x_1)/L)(x_2 + x_4 - 2x_5)/L + d_{23}(x) - (x_3 - x_1)(d_{25}(x) + d_{45}(x))/L}{(x_3 - x_2)^3 + (x_3 - x_1)((x_2 + x_4 - 2x_5)[(x_3 - x_1)^2 - L^2] - (x_5 - x_2)^3 - (x_5 - x_4)^3)/L}$$

$$= \frac{6}{L^3} \frac{\left(d_{13}(x) - d_{15}(x)\left(\frac{x_3-x_1}{L}\right)\right)\left(\frac{x_2+x_4-2x_5}{L}\right) + d_{23}(x) - \left(\frac{x_3-x_1}{L}\right)(d_{25}(x) + d_{45}(x))}{\left(\frac{x_3-x_2}{L}\right)^3 + \left(\frac{x_3-x_1}{L}\right)\left(\left(\frac{x_2+x_4-2x_5}{L}\right)\left[\left(\frac{x_3-x_1}{L}\right)^2 - 1\right] - \left(\frac{x_5-x_2}{L}\right)^3 - \left(\frac{x_5-x_4}{L}\right)^3\right)}$$

$$= \frac{6}{L^3 D}\left(d_{13}(x) - d_{15}(x)\left(\frac{x_3-x_1}{L}\right)\right)\left(\frac{x_2+x_4-2x_5}{L}\right) + d_{23}(x) - \left(\frac{x_3-x_1}{L}\right)(d_{25}(x) + d_{45}(x))$$

where the denominator factor $D$ is given by:

$$D = \left(\frac{x_3 - x_2}{L}\right)^3 + \left(\frac{x_3 - x_1}{L}\right)\left(\left(\frac{x_2 + x_4 - 2x_5}{L}\right)\left[\left(\frac{x_3 - x_1}{L}\right)^2 - 1\right] - \left(\frac{x_5 - x_2}{L}\right)^3 - \left(\frac{x_5 - x_4}{L}\right)^3\right)$$

This result has been kept somewhat general so that in closed form, the span function $h(x)$ can be investigated for support locations other than third point support locations. Now, it is particularized to third point supports, where:

$x_1 = -L/2$, $x_2 = -L/6$, $x_3 = 0$, $x_4 = L/6$, $x_5 = L/2$

Then, $D = 23/108$ and:

$$h(x) = \frac{324}{23L^3}\begin{cases} -2d_{13}(x) + d_{15}(x), & x_1 < x \leq x_2 \\ -2d_{13}(x) + d_{15}(x) + 2d_{23}(x) - d_{25}(x), & x_2 < x \leq x_3 \\ d_{15}(x) - d_{25}(x), & x_3 < x \leq x_4 \\ d_{15}(x) - d_{25}(x) - d_{45}(x), & x_4 < x \leq x_5 \end{cases}$$

$$= \frac{324}{23L^3} \begin{cases} (L/2-|x|)L/3, & 0 \le |x| \le L/6 \\ (L/2-|x|)^2, & L/6 < |x| \le L/2 \\ 0, & \text{otherwise} \end{cases}$$

Figure 15:
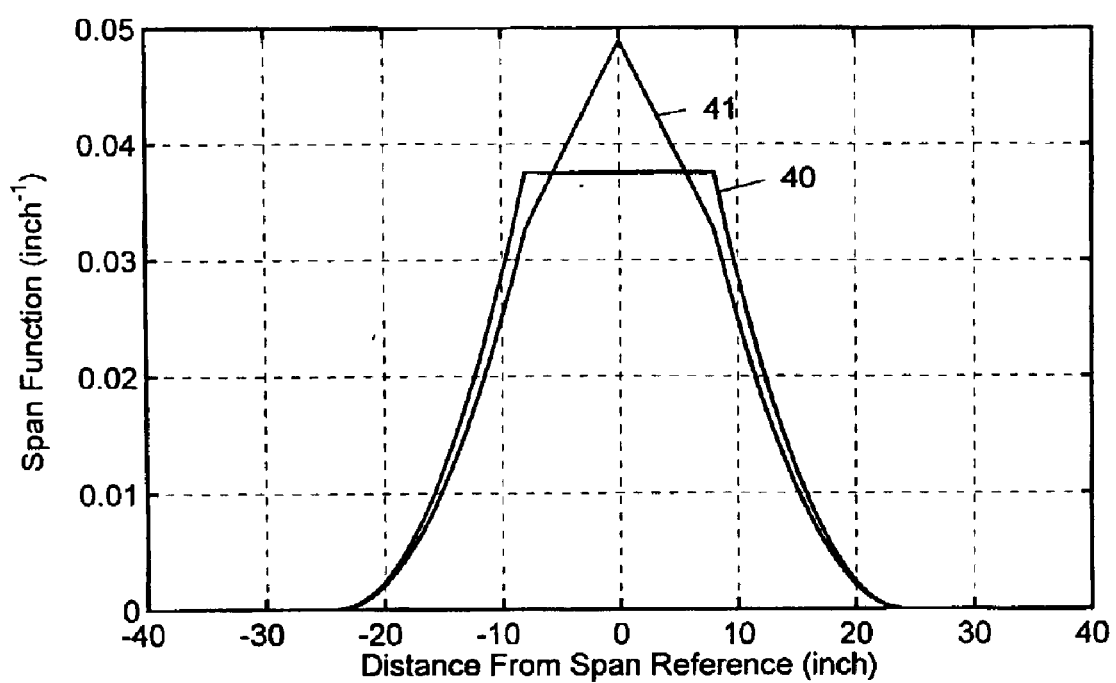
FIG. 15 illustrates span functions for the two versions of machinery represented in FIG. 14.

This span function is plotted in FIG. 15 as curve 41. Its integral is one as it should be.

A Linear Algebraic Solution for Local Compliance Estimates

Span functions may be used to provide local compliance estimates from solution of a linear system of equations. For example, the output matrix weights computed for the HLCT can be used to write a system of linear equations as:

$$HC = C_m$$

C is an (N,1)-dimensional vector of unknown local compliances. $C_m$ is a (κ,1)-dimensional vector of measured compliances. H is a (κ,N)-dimensional matrix describing how the local compliance values C are weighted into the measurements $C_m$, where $N=K^+κ+p-1$. Matrix H can be written in terms of the output matrices previously computed for a perfectly aligned HCLT having rigid supports as:

$$H = \begin{bmatrix} [H1], 0, 0, 0, 0, 0, 0, 0, 0, \ldots, 0 \\ 0, [H1], 0, 0, 0, 0, 0, 0, 0, \ldots, 0 \\ 0, 0, [H1], 0, 0, 0, 0, 0, 0, \ldots, 0 \\ 0, 0, 0, [H1], 0, 0, 0, 0, 0, \ldots, 0 \\ 0, 0, 0, 0, [H2], 0, 0, 0, 0, \ldots, 0 \\ 0, 0, 0, 0, 0, [H2], 0, 0, 0, \ldots, 0 \\ 0, 0, 0, 0, 0, 0, [H2], 0, 0, \ldots, 0 \\ 0, 0, 0, 0, 0, 0, 0, [H3], 0, \ldots, 0 \\ \vdots & \vdots & \vdots & \ddots & \vdots & \vdots & \vdots \\ 0, \ldots, 0, [H3], 0, 0, 0, 0, 0, 0 \\ 0, \ldots, 0, 0, [H4], 0, 0, 0, 0, 0 \\ 0, \ldots, 0, 0, 0, [H4], 0, 0, 0, 0 \\ 0, \ldots, 0, 0, 0, 0, [H4], 0, 0, 0 \\ 0, \ldots, 0, 0, 0, 0, 0, [H5], 0, 0 \\ 0, \ldots, 0, 0, 0, 0, 0, 0, [H5], 0 \\ 0, \ldots, 0, 0, 0, 0, 0, 0, 0, [H5] \end{bmatrix}$$

Figure 20:
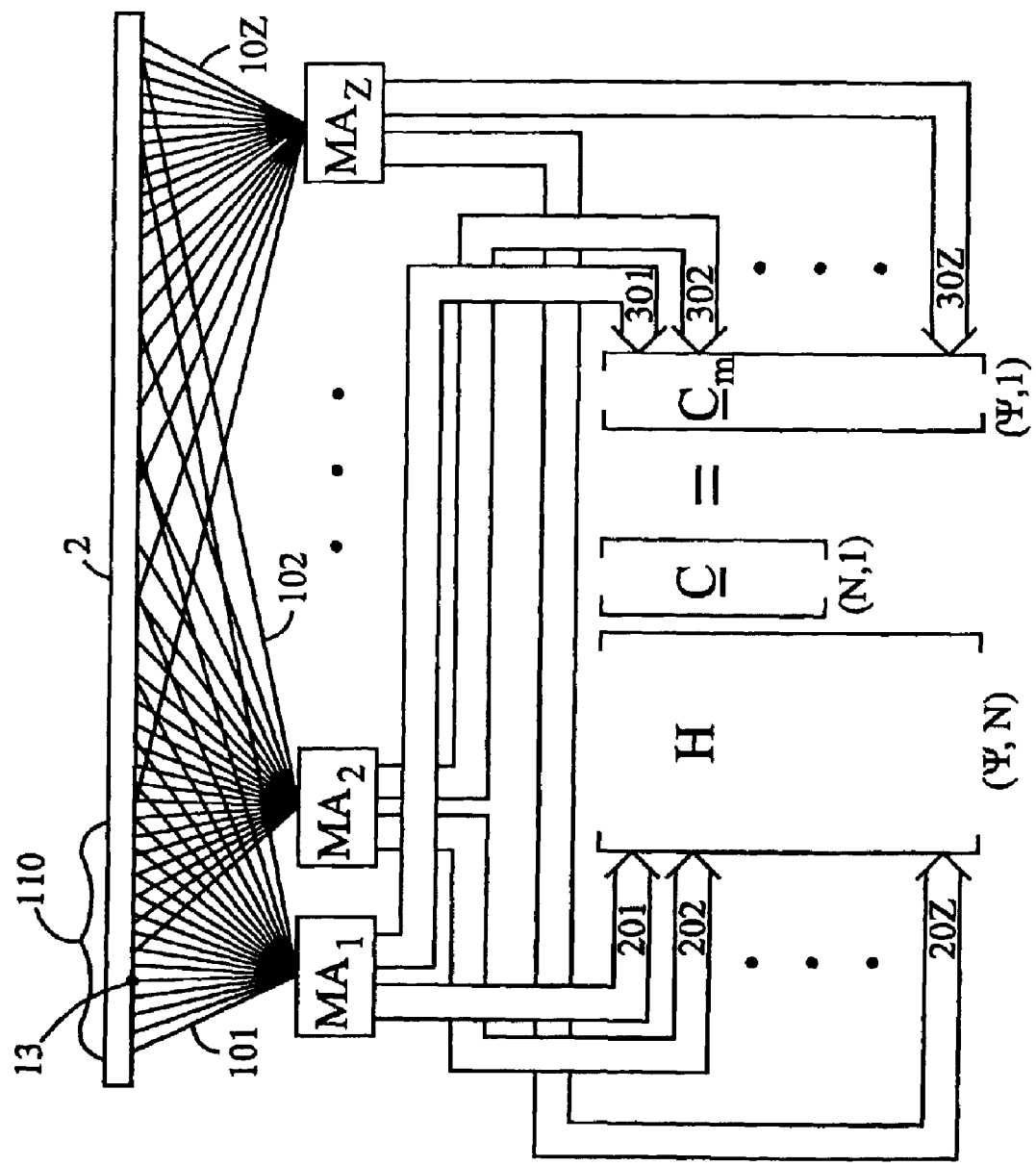
FIG. 20 illustrates schematically the setup of algebraic equations for local compliance estimation using span functions.

This formulation is a subset of an approach represented by FIG. 20. The reduced problem is discussed here first and solutions with simulated and real data are presented.

Methods for solving linear equations exist in the prior art and were discussed earlier in this specification. The rank r of matrix H is important. In the HCLT example, the numbers of components in the output matrices H1, . . . , H5 have been reduced from p=37 to p=23, taking advantage of the zeros in the output matrices for the case of perfect alignment and rigid supports. For the HCLT with reduced p, rank r=κ, and solutions of C occur in a linear manifold having dimension N−κ. Among these solutions, the minimum norm solution, i.e. the one minimizing $C^TC$ is:

$$C = V_\kappa S_\kappa^{-1} U^T C_m$$

$V_\kappa$, $S_\kappa$, and U come from a singular value decomposition of H, given by:

$$H = USV^T$$
$$= US_\kappa V_\kappa^T$$

$S_\kappa$ is a (κ,κ)-dimensional square matrix having all zeros except for its main diagonal, which contains the nonzero singular values of H (square roots of eigenvalues of $H^TH$). V is an (N,N)-dimensional square matrix whose columns are N orthonormal eigenvectors of $H^TH$, and U is a (κ,κ)-dimensional square matrix whose columns are orthonormal eigenvectors of $HH^T$. V may be partitioned as $V=[V_\kappa|V_n]$, with the first κ columns comprising $V_\kappa$ spanning the row space of H, and the remaining N−κ columns comprising $V_n$ spanning the null space of H.

Figure 16:
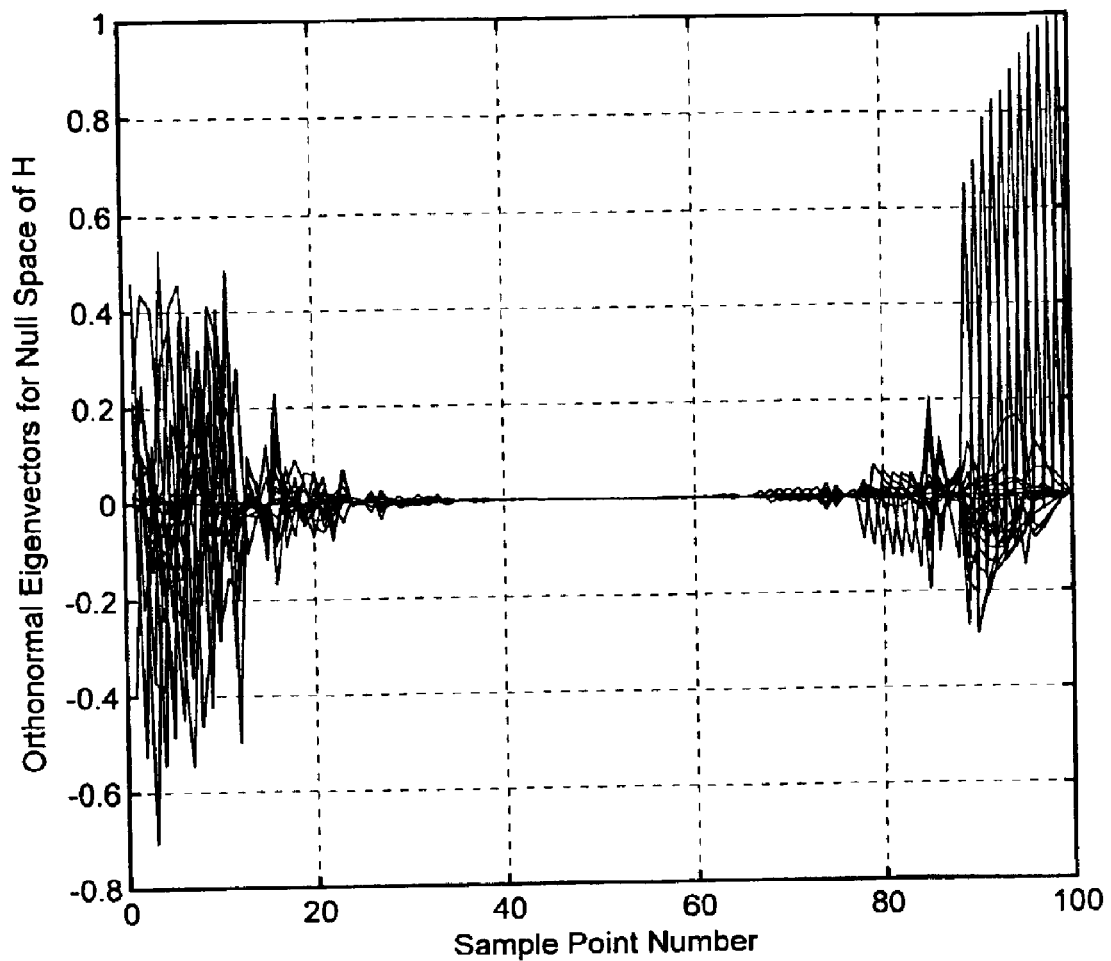
FIG. 16 is a plot of eigenvectors spanning the null space of the linear transformation of local compliance to measured compliance for a perfectly aligned HCLT with rigid supports.

The minimum norm solution for the vector C has components near beam-ends that are small, approaching zero. This is consistent with minimum norm, but unreasonable for local compliance in a wood board. The solution $C=V_\kappa S_\kappa^{-1} U^T C_m$, being a linear combination of the columns of $V_\kappa$, is in the row space of H. Any solution in the null space of H, i.e. any linear combination of the columns of $V_n$, may be added to the solution C without changing HC because $HV_n=0$. Consequently, one can write:

$$C = V_\kappa S_\kappa^{-1} U^T C_m + V_n \gamma$$

where γ is any (N−κ,1)-dimensional vector. To gain an idea of the kind of vectors being added to C by the addition of vectors in the null space of H, the N−κ=P−1 orthonormal eigenvectors comprising the columns of $V_n$ are all plotted in FIG. 16. For a simulated beam, the number of local compliance sample points along the beam is taken as N=100, and the number κ of measurement points is therefore κ=N−p+1=78. It can be seen from FIG. 16, that contributions from vectors in the null space have little effect except for components at both ends of the domain, which correspond to ends of the beam. The conclusion is that only little control of the result is practical for components of C except near bean-ends, by adding a vector of the form $V_n \gamma$. Consequently, a reasonable choice is to specify the first (p−1)/2 components of C to be equal to the (p+1)/2 component value, and to specify the last (p−1)/2 components of C to be equal to the N−(p−1)/2 component value. Specifying components near the ends of the beam is practical with vectors from the null space of H as is clear from FIG. 16. This may be accomplished by augmenting the H matrix and the measured compliance vector $C_m$ thereby defining a unique solution $C_a$ of the linear system:

$$H_a C_a = C_{ma}$$

The augmented (N, 1) dimensional vector $C_{ma}$ is obtained by appending (p−1)/2 component zeros at the beginning and end of the (κ,1)-dimensional vector $C_m$ according to:

$$C_{ma} = \begin{bmatrix} \text{zeros}((p-1)/2, 1) \\ C_m \\ \text{zeros}((p-1)/2, 1) \end{bmatrix}$$

The (N,N)-dimensional augmented matrix $H_a$ has rank N, and is obtained by appending (p−1)2 rows at the top and bottom of the (κ,N)-dimensional matrix H according to:

$$H_a = \begin{bmatrix} I_{(p-1)/2}, -\text{ones}((p-1)/2, 1), \text{zeros}((p-1)/2, N-(p+1)/2) \\ H \\ \text{zeros}((p-1)/2, N-(p+1)/2), -\text{ones}((p-1)/2, 1), I_{(p-1)/2} \end{bmatrix}$$

The symbol $I_{(p-1)/2}$ refers to the (p−1)/2-dimensional identity matrix. Zeros(i,j) refers to a matrix having dimensions (i,j), every entry being a zero, and similarly every entry in ones(i,j) is a one. The first (p−1)/2 rows begin with a (p−1)/2-dimensional identity matrix, then a column of (p−1)/2 entries all having value −1, and the remainders of the first (p−1)/2 rows all being zeros. The (p−1)/2 rows appended at the bottom have first the zeros, then the −1's and then the identity matrix in reverse order from the top appended rows. This arrangement specifies the first (p−1)/2 components of $C_a$ to equal its (p+1)/2 component, and the last (p−1)/2 components to equal its N−(p−1)/2 component; thereby completing a unique specification for $C_a$ from $C_a = H_a^{-1} C_{ma}$. In the event H and hence $H_a$ does not have full rank, the equation $H_a C_a = C_{ma}$ can be premultiplied by $H_a^T$ and a solution found from the resulting normal equations as previously described in this specification.

These results are derived assuming that the N unknown local compliance values are for a subdivision of the beam extending from one end of the beam to the other. This is one application; however, the N unknown local compliance values could represent a subdivision for just part of the beam length. The same linear algebra applies except for the coefficient entries in the H matrix.

Results of the Linear Algebraic Solution Applied to Simulated Data

Figure 17:
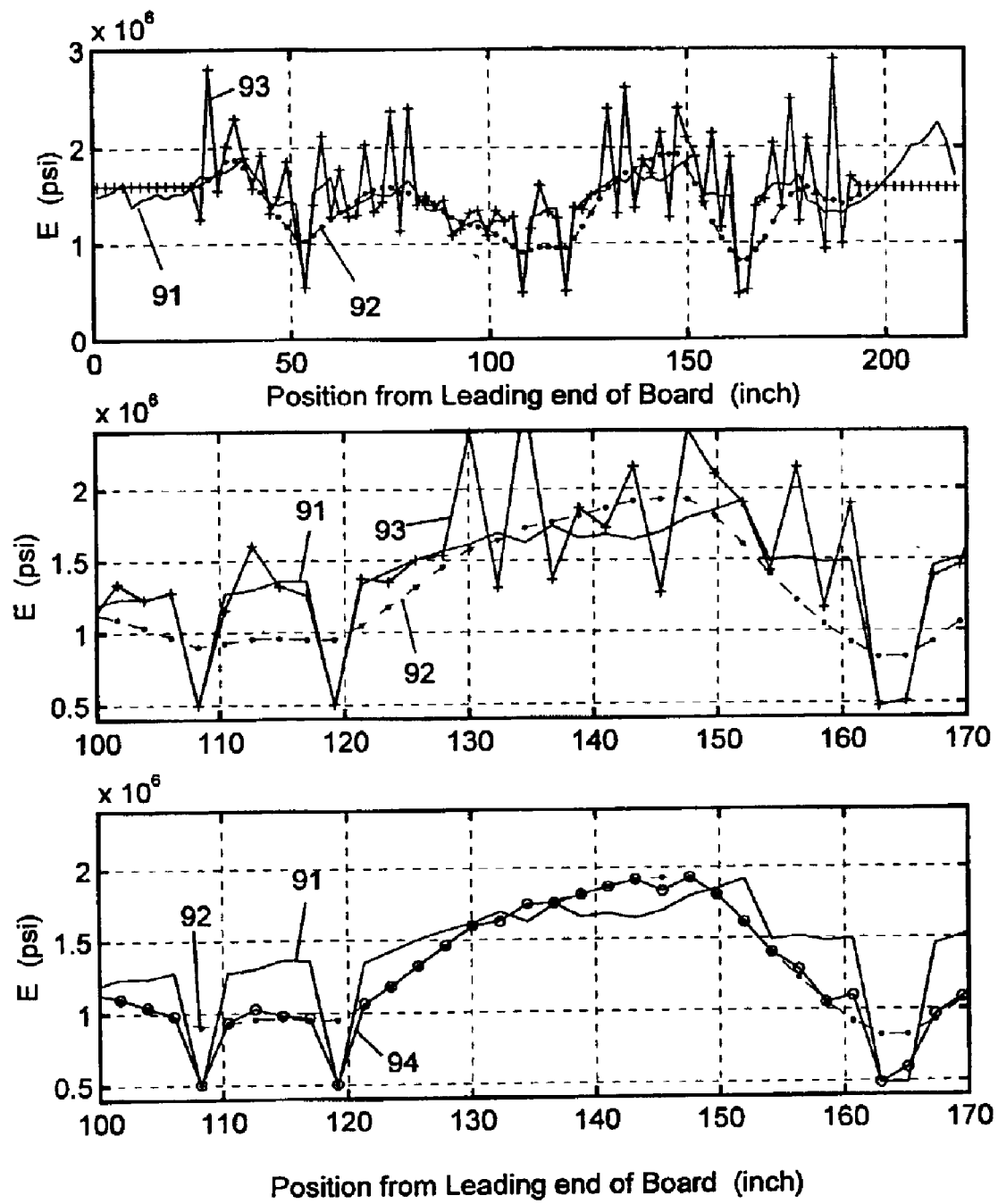
FIG. 17 graphs results of a linear algebraic method for estimating local compliance from compliance measurements of a simulated wood board having compliance pulses; reciprocal functions are plotted.

For the HCLT operating on a simulated wood board, assuming N=100, κ=78, and p=23, FIG. 17 shows the result of applying this method to a board having pseudo-randomly generated local compliance values with statistics similar to those used for FIG. 10. For the data of FIG. 17, the expected value of the compliance has been changed to 1/(1.5e6 psi), and the coefficient of variation for the component local compliances has been changed to 0.3. Compliance pulses with magnitude equal to twice the mean compliance are added to local compliance values at the same places as for FIG. 10, and pseudo-random, zero-mean, white, gaussian, measurement noise having variance var(v)=0.00001(10$^6$ psi)$^{-2}$ is added to the compliance measurements. The middle and lower plots of FIG. 17 show only the results for domain between 100 and 170 inch, the expansion allowing better observation of plot detail than the upper plot. Curve 91 illustrates the reciprocal E=1./C of the generated local compliances, where the dot slash "./" indicates taking the component-by-component reciprocal in the vector C. The sampling distance is 2.1866 inch. The dashed curve labeled 92 and marked with dots is 1./$C_m$ the reciprocal of the measured compliance vector $C_m$. The measured compliance is obtained by processing the generated local compliance values equivalently to a perfectly aligned HCLT with rigid supports being applied to a board having the local compliance values in C. That is, $C_m$=HC. The curve labeled 93, illustrated in the upper and middle plots of FIG. 17 and marked with plus signs, shows estimates $E_a$ of local E. It is the reciprocal of the computed local compliance values in vector $C_a$ obtained from the above inversion of $H_a$, with correction factor applied. The correction factor $(1+COV_c^2)$ is as described previously, where covariance is defined using the linear relationship $C_a = H_a^{-1} C_{ma}$ and the variance var(v) of measured compliance. Thus:

$$E_a = (1./H_a^{-1} C_{ma}) .* (1+COV_c^2)$$

where the dot star ".*" indicates component-by-component multiplication.

Referring to the upper and middle plots of FIG. 17, the dips in the generated E curve 91 due to compliance pulses are closely followed by the computed curve 93 for estimated local $E_a$. However, oscillations in $E_a$ of curve 93 do not agree with the generated E of curve 91. In application, the ability of the estimated curve 93 to closely approximate the low E signal can be an important aid in structural property determination. Then, the effect of weakening characteristics such as knots may be evaluated more accurately. The oscillatory excursions into high E territory may not be a disadvantage so long as a moving average of neighboring components represents the general properties of the board. An ad hoc transformation can be defined that for the most part retains the capability of the result in following the low E signal but de-emphasizes the remaining oscillations. The transformation is applied to the difference $C_a - C_{ma}$ between components of $C_a$ and $C_{ma}$. For example, a scale factor consisting of the magnitude of this difference for each component can be normalized by the maximum component difference, the scale factor taken to a power, multiplied by the difference, and then added to the measured values $C_{mn}$. Explicitly, a result $A_t$ is obtained from:

$$C_{at} = \left( \left[ (C_a - C_{ma}) / \max_{(p+1)/2 \leq i \leq N-(p-1)/2} (C_a(i) - C_{ma}(i)) \cdot {}^\wedge j \right] .* (C_a - C_{ma}) + C_{ma} \right).$$

The dot hat ".^j" notation indicates taking the $j^{th}$ power component by component of the vector in brackets, and the .* notation indicates component-by-component multiplication. This notation follows the convention used by programs of the Mathworks, Inc. in Natick, Mass.

The lower part of FIG. 17 shows curve 94, which is an expanded plot of 1./$C_{at}$ for j=2. Also, shown is 1./C as curve 91, and 1./$C_m$ as curve 92. For major dips in local E, the ad hoc curve 94 follows the dips almost as well as the estimated local E (curve 93 in the middle plot of FIG. 17). At other places, curve 94 follows measured $E_m$, curve 92.

Results of the Linear Algebraic Solution Applied to Real Data

Figure 18:
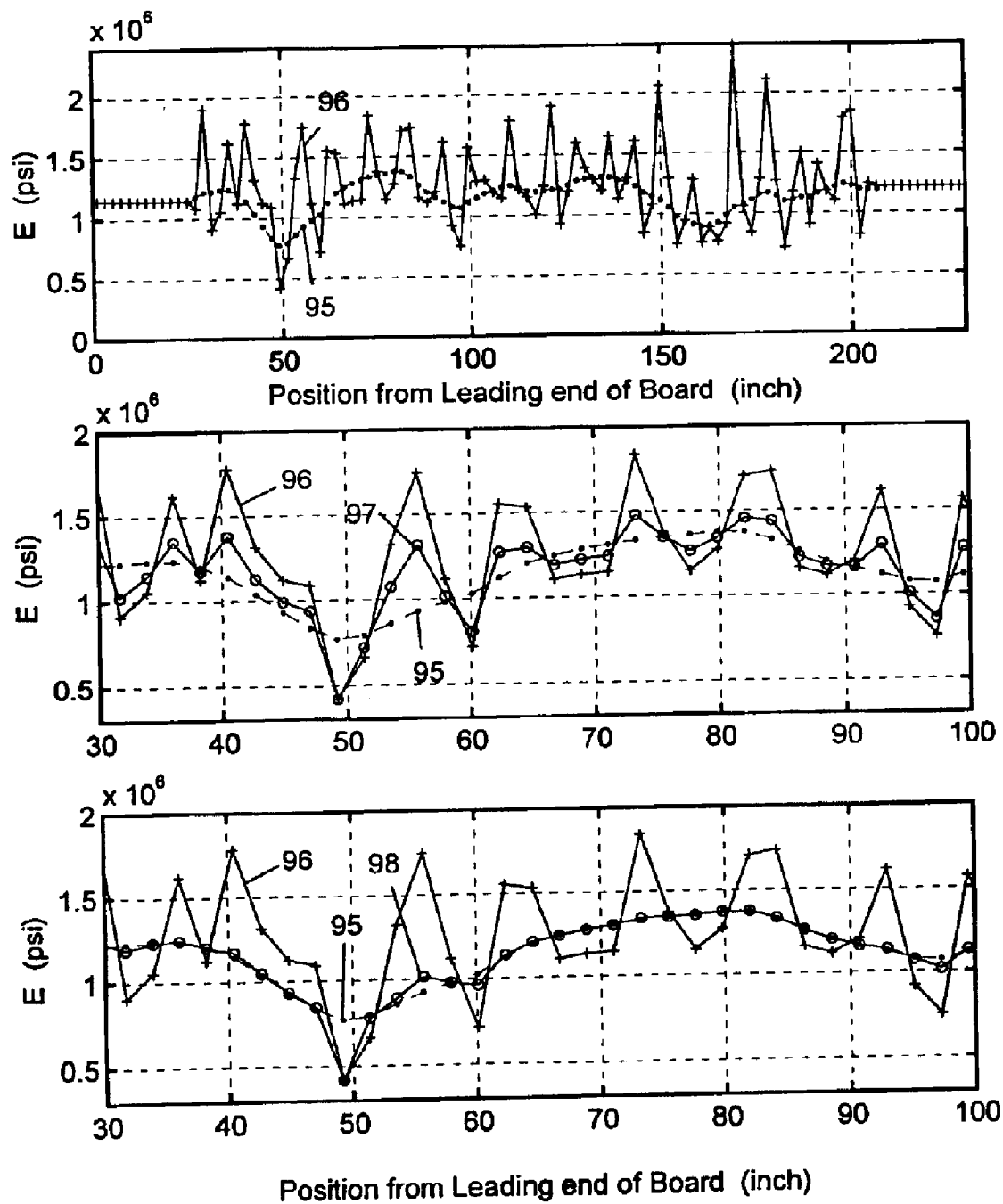
FIG. 18 graphs results of a linear algebraic method for estimating local compliance from the same compliance measurements used for the Kalman results of FIG. 11; reciprocal functions are plotted.

The same measured compliance data as used for FIG. 11 were used with the linear algebraic method to estimate local compliance. In FIG. 18, the curve labeled 95 and marked with dots is $E_m$=1./$C_m$, the reciprocal of the measured compliance vector $C_m$. The curve labeled 96 is estimated local E computed as $E_a$ the reciprocal of estimated local compliance corrected with $(1+COV_c^2)$. In the middle and lower plots of FIG. 18, the ad hoc curves 1./$C_{at}$ are labeled 97 in the middle plot, where the scale factor power is j=0.5, and 98 in the lower plot, where j=2. Similarly with the simulated data, these curves illustrate how the ad hoc curves of 1./$C_{at}$ track low E but tend to follow measured $E_m$ elsewhere.

Extending the Linear Algebraic Method

The foregoing introduces a linear algebraic method for obtaining local compliance from compliance measurements by solutions of the system HC=$C_m$ where H is a (κ,N)-dimensional matrix obtained from HCLT span functions, and where κ<N. The rows of H contain weighting coefficients determined from span functions, each row of H corresponding to a particular bending span and when applied to the unknown local compliance values gives the compliance measurement for that bending span. The nonzero coefficients in a row are the same as the coefficients from the corresponding output matrix defined in the preceding state-space representation of bending span compliance measurements.

In FIG. 20, a schematic illustration is given of a linear algebraic approach applied to a more general system. The applicable matrix equation HC=$C_m$ is illustrated diagrammatically, and dimensions in parentheses are included beneath each part of the equation. Beam 2 is shown as being measured by Z different machines $MA_1$, $MA_2$, ..., $MA_Z$. Each machine measures the beam at multiple measurement points indicated schematically by the fan of lines 101 in FIG. 20 for machine $MA_1$. Measurement point 13 is shown as being one of those for machine $MA_1$. At measurement point 13, measured compliance from a corresponding bending span is determined as a weighted linear combination of local compliances along the beam. The weights come from a span function corresponding to the bending span. The domain, over which the span function corresponding to measurement point 13 is nonzero, is the domain labeled 110 on beam 2, and so the corresponding nonzero weights of the linear combination apply to local compliance values in domain 110. These weights are entered into a row of matrix H via wide line 201, and, the measured compliance value is entered, via wide line 301, into the position of vector $C_m$ that corresponds to the row of H. The weights must be entered into the proper horizontal positions of the row of H so that they multiply the proper components of C in domain 110 according to the defined linear combination.

Similarly a row of H and a position of $C_m$ is defined by every measurement point with its corresponding bending span, span function and weight coefficients from machine $MA_1$. The previous description about the HCLT would fit into the present framework, if machine MA, were replaced with the HCLT. In that case, the wide lines 201, and 301 would be κ positions wide. Similarly, each of the other Z machines provides span function determined weight entries to rows of H via wide lines 202, . . . , 20Z and provides compliance measurements to $C_m$ via wide lines 302, . . . , 30Z. It is necessary to have the vertical position of the row entries in H and the vertical position of the compliance measurement in $C_m$ correspond. It is also necessary that the horizontal positions of the weight entries in the rows of H correspond to the proper column positions of components of C.

The result is a matrix (Ψ,N)-dimensional matrix H and a (Ψ,1)-dimensional vector of compliance measurements $C_m$. C as before is the (N,1)-dimensional vector representing N unknown local compliance values along beam 2.

Any number Ψ of rows in H, which is also the length of vector $C_m$, may be defined. Each row corresponds to an equation relating a measured compliance to a linear combination of unknown local compliance values. Each equation is the result of a bending span applied to the beam at a measurement point. For best determination of C, it is desirable for a beam to be tested with many bending spans at many measurement points. A good design will cause every individual local compliance values to be well represented as significant constituents of the linear combination in many equations. A significant constituent is one having a coefficient in the linear combination that is not negligibly small when compared to the others. If local compliance values near beam ends can be weighted by significant coefficients in H, i.e., if first and last few columns of H have sufficiently nonzero entries, it will be possible to estimate compliance values near the beam ends.

The goal is for the rows of H to adequately span N-dimensional space. If Ψ>N, the system is overdetermined. In any event, the normal equations are used as previously described to find least squares solutions to $HC=C_m$. If the rank of H is r, and r<N, there will be a linear manifold of dimension N−r of least squares solutions, even if Ψ>N. However, by increasing A, it is likely that the dimension of N−r can be reduced.

The remaining N−r degrees of freedom may be used as with the linear algebraic solution for the HCLT by augmenting the H matrix and the $C_m$ vector, thereby defining least squares solution having constant local compliance segments at beam ends.

In compliance with the statute, the invention has been described in language more or less specific as to method features. The invention is not limited to the specific configurations shown, because the method disclosed teaches a general approach to putting the invention into effect. Therefore, the invention is claimed in any of its forms or modifications within the proper scope of the appended claims appropriately interpreted in accordance with the doctrine of equivalents:

What is claimed is:

1. A computer-implemented method of computing span function for a bending span used to measure compliance of an elongated beam at a measurement point on the beam and using the span function in the estimation of local compliance values at points along the beam, the method comprising the following steps:

defining a compliance test function comprising a background compliance plus a compliance impulse of weight b at position x relative to the measurement point;

obtaining an expression of measured compliance as a function $C_m(b,x)$ of impulse weight b and position x;

computing the span function h(x) as being substantially equal to the partial derivative, of $C_m(b,x)$ with respect to the impulse weight b, evaluated at b=0; and using a computer to implement an algorithm dependent on the span function h(x) in the estimation of local compliance values.

2. The method of claim 1 for computing and using span function applied to a plurality of Ψ numbered bending spans giving a corresponding plurality of Ψ numbered compliance measurements at a corresponding plurality of Ψ numbered measurement points, not necessarily all distinct, along the beam, yielding a corresponding plurality of Ψ numbered span functions, and using the span functions and compliance measurements to obtain a least squares solution for an (N,1)-dimensional vector C with components representing N local compliance values at points spaced along the beam, by the following steps:

forming a (Ψ,1)-dimensional vector $C_m$ with numbered components comprised of the corresponding plurality of Ψ numbered compliance measurements;

forming a (Ψ,N)-dimensional rectangular matrix H having Ψ numbered rows, each row being a (1,N)-dimensional matrix in correspondence with a compliance measurement and a span function and comprised of entries computed from the span function, the entries positioned in the row so that the matrix product of the row and vector C is a scalar linear combination of components of vector C corresponding to a compliance measurement in $C_m$; and computing C as a least squares solution to $HC=C_m$, the solution being contained in a linear manifold having dimension N−r, r being the rank of matrix H.

3. The method of claim 2 wherein the matrix H is augmented to matrix $H_a$ and the measured compliance vector is augmented to vector $C_{ma}$, giving a least squares solution $C_a$ of the equation $C_m=H_aC_a$, the solution $C_a$ being in the linear manifold, a plurality of first components of $C_a$ being a uniform value and a plurality of last components of $C_a$ being a uniform value; whereby $C_a$ makes physical sense as well as being in the linear manifold.

4. A computer-implemented method of obtaining a local compliance estimate at a point of estimation on an elongated beam, from a sequence of "m" measured compliance values at "m" measurement points spaced along the beam, each measured compliance value being obtained by applying a bending span to a length segment of the beam, the length segment including the point of estimation and having unknown local compliance values along its length, the length segment and measured compliance value being identified with a corresponding measurement point on the beam; thereby defining a sequence of corresponding "m" measured compliance values, "m" measurement points, "m" bending spans and "m" length segments; the method comprising the following steps:

representing each measured compliance value minus an estimated mean value common to the measured compliance sequence as being the output from a state-space representation of a dynamic system, the state-space representation comprising a vector state equation and a scalar output equation, the state equation containing a state matrix, a state vector, and an input vector with at least one component being a white random noise source, the state equation describing how the state vector with component state variables changes from one measurement point to the next, the local compliance values from the corresponding length segment minus the common estimated mean value being represented by the state variables, the output equation having an output matrix specific to a corresponding bending span and having a measurement white random noise source independent of input vector noise, the output equation specifying for each measurement point the dynamic system output as a linear combination of the state variables plus measurement noise;

using a priori information to initialize a Kalman filter by initializing estimates of the state vector, input vector covariance matrix, measurement noise variance, and state vector covariance matrix;

applying the Kalman filter recursively to the sequence of "m" measured compliance values minus the common estimated mean value;

computing from the Kalman filter a sequence of "m" state vector estimates, one corresponding to each member of the measured compliance value sequence; and obtaining the local compliance estimate at the point of estimation as the common estimated mean value plus a selected component from a selected state vector estimate in the sequence of "m" state vector estimates.

5. The method of claim 4 wherein the coefficients of each output matrix are computed from a span function for the corresponding bending span, the span function computed according to the following steps:

defining a compliance test function comprising a background compliance plus a compliance impulse of weight b at position x relative to the corresponding measurement point;

deriving an expression of measured compliance as a function $C_m(b,x)$ of impulse weight b and position x; and computing the span function h(x) as being substantially equal to the partial derivative, of $C_m(b,x)$ with respect to the impulse weight b, evaluated at b=0.

6. The method of claim 5 wherein the selected state vector estimate is the last one in the sequence of state vector estimates.

7. The method of claim 5 wherein the selected state vector estimate is the last one in the sequence of state vector estimates for which the selected component has, in the corresponding output matrix, a coefficient magnitude exceeding a selected threshold value.

8. The method of claim 5 applied to obtain a sequence of "n" local compliance estimates at corresponding "n" points of estimation spaced along the length of the beam, the sequence of "n" points of estimation beginning substantially at one end of the beam and ending substantially at the other end of the beam, the sequence of "n" local compliance estimates obtained from a sequence of "M" compliance measurements at a corresponding sequence of "M" measurement points on the beam and a corresponding computed sequence of "M" state vector estimates, the sequence of "M" measurement points being a coalesced grand sequence of measurement points from the "n" sequences of measurement points for the "n" points of estimation, the common estimated mean value being common to all members of the coalesced grand sequence.

9. The method of claim 8 wherein, for each point of estimation, the selected state vector estimate is the last one in the sequence of "M" state vector estimates that has a component representing, at the point of estimation, the local compliance minus the common estimated mean value.

10. The method of claim 8 wherein, for each point of estimation, the selected state vector estimate is the last one in the sequence of "M" state vector estimates that has a component representing, at the point of estimation, the local compliance minus the common estimated mean value and also has, in the corresponding output matrix, a coefficient magnitude exceeding a selected threshold value.

11. The method of claim 8 wherein the "M" compliance measurements minus the common estimated mean value and minus the random measurement noise are modeled as coming from an autoregressive moving average (ARMA) random process, the autoregressive coefficients and input noise comprising the autoregressive part of the ARMA model and yielding, for the state-space dynamic system model, state variables as an autoregressive random process that models the sequence of local compliance values minus the common estimated mean value, the autoregressive coefficients appearing in the state matrix, the moving average coefficients of the ARMA model for each compliance measurement being weighting coefficients in the output matrix of the state-space model, the moving average coefficients changing in correspondence with bending span changes, and wherein the initial state vector covariance, state matrix, and input vector covariance satisfy substantially a discrete Lyapunov equation.

12. The method of claim 11 wherein additionally, autoregressive coefficients of the ARMA model are obtained as a priori information from compliance measurements, estimation of autocorrelations of measured compliance, and solution of a system of equations relating autocorrelations and autoregressive coefficients.

13. The method of claim 11 wherein the autoregressive part of the model is simplified to include at most two autoregressive coefficients.

14. The method of claim 13 wherein one autoregressive coefficient is used with a first input random white noise source and a second autoregressive coefficient is used with a second input random white noise source independent of the first in a parallel branch, the two branches being used in the autoregressive part of the ARMA model.

15. The method of claim 8 wherein, additionally, observed systematic measurement noise is modeled, included in the output of the state-space representation of the dynamic system, and estimated from a component of the state vector corresponding to each measured compliance value; whereby the estimated systematic noise may be used as an indicator of performance of the measuring apparatus.

16. The method of claim 8 wherein additionally a measure of estimation quality is computed for each local compliance estimate.

17. The method of claim 16 wherein additionally estimated local E is computed as a corrected reciprocal of estimated local compliance, and a measure of estimation quality is computed for each estimate of local E as a corrected measure of estimation quality for local compliance.

18. The method of claim 8 wherein a plurality of measurement sequences are arranged as a vector measurement sequence, each component of the vector measurement sequence corresponding to a different sequence of bending spans but corresponding to substantially the same measurement points as the other components of the vector measurement sequence, the state-space dynamic system model being the same as in claim 8 except for additional rows in the output matrix for the output equation, the output being a vector output, the Kalman filter operating recursively on the vector measurement sequence minus an estimated mean vector common to each member of the vector measurement sequence, the Kalman filter providing for each measurement point an optimal estimate of the state vector, the local compliance estimates being determined through their correspondence with selected components of selected estimated state vectors.

19. A computer-implemented calibration method in a machine for measuring modulus of elasticity of an elongated beam, the machine applying a sequence of bending spans to a corresponding sequence of length segments at a corresponding sequence of measurement points along the beam, each bending span having defined support specifications, wherein the computer is programmed to apply a sequence of calibration factors in correspondence with the bending spans, each factor specific to its corresponding bending span and determined as the factor, which, when applied during the measurement of a beam having a uniform modulus of elasticity, causes the measured modulus of elasticity to be that uniform value for each bending span in the sequence; whereby machines, having a plurality of bending spans and designed to use just one calibration factor, can be made to give accurate readings for each bending span even if support conditions deviate away from the defined support specifications.

20. The calibration method of claim 19 wherein the computation of each calibration factor specific to its corresponding bending span is substantially equivalent to adjusting the factor so that the coefficients in an output matrix sum to one, the output matrix being the output matrix of a state-space representation of a dynamic system modeling the reciprocal of the modulus of elasticity measurement minus a common estimated mean reciprocal modulus of elasticity value as the output of the dynamic system.

* * * * *

UNITED STATES PATENT AND TRADEMARK OFFICE
CERTIFICATE OF CORRECTION

PATENT NO. : 7,047,156 B1  
APPLICATION NO. : 10/318711  
DATED : May 16, 2006  
INVENTOR(S) : Bechtel et al.

Page 1 of 11

It is certified that error appears in the above-identified patent and that said Letters Patent is hereby corrected as shown below:

1. The following errata are for correction of U.S. Patent 7,047,156, as issued May 16, 2006.
2. Title PAGE item 56

4. $2^{nd}$ column, line 1. Should be: Bechtel, F.K. ...
5. $2^{nd}$ column, line 6. Should be: Bechtel & Allen, ...
6. 
7. FIGURES
8. All figures: Published copy is very poor. Originals figures submitted with the application were crisp.
9. 
10. SPECIFICATION

| | Col | Line | Corrected Text | Problem |
|---|---|---|---|---|
| 11 | | | | |
| 12 | 3 | 32 | ... The central part of a full ... | spelling of full |
| 13 | 4 | 51 | $C_m(w) = h(w) * C(w) + v(w)$ | asterisk "*" (not period) |
| 14 | 6 | 53 & 54 | ... Symbols C and E ... | no subscripts |
| 15 | 6 | 57 | ... as in $C(w)$ or $C_m(w)$ ... | "m" not subscripted |
| 16 | 6 | 64 | ... compliance $C_m(w)$ ... | ditto |
| 17 | 8 | 1 | ... $COV_E$ of estimator E ... | E not subscripted |
| 18 | 8 | 13 | ... $COV_E$ are required ... | ditto |
| 19 | 8 | 44 | ... is regular; that is, each ... | needs semicolon after regular |
| 20 | 9 | 6 | ... and *a priori* information ... | *a priori* not italicized |
| 21 | 9 | 40 | ... available *a priori* ... | ditto |
| 22 | 9 | 54 | ... of available *a priori* information ... | ditto |
| 23 | 10 | 53 | ... come from *a priori* information ... | ditto |
| 24 | 11 | 33 | $C_t(u) = C_0 + b\delta(u - \xi)$ | wrong subscript |
| 25 | 12 | 25 | ... weights $b_{j-p_1+1}$ runs ... | "p" (case is wrong) |
| 26 | 13 | 11 | ... to stage k+1 in the ... | "l" (not "1") |
| 27 | 13 | 24 | $C_m(k) = \sum_{j=-(p-1)/2}^{(p-1)/2} b_{j+(p+1)/2} C(k-j) + v(k)$ | missing minus sign on lower limit |
| 28 | 14 | 5 | ... "controllable canonical form" ... | spelling of form |
| 29 | 14 | 15 & 16 | ... values. *A priori* information ... | *A priori* not italicized |
| 30 | 14 | 17 & 18 | ... parameters. *A priori* ... | ditto |
| 31 | 16 | 26 | ... $x_1, x_2, ..., x_4$. Each ... | x (case is wrong) |

UNITED STATES PATENT AND TRADEMARK OFFICE
CERTIFICATE OF CORRECTION

PATENT NO. : 7,047,156 B1
APPLICATION NO. : 10/318711
DATED : May 16, 2006
INVENTOR(S) : Bechtel et al.

It is certified that error appears in the above-identified patent and that said Letters Patent is hereby corrected as shown below:

| | Col | Line | Corrected Text | Problem |
|---|---|---|---|---|
| 1 | | | | |
| 2 | 16 | 45 | $D_j = D_1 + S_1(x_j - x_1) + M_- \int_{x_1}^{x_j} C(w-x)(x_j - x)dx + V_- \int_{x_1}^{x_j} C(w-x)(x_j-x)(x-x_1)dx + \sum_{i=1}^{j-1} F_i \int_{x_1}^{x_j} C(w-x)(x_j-x)(x-x_i)dx = D_1 + S_1(x_j - x_1) + M_- J_{1j}(w) + V_- I_{1j}(w) + \sum_{i=1}^{j-1} F_i I_{ij}(w)$ for $j = 2, \cdots, n$ | |
| 3 | | | | The term $V_- I_{1j}(w)$ is missing |
| 4 | 16 | 65 & 66 | ... and $M_-$ and $V_-$ are ... | Use subscript hyphen or minus sign |
| 5 | 16 | 67 | ... symbols $J_{ij}$ ... | wrong subscript |
| 6 | 17 | 1 | ... $I_{ij}$, and $I_{ij}$ ... | wrong subscript |
| 7 | 17 | 11 | ... dependence of $J_{ij}$ ... | wrong subscript |
| 8 | 17 | 14 | ... and $J_{ij}$ are ... | wrong subscript |
| 9 | 17 | 24, 33 & 38 | $I_{12}F_1 + S_1(x_2 - x_1) = D_2 - D_1 - I_{12}V_- - J_{12}M_-$ $I_{13}F_1 + I_{23}F_2 + S_1(x_3 - x_1) = D_3 - D_1 - I_{13}V_- - J_{13}M_-$ $\vdots$ $I_{1n}F_1 + I_{2n}F_2 + \cdots + I_{n-1,n}F_{n-1} + S_1(x_n - x_1) = D_n - D_1 - I_{1n}V_- - J_{1n}M_-$ $F_1 + F_2 + \cdots + F_{n-1} + F_n = -(V_- + V_+)$ $(x_n - x_1)F_1 + (x_n - x_2)F_2 + \cdots + (x_n - x_{n-1})F_{n-1} = -(x_n - x_1)V_- - (M_- + M_+)$ | |
| 10 | | | | x (wrong case 2 places) |
| 11 | | | | + sign missing in $I_{n-1,n}F_{n-1} + S_1(x_n - x_1)$ |
| 12 | 17 | 57 | ... W$\underline{A}$ = $\underline{B}$ | missing underlines on $\underline{A}$ and $\underline{B}$ |
| 13 | 18 | 11 & 14 | ... $\underline{B}$ ... | missing underline on $\underline{B}$ |
| 14 | 18 | 15 | ... $\underline{A}$ ... | missing underline on $\underline{A}$ |
| 15 | 18 | 17 | $\underline{A} = W^{-1}\underline{B}$ , $\underline{B} = [D_2 \ D_3 \ \cdots \ D_n \ 0 \ 0]^T$ | |
| 16 | | | | missing underlines on $\underline{A}$ and $\underline{B}$ |
| 17 | | | | $D_n$ is not a subscript |
| 18 | 18 | 39 | ... $x_3 = -24, x_4 = 0, x_5 = 24, \ldots$ | x (wrong case) |
| 19 | 18 | 59 | ... functions $h_3, h_4,$ and $h_5$ being ... | $h_5$ (not $b_5$) |
| 20 | 19 | 7 | ... point at $x_4$ ... | x (wrong case) |
| 21 | 20 | 57 | $C(u) = C_1(u) = C_0 + b\delta(u-\xi)$ | missing equal sign after C(u) |

UNITED STATES PATENT AND TRADEMARK OFFICE
CERTIFICATE OF CORRECTION

PATENT NO. : 7,047,156 B1
APPLICATION NO. : 10/318711
DATED : May 16, 2006
INVENTOR(S) : Bechtel et al.

It is certified that error appears in the above-identified patent and that said Letters Patent is hereby corrected as shown below:

| | Col. | Line | Corrected Text | Problem |
|---|---|---|---|---|
| 2 | 21 | 53 | $C_m(b,x) = \frac{K3}{F_4} = \frac{K3}{\{W^{-1}\underline{B}\}_4} = \frac{K3}{\{(W_o+bW_d(x))^{-1}\underline{B}\}_4} = \frac{K3}{\left\{\left(I_8+bW_o^{-1}W_d(x)\right)^{-1}W_o^{-1}\underline{B}\right\}_4}$ | |
| 3 | | | | subscript "8" in $I_8$ (not "g") |
| 4 | 22 | 22 | ... in vector $\underline{B}$ and matrix ... | $\underline{B}$ (not a) |
| 5 | 22 | 59 | ... notation H3(j) indicates ... | j (not O) |
| 6 | 22 | 66 | ... weights $b_p, \ldots, b_1$, in ... | last subscript wrong |
| 7 | 23 | 13 | ... positions $x_1, x_2, x_3, x_4$, and ... | x (wrong case 2 places) |
| 8 | 23 | 25 | ... definition $x_1$ to $x_5$ ... | x (wrong case) |
| 9 | 23 | 26 | ... $x_7$. The span ... | ditto |
| 10 | 23 | 26 | ... function $h_1(x)$ is ... | h (wrong case) |
| 11 | 23 | 27 | ... $x_5 \leq x \leq x_7$, which ... | use $\leq$ for consistency |
| 12 | 23 | 66 | ... row of $W_o$, the support ... | missing subscript |
| 13 | 23 | 67 | ... with $x_5$. ... | x (wrong case) |
| 14 | 25 | 46 | ... $x_3$. ... | ditto |
| 15 | 28 | 17 | ... support point $x_4$ as shown ... | ditto |
| 16 | 29 | 41 | ... with $h_1(x) = 0$. ... | missing "h" |
| 17 | 29 | 57 | ... at $x_7 = 40$ inch ... $x_1, \ldots, x_6$ ... | x (wrong case 2 places) |
| 18 | 30 | 3 | ... at $x_3 = -24$ inch. ... | x (wrong case) |
| 19 | 30 | 7 | ... and $x_2 = -32$ inch. ... | extra = sign |
| 20 | 30 | 12 | ... $x_3, \ldots, x_7$ | x (wrong case) |
| 21 | 30 | 51 | ... $x_7$, and ... | ditto |
| 22 | 30 | 56 | ... stage 20, ... | improper bold-face |
| 23 | 30 | 57 | ... $C^*(k-18) = s_1^*(k)+C_m(12)$ until ... | missing + sign |
| 24 | 30 | 64 | ... support at $x_3$, ... | x (wrong case) |
| 25 | 31 | 2 | ... $C^*(k_f-16) = s_3^*(k_f)+C_m(12)$, and ... | wrong subscript on k; s (wrong case) |
| 26 | 31 | 3 | ... and so on until ... | missing space |
| 27 | 31 | 3 | ... $C^*(k_f+11) = s_{30}^*(k_f)+C_m(12)$, ... | s (wrong case) |
| 28 | 31 | 34 | ... than $x_7 - x_1 = 80$ inch, ... | x (wrong case); doubled minus sign |
| 29 | 31 | 61 | ... $s_2(k+1) = s_3(k)$ and ... | s (wrong case) |
| 30 | 31 | 63 | ... at 11 in FIG. 5, ... | 11 should be bold-faced |

UNITED STATES PATENT AND TRADEMARK OFFICE
CERTIFICATE OF CORRECTION

PATENT NO. : 7,047,156 B1
APPLICATION NO. : 10/318711
DATED : May 16, 2006
INVENTOR(S) : Bechtel et al.

It is certified that error appears in the above-identified patent and that said Letters Patent is hereby corrected as shown below:

| | Col | Line | Corrected Text | Problem |
|---|---|---|---|---|
| 1 | | | | |
| 2 | 32 | 7 | ... by $j = k-(p+1)/2 = k-19$ ... | wrong = sign |
| 3 | 33 | 4 | ... where $r_{xx}(m)$ is ... | missing (m) |
| 4 | 33 | 46 | $r_{yy}(p+1)+a_1 r_{yy}(p)+a_2 r_{yy}(p-1)+\cdots+a_p r_{yy}(1) = 0$ <br> $r_{yy}(p+2)+a_1 r_{yy}(p+1)+a_2 r_{yy}(p)+\cdots+a_p r_{yy}(2) = 0$ <br> $r_{yy}(p+3)+a_1 r_{yy}(p+2)+a_2 r_{yy}(p+1)+\cdots+a_p r_{yy}(3) = 0$ <br> $\vdots$ <br> $r_{yy}(p+q)+a_1 r_{yy}(p+q-1)+a_2 r_{yy}(p+q-2)+\cdots+a_p r_{yy}(q) = 0$ | |
| 5 | | | | improper bold-face of first 0 |
| 6 | 34 | 13 | $R\underline{a} = \underline{b}$ | missing underlines on $\underline{a}$ and $\underline{b}$ |
| 7 | 34 | 16 | ... vector $\underline{a}$ and the ... | missing underline & extra "s" |
| 8 | 34 | 17 | ... vector $\underline{b}$ are made ... | missing underline |
| 9 | 34 | 21 | ... vector $\underline{b}$ the ... | ditto |
| 10 | 34 | 21 | ... function $r_{yy}$ ... | subscripts on "r" |
| 11 | 34 | 22 | ... arguments 1, ..., p+q may ... | missing comma before p+q |
| 12 | 35 | 28 | ... the $r_{yy}$ function ... | subscripts on "r" |
| 13 | 35 | 32 | ... Equations: $R\underline{a} = \underline{b}$ | missing underlines on $\underline{a}$ and $\underline{b}$ |
| 14 | 35 | 33 | ... equations $R\underline{a} = \underline{b}$ | ditto |
| 15 | 35 | 34 | ... coefficients $\underline{a}$ ... | missing underline |
| 16 | 35 | 36 | ... by $R^T$, the ... | T not superscripted |
| 17 | 35 | 40 | $R^T R\underline{a} = R^T \underline{b}$ | missing underlines on $\underline{a}$ and $\underline{b}$ |
| 18 | 35 | 44 | ... of $R\underline{a} = \underline{b}$. That ... | ditto |
| 19 | 35 | 44 | ... is, $(R\underline{a} - \underline{b})^T (R\underline{a} - \underline{b})$ is ... | ditto (4 places) |
| 20 | 35 | 47 | ... $R\underline{a} = \underline{b}$ exists, and ... | ditto |
| 21 | 35 | 52 | $\underline{a} = V_r \Sigma_r^{-1} U_r^T \underline{b}$ | ditto & extra minus sign |
| 22 | 35 | 54 | ... $(\underline{a}^T \underline{a})^{1/2}$ of any ... | missing underlines on $\underline{a}$ |
| 23 | 36 | 14 | ... matrix $V_r$ and ... | missing subscript "r" |
| 24 | 36 | 23 | ... *a priori* information ... | *a priori* not italicized |
| 25 | 37 | 19 | ... *a priori* information ... | ditto |
| 26 | 37 | 22 | ... *a priori* information ... | ditto |
| 27 | 38 | 17 | ... is $s^*(12) = 0$. | missing = sign |
| 28 | 39 | 14 | ... *a priori* considerations, | *a priori* not italicized; *a* (not α) |

UNITED STATES PATENT AND TRADEMARK OFFICE
CERTIFICATE OF CORRECTION

PATENT NO.        : 7,047,156 B1
APPLICATION NO.   : 10/318711
DATED             : May 16, 2006
INVENTOR(S)       : Bechtel et al.

It is certified that error appears in the above-identified patent and that said Letters Patent is hereby corrected as shown below:

| 1. | Col | Line | Corrected Text | Problem |
|---|---|---|---|---|
| 2. | 39 | 17 | ... specify $var(u) = \sigma^2(1-\rho^2)$ ... | $\rho$ (not p) |
| 3 | 39 | 35 | $K(k) = P^*(k)H^T(k)[H(k)P^*(k)H^T(k) + var(v)]^{-1}$ | |
| 4 | | | | misplaced bracket [ & |
| 5 | | | | wrongly superscripted H |
| 6 | 39 | 43 | Compute covariance ... | extraneous "a" before Compute |
| 7 | 39 | 61 | where $y(k) = c_m(k) = C_m(k) - C_m(12)$. | C wrong case |
| 8 | 40 | 27 | ..., $H(k) = H4$; and ... | k inconsistent font |
| 9 | 40 | 44 | $E^*(j) \cong (1 + COV_C^2(j))/C^*(j)$ | missing division symbol "/" |
| 10 | 41 | 52 & 53 | ... of $0.0035\ (10^6\ psi)^{-1}$. This ... | "-1" should be superscript |
| 11 | 41 | 54 | ... than $1/(EI)$. The ... | "I" in EI (not 1) |
| 12 | 41 | 60 | $var(v) = 0.00001\ (10^6\ psi)^{-2}$ | "-2" should be superscript |
| 13 | 42 | 3 | ... *a priori* number ... | *a priori* not italicized |
| 14 | 42 | 5 | $\sigma^2 = 0.04\ (10^6\ psi)^{-2}$ | improper bold-face on "10" |
| 15 | 42 | 13 | ... coefficient $\rho$ ... | $\rho$ (not $\sigma$) |
| 16 | 42 | 45 | ... but if $\rho$ is ... | ditto |
| 17 | 42 | 46 | $\rho = .97\ \Rightarrow\ var(u) = 0.04\ (1 - 0.97^2) = 0.002364(10^6\ psi)^{-2}$ | |
| 18 | | | | $\rho$ (not $\sigma$) |
| 19 | | | | spaces needed right & left of $\Rightarrow$ |
| 20 | | | | improper bold-face on "10" |
| 21 | 42 | 49 | ... coefficient $\rho$ may ... | $\rho$ (not $\sigma$) |
| 22 | 42 | 62 | ... coefficients $a_1$ and ... | subscript "1" on $a_1$ (not ",") |
| 23 | 42 | 63 | ... (p+1,1)-dimensional ... | missing hyphen |
| 24 | 42 | 64 | ... value at 16, which ... | 16 should be bold-faced |
| 25 | 43 | 1 | ... (p+1,1)-dimensional ... | missing hyphen |
| 26 | 43 | 2 & 3 | ... (1,p+1)-dimensional ... | ditto |
| 27 | 43 | 30 | $\rho_1 = -a_1 \quad\quad \sigma_1^2 = \dfrac{var(u_1)}{1-\rho_1^2} = \alpha^2 \sigma^2$ <br> $\rho_2 = -a_2 \quad\quad \sigma_2^2 = \dfrac{var(u_2)}{1-\rho_2^2} = (1-\alpha^2)\sigma^2$ | |
| 28 | | | | needs more horizontal space between |
| 29 | | | | first and second equation in each line |

UNITED STATES PATENT AND TRADEMARK OFFICE
CERTIFICATE OF CORRECTION

PATENT NO. : 7,047,156 B1
APPLICATION NO. : 10/318711
DATED : May 16, 2006
INVENTOR(S) : Bechtel et al.

It is certified that error appears in the above-identified patent and that said Letters Patent is hereby corrected as shown below:

| | Col | Line | Corrected Text | Problem |
|---|---|---|---|---|
| 1 | | | | |
| 2 | 43 | 35 | $0 \leq \alpha^2 \leq 1$ | $\leq$ for consistency, two places |
| 3 | 44 | 2 | ... of FIG. 6 if ... | extraneous "is" |
| 4 | 44 | 14 | ... where $0 < \rho_1 < \rho_2 < 1$. By ... | "1" (not l); improper bold-face |
| 5 | 44 | 32-34 | $y(k) = (\rho_1 + \rho_2)y(k-1) - \rho_1\rho_2 y(k-2) + b_1(u_1(k-1) + u_2(k-1)) + \sum_{j=2}^{p}[(b_j - \rho_2 b_{j-1})u_1(k-j) + (b_j - \rho_1 b_{j-1})u_2(k-j)] + v(k)$ | |
| 6 | | | | Brackets [ ] are required about |
| 7 | | | | summand if split into 2 lines. |
| 8 | 44 | 50 | ... then $\rho_1$ and $\rho_2$ may ... | $\rho_2$ (not $\sigma_2$) |
| 9 | 45 | 9 | ... or $\omega = 1.3739$ radian/sample. | $\omega$ (not X) |
| 10 | 45 | 12 | ... or $\gamma = 0.9^{0.21866}$ ... | missing decimal point in superscript |
| 11 | 45 | 13 | ... coefficients $\beta$ and $-\gamma^2$ are ... | $-\gamma^2$ (not $-35^2$) |
| 12 | 45 | 18 | $-\gamma^2 = -0.97723^2 = -0.9550$ $\beta = 2\gamma \cos(\omega) = (2)(0.97723)\cos(1.3739) = 0.3824$ | |
| 13 | | | | last equal sign is missing |
| 14 | 45 | 22 | ... at 17 as shown ... | 17 should be bold-faced |
| 15 | 46 | 1 | ... and $u_3$ are ... | u (wrong case) |
| 16 | 46 | 14 | ... Estimation of $s_{p+1}$ can ... | not "sips" |
| 17 | 46 | 23 | ... of *a priori* information ... | *a priori* not italicized |
| 18 | 46 | 32 | ... of $\rho_b$ as defining ... | $\rho_b$ (not Pb) |
| 19 | 46 | 38 | ... 0.5 $(10^6 \text{ psi})^{-1}$ for ... | $10^6$ (not 106) |
| 20 | 46 | 42 | ... by $\text{var}(u) = \sigma^2(1-\rho_b^2)$. The ... | $-\rho_b^2$ (not $=\sigma_b^2$) |
| 21 | 46 | 67 | ... and 69 for ... | 69 should be bold-faced |
| 22 | 47 | 29 | ... function $E^*$ is shown ... | missing asterisk |
| 23 | 47 | 30 | ... variation $COV_E$ is ... | E not subscripted |
| 24 | 47 | 37 | ... e.g. $\rho_a = 0.999$, cause ... | $\rho_a$ (not $p_r$) |
| 25 | 48 | 3 & 4 | ... $\text{var}(u) = \sigma^2(1-\rho_a^2) = $ ... | missing minus sign |
| 26 | 48 | 26 | ... and *a priori* information. | *a priori* not italicized |
| 27 | 48 | 48 | ... and *a priori* Information ... | ditto |

UNITED STATES PATENT AND TRADEMARK OFFICE
CERTIFICATE OF CORRECTION

PATENT NO.        : 7,047,156 B1
APPLICATION NO.   : 10/318711
DATED             : May 16, 2006
INVENTOR(S)       : Bechtel et al.

It is certified that error appears in the above-identified patent and that said Letters Patent is hereby corrected as shown below:

| | Col | Line | Corrected Text | Problem |
|---|---|---|---|---|
| 1 | | | | |
| 2 | | | | |
| 3 | 49 | 21 | … and *a priori* … | *a priori* not italicized |
| 4 | 49 | 28 | … labeled M1, and … | M1 should be bold-faced |
| 5 | 49 | 29 | … Cm1 in … | Cm1 should be bold-faced |
| 6 | 49 | 30 | … labeled m1 in | m1 should be bold-faced |
| 7 | 49 | 32 | … and *a priori* Information … | *a priori* not italicized; need space after *a* |
| 8 | 49 | 35 | … labeled d1 in … | d1 should be bold-faced |
| 9 | 49 | 36 | … labeled n1 to obtain … | n1 (not a1); n1 should be bold-faced |
| 10 | 49 | 37 | … labeled D1. The … | D1 should be bold-faced |
| 11 | 49 | 47 | … Modeling *a priori* … | *a priori* not italicized |
| 12 | 49 | 47 | … Information block. | missing period |
| 13 | 50 | 1 | First Alternative … | spelling of "First" |
| 14 | 50 | 7 | … $x_3 = L/2$; $L = x_3-x_1$ being … | x (wrong case 2 places) |
| 15 | 50 | 19 | … references are … | spelling of "are" |
| 16 | 50 | 34 | … that W$\underline{A}$ = $\underline{B}$ where … | missing underlines on $\underline{A}$ and $\underline{B}$ |
| 17 | 50 | 65 | … of $W_o^{-1}\underline{B}$ may … | missing underline on $\underline{B}$ |
| 18 | 50 | 66 | … with $\underline{A} = [F_1, F_2, F_3, S_1]^T$ … | missing underline on $\underline{A}$ |
| 19 | 51 | 23 | … labeled 900. | 900 should be bold-faced |
| 20 | 52 | 28 | … is $\{\underline{A}\}_{2+3} = F_2+F_3$. | missing underline on $\underline{A}$ |
| 21 | 52 | 30 | … of $\underline{A}$ satisfy $-F_1 = F_2 = F_3 = -F_4$. | ditto |
| 22 | 52 | 31 | … of $\underline{A}$, namely… | ditto |
| 23 | 52 | 54 | … equations W$\underline{A}$ = $\underline{B}$, when … | missing underlines on $\underline{A}$ and $\underline{B}$ |
| 24 | 53 | 56 | or:   W$\underline{A}$ = $\underline{B}$F | This entire line is missing see specification page 76, line 2 |
| 25 | | | | |
| 26 | | | | |
| 27 | 54 | 11 | … measured at 56. | 56 should be bold-faced |
| 28 | 54 | 19 | … where $D_3 = \{\underline{A}\}_2$, which … | missing underline on $\underline{A}$ |
| 29 | 54 | 24 | … vector $\underline{B}$ are … | missing underline on $\underline{B}$ |
| 30 | 54 | 27-29 | $W = W_o + bW_d(x)$<br>$\underline{B} = \underline{B}_o + b\underline{B}_d(x)$ | $+bW_d$ shouldn't be subscripted<br><br>missing underlines on $\underline{B}$, $\underline{B}_o$, and $\underline{B}_d$ |
| 31 | | | | |

UNITED STATES PATENT AND TRADEMARK OFFICE
CERTIFICATE OF CORRECTION

PATENT NO.       : 7,047,156 B1                                        Page 8 of 11
APPLICATION NO.  : 10/318711
DATED            : May 16, 2006
INVENTOR(S)      : Bechtel et al.

It is certified that error appears in the above-identified patent and that said Letters Patent is hereby corrected as shown below:

| # | Col | Line | Corrected Text | Problem |
|---|-----|------|----------------|---------|
| 1 |     |      | $h(x) = \dfrac{\partial C_m(b,x)}{\partial b}\bigg|_{b=0} = \lim_{b \to 0} \dfrac{C_m(b,x) - C_o}{b} = \lim_{b \to 0} \dfrac{1}{b}\left[\dfrac{K\{W^{-1}\underline{B}\}_2 F}{F} - \dfrac{K\{W_o^{-1}\underline{B}_o\}_2 F}{F}\right]$ | |
| 2 | 55  | 21-23 | $= \lim_{b \to 0} \dfrac{K}{b}\left[\{W^{-1}\underline{B}\}_2 - \{W_o^{-1}\underline{B}_o\}_2\right]$ $= \lim_{b \to 0} \dfrac{K}{b}\left[\{(W_o + bW_d)^{-1}(\underline{B}_o + b\underline{B}_d(x))\}_2 - \{W_o^{-1}\underline{B}_o\}_2\right]$ $= \lim_{b \to 0} \dfrac{K}{b}\left[\{(I + bW_o^{-1}W_d)^{-1}(W_o^{-1}\underline{B}_o + bW_o^{-1}\underline{B}_d(x))\}_2 - \{W_o^{-1}\underline{B}_o\}_2\right]$ $= \lim_{b \to 0} \dfrac{K}{b}\left[\{(I - bW_o^{-1}W_d)(W_o^{-1}\underline{B}_o + bW_o^{-1}\underline{B}_d(x))\}_2 - \{W_o^{-1}\underline{B}_o\}_2\right]$ $= \lim_{b \to 0} \dfrac{K}{b}\left[\{-bW_o^{-1}W_d W_o^{-1}\underline{B}_o + bW_o^{-1}\underline{B}_d(x) - b^2 W_o^{-1}W_d W_o^{-1}\underline{B}_d(x)\}_2\right]$ $= K\left[\{-W_o^{-1}W_d W_o^{-1}\underline{B}_o + W_o^{-1}\underline{B}_d(x)\}_2\right]$ $= C_o \dfrac{\{-W_o^{-1}W_d(x)W_o^{-1}\underline{B}_o + W_o^{-1}\underline{B}_d(x)\}_2}{\{W_o^{-1}\underline{B}_o\}_2}$ , $x_1 < x \leq x_5$ | In successive lines where $(I + bW_o^{-1}W_d)^{-1}$ and $(I - bW_o^{-1}W_d)$ are factors, "I" (not 1) |
| 3 |     |      |                | |
| 4 |     |      |                | |
| 5 |     |      |                | |
| 6 | 55  | 34   | With $L = x_5 - x_1$, the … | x (wrong case) |
| 7 | 55  | 62   | … products $W_o^{-1}\underline{B}_o$ and … | missing underline on $\underline{B}_o$ |
| 8 | 55  | 63   | … $W_o^{-1}\underline{B}_d(x)$ used … | missing underline on $\underline{B}_d$ |
| 9 | 57  | 15   | $H\underline{C} = \underline{C}_m$ | missing underlines on $\underline{C}$ and $\underline{C}_m$ |
| 10 | 57 | 17   | $\underline{C}$ is an … | missing underline on $\underline{C}$ |
| 11 | 57 | 18   | … $\underline{C}_m$, is a … | missing underline on $\underline{C}_m$ |
| 12 | 57 | 20   | … values $\underline{C}$ are … | missing underline on $\underline{C}$ |
| 13 | 57 | 21   | … $\underline{C}_m$, where … | missing underline on $\underline{C}_m$ |
| 14 | 57 | 21   | … where $N = \kappa + p - 1$. | superfluous $K^+$ |
| 15 | 57 | 54   | … of $\underline{C}$ occur … | missing underline on $\underline{C}$ |
| 16 | 57 | 56   | … minimizing $\underline{C}^T\underline{C}$, is: | missing underline on $\underline{C}$ (2 places) |
| 17 | 57 | 57   | $\underline{C} = V_\kappa S_\kappa^{-1} U^T \underline{C}_m$ | missing underlines on $\underline{C}$ and $\underline{C}_m$ |
| 18 | 58 | 9    | … vector $\underline{C}$ has … | missing underline on $\underline{C}$ |
| 19 | 58 | 12 & 13 | … solution $\underline{C} = V_\kappa S_\kappa^{-1} U^T \underline{C}_m$, … | missing underlines on $\underline{C}$ and $\underline{C}_m$; superscript -1 on $S_\kappa^{-1}$ is misplaced must be kept with root symbol S |
| 20 |    |      |                | |
| 21 |    |      |                | |

UNITED STATES PATENT AND TRADEMARK OFFICE
CERTIFICATE OF CORRECTION

PATENT NO. : 7,047,156 B1
APPLICATION NO. : 10/318711
DATED : May 16, 2006
INVENTOR(S) : Bechtel et al.

It is certified that error appears in the above-identified patent and that said Letters Patent is hereby corrected as shown below:

| | Col | Line | Corrected Text | Problem |
|---|---|---|---|---|
| 1 | | | | |
| 2 | 58 | 16 | ... $\underline{C}$ without changing H$\underline{C}$ ... | missing underline on $\underline{C}$ (2 places) |
| 3 | 58 | 18 | $\underline{C} = V_\kappa S_\kappa^{-1} U^T \underline{C}_m + V_n \underline{\gamma}$ | missing underlines on $\underline{C}$ and $\underline{C}_m$ |
| 4 | | | | missing $\underline{\gamma}$; extraneous ± |
| 5 | 58 | 20 | ... where $\underline{\gamma}$ is any ... | missing underline on $\underline{\gamma}$ |
| 6 | 58 | 21 | ... to $\underline{C}$ by ... | missing underline on $\underline{C}$ |
| 7 | 58 | 22 | ... the N-κ = p-1 orthonormal ... | p (wrong case) |
| 8 | 58 | 31 | ... of $\underline{C}$ except ... | missing underline on $\underline{C}$ |
| 9 | 58 | 32 | ... beam-ends, by ... | spelling of beam |
| 10 | 58 | 32 | ... form $V_n \underline{\gamma}$. | missing underline on $\underline{\gamma}$ |
| 11 | 58 | 34 | ... of $\underline{C}$ to be ... | missing underline on $\underline{C}$ |
| 12 | 58 | 36 | ... $\underline{C}$ to be equal ... | ditto |
| 13 | 58 | 40 | ... vector $\underline{C}_m$ thereby ... | missing underline on $\underline{C}_m$ |
| 14 | 58 | 41 | ... solution $\underline{C}_a$ of the ... | missing underline on $\underline{C}_a$ |
| 15 | 58 | 42 | $H_a \underline{C}_a = \underline{C}_{ma}$ | missing underlines on $\underline{C}_a$ and $\underline{C}_{ma}$ |
| 16 | 58 | 44 | ... (N,1)-dimensional ... | missing hyphen |
| 17 | 58 | 44 | ... vector $\underline{C}_{ma}$ is ... | missing underline on $\underline{C}_{ma}$ |
| 18 | 58 | 46 | ... vector $\underline{C}_m$ according ... | missing underline on $\underline{C}_m$ |
| 19 | 59 | 5 | ... of $\underline{C}_a$ to equal ... | missing underline on $\underline{C}_a$ |
| 20 | 59 | 7 | ... for $\underline{C}_a$ from ... | ditto |
| 21 | 59 | 8 | ... $\underline{C}_a = H_a^{-1} \underline{C}_{ma}$. In ... | missing underlines on $\underline{C}_a$ and $\underline{C}_{ma}$ |
| 22 | | | | =$H_a$ is not a subscript |
| 23 | 59 | 9 | ... equation $H_a \underline{C}_a = \underline{C}_{ma}$ can ... | missing underlines on $\underline{C}_a$ and $\underline{C}_{ma}$ |
| 24 | 59 | 37 | ... reciprocal $\underline{E} = 1./\underline{C}$ of ... | missing underlines on $\underline{E}$ and $\underline{C}$ |
| 25 | 59 | 39 | ... the vector $\underline{C}$. The ... | missing underline on $\underline{C}$ |
| 26 | 59 | 41 | ... is $1./\underline{C}_m$ the ... | missing underline on $\underline{C}_m$ |
| 27 | 59 | 42 | ... vector $\underline{C}_m$. The ... | ditto |
| 28 | 59 | 46 | ... in $\underline{C}$. That is, $\underline{C}_m = H\underline{C}$. The ... | missing underlines on $\underline{C}$ and $\underline{C}_m$ |
| 29 | 59 | 48 | ... estimates $\underline{E}_a$ of ... | missing underline on $\underline{E}_a$ |
| 30 | 59 | 50 | ... vector $\underline{C}_a$ obtained ... | missing underline on $\underline{C}_a$ |
| 31 | 59 | 53 | ... relationship $\underline{C}_a = H_a^{-1} \underline{C}_{ma}$ ... | missing underlines on $\underline{C}_a$ and $\underline{C}_{ma}$ |

UNITED STATES PATENT AND TRADEMARK OFFICE
CERTIFICATE OF CORRECTION

PATENT NO.        : 7,047,156 B1
APPLICATION NO.   : 10/318711
DATED             : May 16, 2006
INVENTOR(S)       : Bechtel et al.

It is certified that error appears in the above-identified patent and that said Letters Patent is hereby corrected as shown below:

|    | Col | Line | Corrected Text | Problem |
|----|-----|------|----------------|---------|
| 1  |     |      |                |         |
| 2  | 59  | 56   | $\underline{E}_a = (I./H_a^{-1}\underline{C}_{ma})_* *(1+COV_{\underline{C}}^2)$ | missing underlines on $\underline{E}_a$ and $\underline{C}_{ma}$ |
| 3  | 59  | 60   | ... generated $\underline{E}$ curve ... | missing underline on $\underline{E}$ |
| 4  | 59  | 62   | ... $\underline{E}_a$. However, oscillations in $\underline{E}_a$ ... | missing underlines on $\underline{E}_a$ (two places) |
| 5  | 59  | 63   | ... generated $\underline{E}$ of ... | missing underline on $\underline{E}$ |
| 6  | 60  | 7    | ... difference $\underline{C}_a - \underline{C}_{ma}$ ... | missing underlines on $\underline{C}_a$ and $\underline{C}_{ma}$ |
| 7  | 60  | 8    | ... of $\underline{C}_a$ and $\underline{C}_{ma}$. | ditto |
| 8  | 60  | 12   | ... values $\underline{C}_{ma}$ ... | wrong subscripts and missing underline |
| 9  | 60  | 13   | ... a result $\underline{C}_{aI}$ is ... | $\underline{C}_{aI}$ (not A) |
| 10 | 60  | 26   | ... 1./$\underline{C}_{aI}$ for j = 2. | missing underline on $\underline{C}_{aI}$ |
| 11 | 60  | 26   | ... shown is 1./$\underline{C}$ as curve ... | missing underline on $\underline{C}$ |
| 12 | 60  | 27   | ... and 1./$\underline{C}_m$ as ... | missing underline on $\underline{C}_m$ |
| 13 | 60  | 36   | ... dots is $\underline{E}_m = 1./\underline{C}_m$, the ... | missing underlines on $\underline{E}_m$ and $\underline{C}_m$ |
| 14 | 60  | 37   | ... vector $\underline{C}_m$. | missing underline on $\underline{C}_m$ |
| 15 | 60  | 38   | ... as $\underline{E}_a$ the ... | missing underline on $\underline{E}_a$ |
| 16 | 60  | 40   | ... ad hoc curves 1./$\underline{C}_{aI}$ are ... | missing underline on $\underline{C}_{aI}$ |
| 17 | 60  | 44   | ... of 1./$\underline{C}_{aI}$ track ... | ditto |
| 18 | 60  | 44   | ... measured $\underline{E}_m$ ... | missing underline on $\underline{E}_m$ |
| 19 | 60  | 49   | ... system H$\underline{C}$ = $\underline{C}_m$ where ... | missing underlines on $\underline{C}$ and $\underline{C}_m$ |
| 20 | 60  | 62   | ... equation H$\underline{C}$ = $\underline{C}_m$ is ... | ditto |
| 21 | 61  | 13   | ... vector $\underline{C}_m$ that ... | missing underline on $\underline{C}_m$ |
| 22 | 61  | 16   | ... of $\underline{C}$ in domain ... | missing underline on $\underline{C}$ |
| 23 | 61  | 18   | ... of $\underline{C}_m$ is ... | missing underline on $\underline{C}_m$ |
| 24 | 61  | 22   | ... machine $MA_1$ were ... | $MA_1$ (not $MA_l$) |
| 25 | 61  | 27   | ... to $\underline{C}_m$ via ... | missing underline on $\underline{C}_m$ |
| 26 | 61  | 30   | ... in $\underline{C}_m$ correspond. ... | ditto |
| 27 | 61  | 33   | ... of $\underline{C}$. | missing underline on $\underline{C}$ |
| 28 | 61  | 35   | ... measurements $\underline{C}_m$. | missing underline on $\underline{C}_m$ |
| 29 | 61  | 36   | ... $\underline{C}$ as before ... | missing underline on $\underline{C}$ |
| 30 | 61  | 39   | ... vector $\underline{C}_m$, may ... | missing underline on $\underline{C}_m$ |
| 31 | 61  | 43   | ... determination of $\underline{C}$, ... | missing underline on $\underline{C}$ |
| 32 | 61  | 58   | ... H$\underline{C}$ = $\underline{C}_m$. ... | missing underlines on $\underline{C}$ and $\underline{C}_m$ |

UNITED STATES PATENT AND TRADEMARK OFFICE
CERTIFICATE OF CORRECTION

PATENT NO. : 7,047,156 B1
APPLICATION NO. : 10/318711
DATED : May 16, 2006
INVENTOR(S) : Bechtel et al.

It is certified that error appears in the above-identified patent and that said Letters Patent is hereby corrected as shown below:

| | Col | Line | Corrected Text | Problem |
|---|---|---|---|---|
| 1 | | | | |
| 2 | 61 | 61 | ... by increasing $\Psi$, it ... | $\Psi$ (not A) |
| 3 | | | | |
| 4 | CLAIMS | | | |
| 5 | 62 | 38 | ... vector $\underline{C}$ with ... | missing underline on $\underline{C}$ |
| 6 | 62 | 41 | ... vector $\underline{C}_m$ with ... | missing underline on $\underline{C}_m$ |
| 7 | 62 | 50 | ... vector $\underline{C}$ is ... | missing underline on $\underline{C}$ |
| 8 | 62 | 51 | ... vector $\underline{C}$ corresponding ... | ditto |
| 9 | 62 | 52 | ... in $\underline{C}_m$; and | missing underline on $\underline{C}_m$ |
| 10 | 62 | 53 | ... computing $\underline{C}$ as ... | missing underline on $\underline{C}$ |
| 11 | 62 | 53 | ... to $H\underline{C} = \underline{C}_m$, the ... | missing underlines on $\underline{C}$ and $\underline{C}_m$ |
| 12 | 62 | 58 | ... vector $\underline{C}_{ma}$ giving ... | missing underline on $\underline{C}_{ma}$ |
| 13 | 62 | 59 | ... solution $\underline{C}_a$ of ... | missing underline on $\underline{C}_a$ |
| 14 | 62 | 59 | ... equation $\underline{C}_{ma} = H_a \underline{C}_a$, the ... | missing underlines on $\underline{C}_{ma}$ and $\underline{C}_a$ |
| 15 | | | | missing "a" in subscript of $\underline{C}_{ma}$ |
| 16 | 62 | 59 | ... solution $\underline{C}_a$ being ... | missing underline on $\underline{C}_a$ |
| 17 | 62 | 60 | ... of $\underline{C}_a$ ... | ditto |
| 18 | 62 | 62 | $\underline{C}_a$ being a uniform value; whereby $\underline{C}_a$ ... | missing underline on $\underline{C}_a$ (2 places) |
| 19 | 63 | 31 | using *a priori* information ... | *a priori* not italicized |
| 20 | 64 | 47 & 48 | ... as *a priori* information ... | ditto |

Signed and Sealed this

Second Day of January, 2007

JON W. DUDAS
*Director of the United States Patent and Trademark Office*